(12) United States Patent
Deisseroth et al.

(10) Patent No.: US 9,969,783 B2
(45) Date of Patent: May 15, 2018

(54) OPSIN POLYPEPTIDES AND METHODS OF USE THEREOF

(71) Applicant: The Board of Trustees of the Leland Stanford Junior University, Stanford, CA (US)

(72) Inventors: Karl Deisseroth, Stanford, CA (US); Feng Zhang, Cambridge, MA (US); Viviana Gradinaru, Pasadena, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days. days.

(21) Appl. No.: 15/799,881

(22) Filed: Oct. 31, 2017

(65) Prior Publication Data

US 2018/0044388 A1 Feb. 15, 2018

Related U.S. Application Data

(62) Division of application No. 15/334,007, filed on Oct. 25, 2016, now Pat. No. 9,840,541, which is a division of application No. 15/097,925, filed on Apr. 13, 2016, now Pat. No. 9,505,817, which is a division of application No. 14/365,477, filed as application No. PCT/US2012/069133 on Dec. 12, 2012, now Pat. No. 9,365,628.

(60) Provisional application No. 61/576,858.

(51) Int. Cl.
| | | |
|---|---|---|
| C07K 14/47 | (2006.01) | |
| C12N 13/00 | (2006.01) | |
| C07K 14/415 | (2006.01) | |
| A61N 5/06 | (2006.01) | |
| A61K 48/00 | (2006.01) | |
| A61K 38/00 | (2006.01) | |

(52) U.S. Cl.
CPC ............... *C07K 14/47* (2013.01); *A61N 5/06* (2013.01); *C07K 14/415* (2013.01); *C12N 13/00* (2013.01); *A61K 38/00* (2013.01); *A61K 48/00* (2013.01); *A61K 48/005* (2013.01); *C07K 2319/03* (2013.01); *C07K 2319/04* (2013.01); *C07K 2319/60* (2013.01)

(58) Field of Classification Search
None
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |

(Continued)

FOREIGN PATENT DOCUMENTS

| | | |
|---|---|---|
| CN | 1079464 A | 12/1993 |
| CN | 102076866 A | 5/2011 |

(Continued)

OTHER PUBLICATIONS

Co-pending U.S. Appl. No. 15/620,611, filed Jun. 12, 2017.
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.

(Continued)

*Primary Examiner* — Suzanne M Noakes
*Assistant Examiner* — Jae W Lee
(74) *Attorney, Agent, or Firm* — Bozicevic, Field & Francis LLP; Paula A. Borden

(57) ABSTRACT

The present disclosure provides opsins, including variant opsins with increased activity and/or increased trafficking to the plasma membrane. The opsins are useful in therapeutic and screening applications, which are also provided.

5 Claims, 15 Drawing Sheets

(56) References Cited

U.S. PATENT DOCUMENTS

| | | |
|---|---|---|
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Deisseroth et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,284,353 B2 | 3/2016 | Deisseroth et al. |
| 9,308,392 B2 | 4/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,360,472 B2 | 6/2016 | Deisseroth et al. |
| 9,365,628 B2 | 6/2016 | Deisseroth et al. |
| 9,394,347 B2 | 7/2016 | Deisseroth et al. |
| 9,421,258 B2 | 8/2016 | Deisseroth et al. |
| 9,453,215 B2 | 9/2016 | Deisseroth et al. |
| 9,458,208 B2 | 10/2016 | Deisseroth et al. |
| 9,505,817 B2 | 11/2016 | Deisseroth et al. |
| 9,522,288 B2 | 12/2016 | Deisseroth et al. |
| 9,604,073 B2 | 3/2017 | Deisseroth et al. |
| 9,615,789 B2 | 4/2017 | Deisseroth et al. |
| 9,636,380 B2 | 5/2017 | Lammel et al. |
| 9,693,692 B2 | 7/2017 | Deisseroth et al. |
| 9,757,587 B2 | 9/2017 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0267118 A1 | 12/2004 | Dawson |
| 2005/0020945 A1 | 1/2005 | Tosaya et al. |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Franciscelli et al. |

(56) References Cited

U.S. PATENT DOCUMENTS

| | | |
|---|---|---|
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0253261 A1 | 10/2012 | Poletto et al. |
| 2013/0030275 A1 | 1/2013 | Seymour et al. |
| 2013/0144359 A1 | 6/2013 | Kishawi et al. |
| 2013/0286181 A1 | 10/2013 | Betzig et al. |
| 2013/0289669 A1 | 10/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0324133 A1 | 10/2014 | Deisseroth et al. |
| 2015/0040249 A1 | 2/2015 | Deisseroth et al. |
| 2015/0112411 A1 | 4/2015 | Beckman et al. |
| 2015/0165227 A1 | 6/2015 | Deisseroth et al. |
| 2015/0217128 A1 | 8/2015 | Deisseroth et al. |
| 2016/0015996 A1 | 1/2016 | Deisseroth et al. |
| 2016/0038761 A1 | 2/2016 | Deisseroth et al. |
| 2016/0038764 A1 | 2/2016 | Deisseroth et al. |
| 2016/0045599 A1 | 2/2016 | Deisseroth et al. |
| 2016/0096036 A1 | 4/2016 | Deisseroth et al. |
| 2016/0175607 A1 | 6/2016 | Deisseroth et al. |
| 2016/0194624 A1 | 7/2016 | Deisseroth et al. |
| 2016/0199663 A1 | 7/2016 | Deisseroth et al. |
| 2016/0237126 A1 | 8/2016 | Deisseroth et al. |
| 2016/0252524 A1 | 9/2016 | Deisseroth et al. |
| 2016/0258929 A1 | 9/2016 | Deisseroth et al. |
| 2016/0279267 A1 | 9/2016 | Deisseroth et al. |
| 2016/0303192 A1 | 10/2016 | Deisseroth et al. |
| 2016/0316730 A1 | 11/2016 | Deisseroth et al. |
| 2016/0316732 A1 | 11/2016 | Deisseroth et al. |
| 2016/0317658 A1 | 11/2016 | Deisseroth et al. |
| 2016/0331995 A1 | 11/2016 | Deisseroth et al. |
| 2017/0056467 A1 | 3/2017 | Deisseroth et al. |
| 2017/0066806 A1 | 3/2017 | Deisseroth et al. |
| 2017/0072219 A1 | 3/2017 | Deisseroth et al. |
| 2017/0095556 A1 | 4/2017 | Deisseroth et al. |
| 2017/0143986 A1 | 5/2017 | Deisseroth et al. |
| 2017/0157269 A1 | 6/2017 | Deisseroth et al. |
| 2017/0160360 A1 | 6/2017 | Deisseroth et al. |
| 2017/0198017 A1 | 7/2017 | Deisseroth et al. |
| 2017/0202912 A1 | 7/2017 | Lammel et al. |
| 2017/0211040 A1 | 7/2017 | Deisseroth et al. |

FOREIGN PATENT DOCUMENTS

| | | |
|---|---|---|
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |

(56) References Cited

FOREIGN PATENT DOCUMENTS

| | | |
|---|---|---|
| JP | H 09505771 A | 6/1997 |
| JP | 2004534508 | 11/2004 |
| JP | 2005034073 A | 2/2005 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The *Drosophila rhodopsin* cytoplasmic tail domain is required for maintenance of rhabdomere structure." The FASEB Journal, 2007, vol. 21, p. 449-455.
Airan, et al.; "Integration of light-controlled neuronal firing and fast circuit imaging"; Current Opinion in Neurobiology; vol. 17, pp. 587-592 (2007).
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007; vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Alilain, et al.; "Light-Induced Rescue of Breathing after Spinal Cord Injury"; The Journal of Neuroscience; vol. 28, No. 46, pp. 11862-11870 (Nov. 12, 2008).
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the *cre* Gene Mediated by Cre Recombinase Using a Combination of Mutant *lox* Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Azizgolshani, et al.; "Reconstituted plant viral capsids can release genes to mammalian cells"; Virology; vol. 441, No. 1, pp. 12-17 (2013).
Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.

(56) References Cited

OTHER PUBLICATIONS

Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga *Volvox carteri*", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cannon, et al.; "Endophenotypes in the Genetic Analyses of Mental Disorders"; Annu. Rev. Clin. Psychol.; vol. 2, pp. 267-290 (2006).
Cardin, et al. "Driving Fast spiking Cells Induces Gamma Rhythm and Controls Sensory Responses", 2009, Nature, vol. 459, vol. 7247, pp. 663-667.
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.

Cenatiempo "Prokaryotic gene expression in vitro: transcription-translation coupled systems", Biochimie, 1986, vol. 68(4): pp. 505-515.
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Chow, et al.; "High-performance genetically targetable optical neural silencing by light-driven proton pumps"; Nature; vol. 463, pp. 98-102 (Jan. 7, 2010).
Chow et al., "Optogenetics and translation medicine", Sci Transl Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA, 1983, vol. 80, p. 1111-1115.
Coleman, et al.; "Assessing Anxiety in Nonhuman Primates"; Ilar Journal; vol. 55, No. 2, pp. 333-346 (2014).
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol., 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994, vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.
Davidson, et al.; "Viral Vectors for Gene Delivery to the Nervous System"; Nature Reviews Neuroscience; vol. 4, pp. 353-364 (May 2003).
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Implant; Merriam-Webster Dictionary; retrieved Nov. 7, 2016 (http://www.merriam-webster.com/dictionaly/implant).
Definition of integral. Merriam-Webster Dictionary, retrieved on Mar. 20, 2017; Retrieved from the internet: <http://www.merriam-webster.com/dictionary/integral>.

(56) References Cited

OTHER PUBLICATIONS

Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Deonarain; "Ligand-targeted receptor-mediated vectors for gene delivery"; Exp. Opin. Ther. Patents; vol. 8, No. 1, pp. 53-69 (1998).
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "N. pharaonis halorhodopsin (hop) gene, complete cds"; (Nov. 22, 1990).
EBI accession No. UNIPROT: A7U0Y6; "SubName: Full=Bacteriorhodopsin"; (Aug. 10, 2010).
EBI accession No. UNIPROT: B0R5N9; "Subname: Full=Bacteriorhodopsin"; (Apr. 8, 2008).
EBI accession No. UNIPROT: B4Y103; "SubName: Full=Channelrhodopsin-1"; (Sep. 23, 2008).
EBI accession No. UNIPROT: P15647; "RecName: Full=Halorhodopsin; Short=HR; Alt Name: Full=NpHR"; (Apr. 1, 1990).
Edelstein, et al.; "Gene therapy clinical trials worldwide 1989-2004—an overview"; The Journal of Gene Medicine; vol. 6, pp. 597-602 (2004).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain" , Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Fanselow, et al.; "Why We Think Plasticity Underlying Pavlovian Fear Conditioning Occurs in the Basolateral Amygdala"; Neuron; vol. 23, pp. 229-232 (Jun. 1999).
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Ferenczi, et al.; "Optogenetic approaches addressing extracellular modulation of neural excitability"; Scientific Reports; vol. 6, 20 pages (Apr. 5, 2016).
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.

(56) References Cited

OTHER PUBLICATIONS

Gong, et al.; "Enhanced Archaerhodopsin Fluorescent Protein Voltage Indicators"; Plos One; vol. 8, Issue 6, 10 pages (Jun. 2013).
Gonzalez, et al., "Cell-Based Assays and Instrumentation for Screening Ion-Channel Targets", DDT, 1999, vol. 4, No. 9, pp. 431-439.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat ", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Grady, et al.; "Age-Related Reductions in Human Recognition Memory Due to Impaired Encoding"; Science; vol. 269, No. 5221, pp. 218-221 (Jul. 14, 1995).
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Gritton, et al.; "Optogenetically-evoked cortical cholinergic transients in mice expressing channelrhodopsin-2 (Ch R2) in cholinergic neurons"; Society for Neuroscience Abstract Viewer and Itnery Planner & 40th Annual Meeting of the Society-for-Neuroscience; vol. 40, 2 pages (2010).
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al. "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hagglund, et al.; "Activation of groups of excitatory neurons in the mammalian spinal cord or hindbrain evokes locomotion"; Nature Neuroscience; vol. 13, No. 2, 8 pages (Feb. 2010).
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.

Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylcholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane, " PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers"Journal of Cell Science, 2005, vol. 118, p. 1935-1943.
Hosokawa, T. et al. "Imaging spatia-temporal patterns of long-term potentiation in mouse hippocampus." Philos. Trans. R. Soc. Lond. B., 2003, vol. 358, pp. 689-693.
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.

(56) References Cited

OTHER PUBLICATIONS

Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Johnson-Saliba, et al.; "Gene Therapy: Optimising DNA Delivery to the Nucleus"; Current Drug Targets; vol. 2, pp. 371-399 (2001).
Johnston et al. "Isolation of the yeast regulatory gene GAL4 and analysis of its dosage effects on the galactose/melibiose regulon," PNAS, 1982, vol. 79, pp. 6971-6975.
Jones, et al.; "Animal Models of Schizophrenia"; British Journal of Pharmacology; vol. 164, pp. 1162-1194 (2011).
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).

Khodakaramian, et al. "Expression of Cre Recombinase during Transient Phage Infection Permits Efficient Marker Removal in Streptomyces," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-10.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421 : pp. 844-848.
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kravitz, et al.; "Regulation of parkinsonian motor behaviours by optogenetic control of basal ganglia circuitry"; Nature; vol. 466, No. 622, 8 pages (Jul. 29, 2010).
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423):212-217.

(56) References Cited

OTHER PUBLICATIONS

Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li, et al.; "A Method for Activation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Biol. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.
Lin, "A user's guide to channelrhodopsin variants: features, limitations and future developments", Exp Physiol, 2010, vol. 96, No. 1, pp. 19-25.
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Luo, et al.; "Synthetic DNA delivery systems"; Nature Biotechnology; vol. 18, pp. 33-37 (Jan. 2000).
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Maestripieri, et al.; "A modest proposal: displacement activities as an indicator of emotions in primates"; Anim. Behav.; vol. 44, pp. 967-979 (1992).

Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photowitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003, vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.

(56) References Cited

OTHER PUBLICATIONS

Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using Drosophila Rh1-bovine rhodopsin chimeras," Vision Res., 2006, vol. 46, No. 27: pp. 4575-4581.
Nelson, et al.; "Non-Human Primates: Model Animals for Developmental Psychopathology"; Neuropsychopharmacology; vol. 34, No. 1, pp. 90-105 (Jan. 2009).
Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Palu, et al.; "In pursuit of new developments for gene therapy of human diseases"; Journal of Biotechnology; vol. 68, pp. 1-13 (1999).
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pandya, et al.; "Where in the Brain Is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.11.I-9.11.I8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Pfeifer, et al.; "Gene Therapy: Promises and Problems"; Annu. Rev. Genomics Hum. Genet.; vol. 2, pp. 177-211 (2001).
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Powell, et al.; "Schizophrenia-Relevant Behavioral Testing in Rodent Models: A Uniquely Human Disorder?"; Biol. Psychiatry; vol. 59, pp. 1198-1207 (2006).
Qiu et al. "Induction of photosensitivity by heterologous expression of melanopsin", Nature, 2005, vol. 433: pp. 745-749.
Racaniello; "How many viruses on Earth?"; Virology Blog; 6 pages; http://www.virology.ws/2013/09/06/how-many-viruses-on-earth/ (Sep. 6, 2013).
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl- cotransporter KCC2 and Impairs Neuronal Cl-Extrusion", The Journal of Cell Biology, 2002, vol. 159: pp. 747-752.
Rogers, et al.; "Effects of ventral and dorsal CA1 subregional lesions on trace fear conditioning"; Neurobiology of Learning and Memory; vol. 86, pp. 72-81 (2006).
Rosenkranz, et al. "The prefrontal cortex regulates lateral amygdala neuronal plasticity and responses to previously conditioned stimuli", J. Neurosci., 2003, vol. 23, No. 35: pp. 11054-11064.

(56) References Cited

OTHER PUBLICATIONS

Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depression," Neuropsychopharmacology, 2008,vol. 33, pp. 368-377.
Schroll et al., "Light-induced activation of distinct modulatory neurons triggers appetitive or aversive learning in *Drosophila* larvae", Current Biology, Sep. 2006, 16(17):1741-1747.
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Shimizu, et al.; "NMDA Receptor-Dependent Synaptic Reinforcement as a Crucial Process for Memory Consolidation"; Science; vol. 290, pp. 1170-1174 (Nov. 10, 2000).
Shoji, et al.; "Current Status of Delivery Systems to Improve Target Efficacy of Oligonucleotides"; Current Pharmaceutical Design; vol. 10, pp. 785-796 (2004).
Sigmund; "Viewpoint: Are Studies in Genetically Altered Mice Out of Control?"; Arterioscler Thromb Vasc Biol.; vol. 20, No. 6, pp. 1425-1429 (Jun. 2000).
Silver, et al. "Amino terminus of the yeast *GAL4* gene product is sufficient for nuclear localization" PNAS, 1984, vol. 81, No. 19: pp. 5951-5955.

Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Sineshchekov et al.; "Intramolecular Proton Transfer in Channelrhodopsins"; Biophysical Journal; vol. 104, No. 4, pp. 807-817 (Feb. 2013).
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sofuoglu, et al.; "Cholinergic Functioning in Stimulant Addiction: Implications for Medications Development"; CNS Drugs; vol. 23, No. 11, pp. 939-952 (Nov. 1, 2009).
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet, 1992, vol. 8, No. 12: pp. 432-439.
Stockklausner et al. "A sequence motif responsible for ER export and surface expression of Kir2.0 inward rectifier K+0 channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.

(56) References Cited

OTHER PUBLICATIONS

Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tsuchida; "Nervous Control of Micturition"; The Japanese Journal of Urology; vol. 80, No. 9, pp. 1257-1277 (1989).
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Uniprot Accession No. P02945, integrated into the database on Jul. 21, 1986.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al."Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonic. 2. Chloride Release and Uptake, Protein Conformation Change, and Thermodynamics", Biochemistry (1995), 34(44):14500-14507.
Verma, et al.; "Gene therapy—promises, problems and prospects"; Nature; vol. 389, pp. 239-242 (Sep. 1997).
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.I-19.39.

Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Wang, et al.; "Simultaneous phase and size control of upconversion nanocrystals through lanthanide doping"; Nature; vol. 463, No. 7284, pp. 1061-1065 (Feb. 25, 2010).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Witten et. al., "Cholinergic Interneurons Control Local Circuit Activity and Cocaine Conditioning", Science, 2010, vol. 330, No. 6011: pp. 1677-1681.
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Witten et. al., Supporting Online Material for: "Cholinergic Interneurons Control Local Circuit Activity and Cocaine Conditioning", Science, 2010, vol. 330:17 pages.
Written opinion of PCT Application No. PCT/US2011/059383 (May 9, 2012).
Xiong et al., "Interregional connectivity to primary motor cortex revealed using MRI resting state images", Hum Brain Mapp, 1999, 8(2-3):151-156.
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.

(56) References Cited

OTHER PUBLICATIONS

Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zeng, et al.; "Activation of acid-sensing ion channels by localized proton transient reveals their role in proton signaling"; Scientific Reports; vol. 5, 14 pages. (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Zhang "Multimodal fast optical interrogation of neural circuitry," Nature, 2007, vol. 446, pp. 633-641.
Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008, vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).

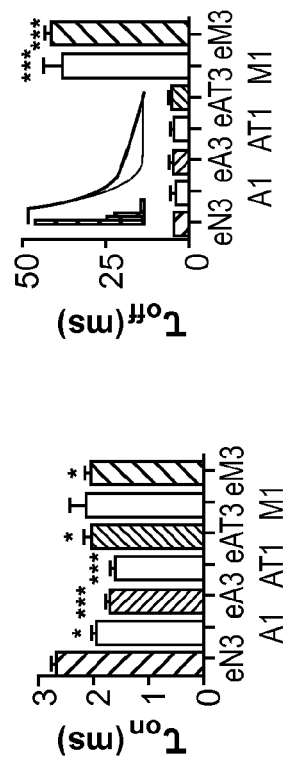
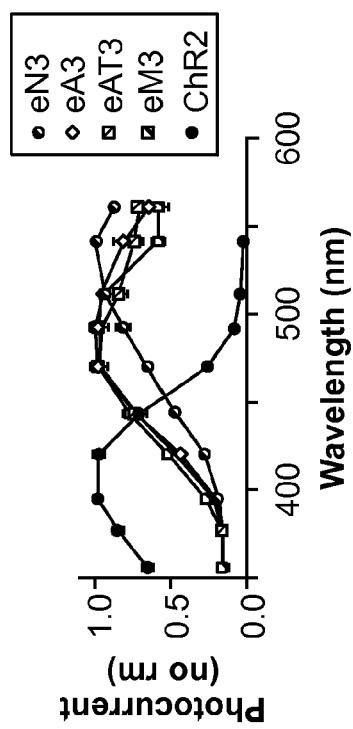
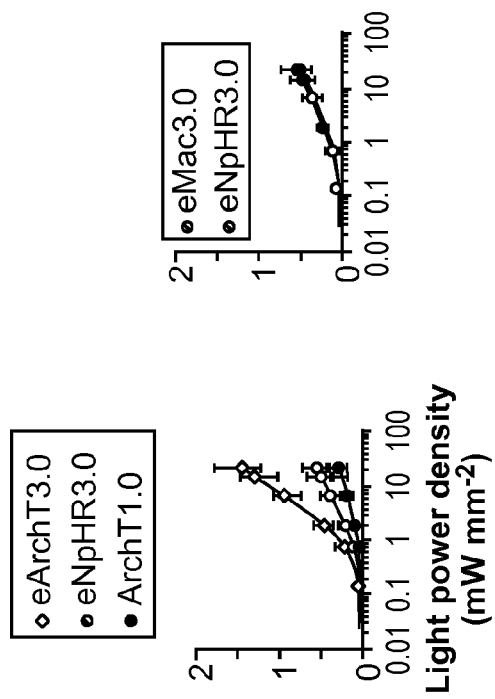
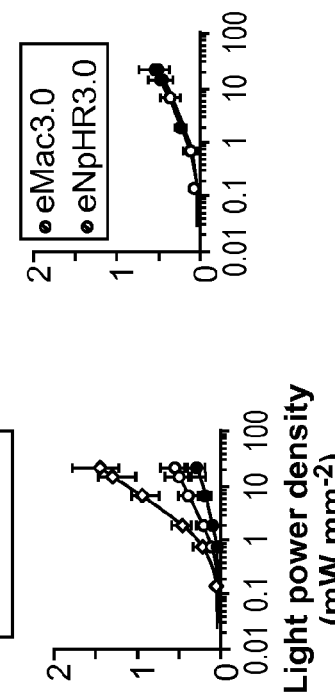
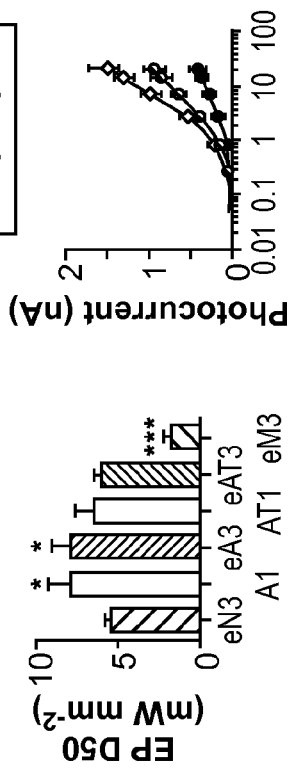
FIG. 1D
FIG. 1E
FIG. 1F

FIG. 2A
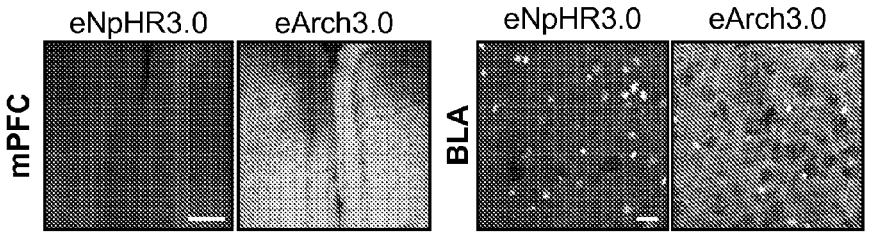
FIG. 2B    FIG. 2C    FIG. 2D
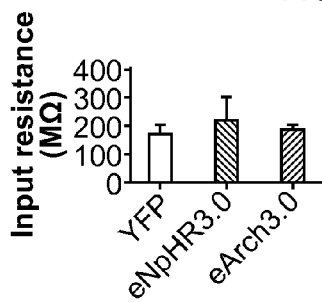 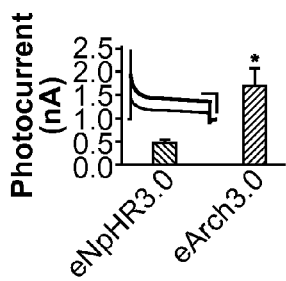 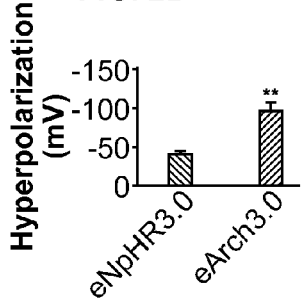
FIG. 2E
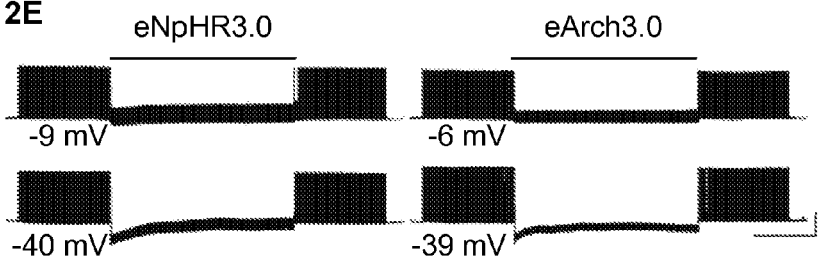
FIG. 2F
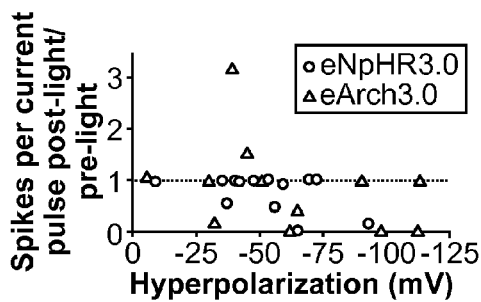 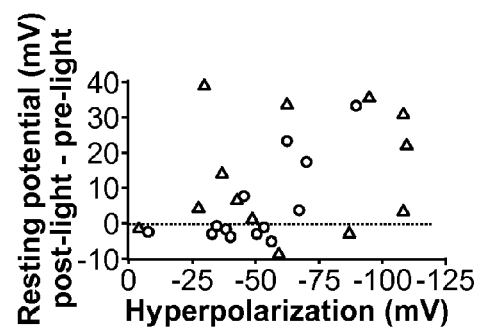

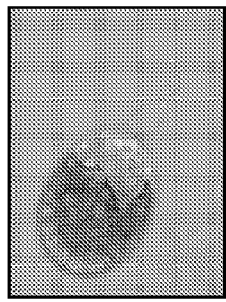
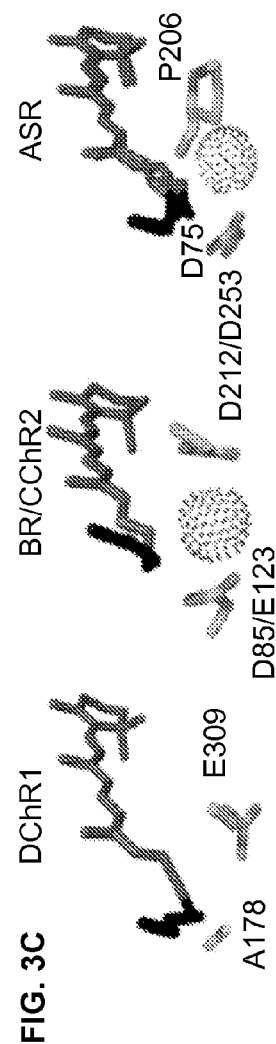
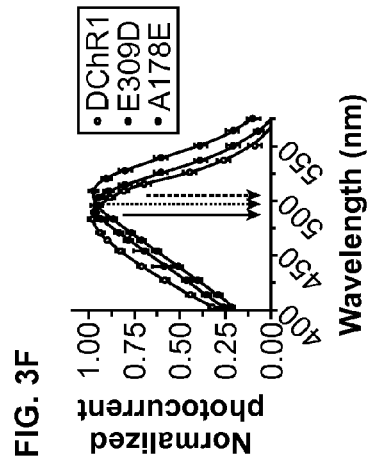
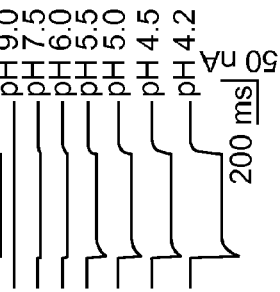
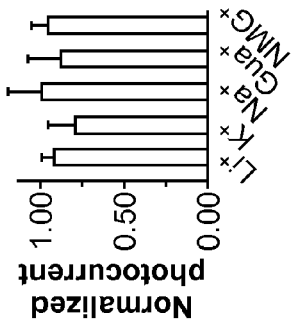
FIG. 3A
FIG. 3B
FIG. 3C
FIG. 3D
FIG. 3E
FIG. 3F > Dunaliella salina Channelrhodopsin-1 (DChR1)
ATGAGGCGACGCGAAAGCCAGCTTGCGTACCTGTCTGTTTGTGCTCATTGCGGCTGGGCACC
TCGACTGACGGAATCGCTCCAGACTTGGCTGAGAGCGCCCACCCTCGAGCCGCAACACCCT
ACGCCAACATCAAAAAGGTTCCGAACATCACTGAGCCAAATGCAAACGTGCAGCTGATGGGTGG
GCTCTGTACCAGGACTTTTATTACCTCCGCGGACAGTGACAAGGAGTGGGTCGTGGGCCCTTCAGA
CCAATGCTACTGCAGGGCCTGGTCTAAGAGCTCATTGTGCCAGTCTGGTATATTCATGTTTGCAGCATGG
TCTGGGCGTACATTGTGTTCGCCATTCGGCTAAGAGCCATCGTTAACATTGTTGAGTTGTGCACATTGCCCTGGT
AAGGCCACAGTCGGCTGGGAGCTCGACAAGCCGGCCATGCTACTGTCCGAGCTGACCAGAGCATGGTCTCGCCT
TGCGCTACTCTGCCTGCTTCTCTGAACAAGCGCACACATGGGCCTCCTGGTTTCTGATATCGTCCAACTTGACAGG
TTGAAGGCGATTACAGCAAGCGCCTGGCCCACCCAACCATGCCTTAAGGTTATTTTGTTCATCATCGGTCTTC
TGAACATCGCAGCGCTGCGCCAGCTTCACTTTCTTGTCCGGAACCTTGTGCCGCGCAATGGTCATGGACCTACTTTGTGAGCTGGACATTG
AAGGCGCAATGCCGGAACCCTTGTGCCGCGAAGGGTTTGGCCACACATCACATATTTTGGATCCAGCATTG
CCCATTCTTTCATCCTGAAATCTTCTCCAAGAACTTCTGGTTGCACCCGTCTCCGTTACGGACCTTCATCCTTGAAATCTTCTCCAAGAACTTGTGGTCAACTTGTGGTCTCCGTTAC
GCCACTTCATCCTTGAAATCTTCTCCAAGAACTTCTGGTTGCACCCGTCTCCGTTAC
AGGATCCGCCAGCACATCATCCATGCAACCTGATTCCAACGACAAGGACTCCGATGTCATTAACAACG
TGACAATGTGGAGGTGGAGGTACGTGGACTCCTTCATGGTCGTGGATTCCAACAGGCACTCCTTCATGGT
GCACCAAGGAGTTTTCCAACAGGCACTCCTTCATGGTCTGATGGCACTTCATGGATCGTATGCAAAAGAACGGC
ACTCAAAACGCGCGTCCCCTCGAGGAGGGCAGCGCATGCGACACGTTGGAGGACGATGTGCCCAGTTCAAAGG
GGGCAAGCTGACACGTGGACAGTGGCATGGACGGCATGCGACACGTTGGAGGACGATGTGCCCAGTGTGCTTGTG
GAGGACTGAGTGAGCATGGAGTTCTTCAGGCAGCAGTTCTCCTTCCTGCCGCAGCAGGGCCTGCAGCTGGGAG
GTGCCAGACATGGAGTTCCCGACCAGGTGTCGCCGACCAGGGCTGTGCAGCAGGGCCTGCAGCTGGGAG
GGTGTATCCCGCCATTGACTTTGTGCCTGGTGCTGGCCGACTTCCTGCACAACCCAGCCCTCTGC
GCACCCCCTACTTGACTTTGACTTGTGCCTGGTGCTGGCCGACTTCCTGCACAACCCAGCCCTCTGC
CTGGTAGCCCGCCTGAAGATGATGGCCATGCCGTGTGCCGCCATTTGCTGCAGCCCCAGGGTCC
CCAGCGGGAACTCATCGAGTCTTCTGGTGTCAGCTCATCGCGCGCCATGCGCCTGCAGCCCCACCAGG
GCATCCACCGCGGGCAGTTTGTGCAGCTCATCGCGCGCGCCATGCGCCTGCAGCCCCACCACC
ACACAGAACATGGCGGCCATGAACATGAACATGCCTCCTGTGCCAGCCATGCCCCCGGCA
CATGGGAAGCTTGGGGGCCATGCCTGTGCAGCCCCAGCCCATGGGTGCAGCCCCCGGCA
TGTACGGCTCCACCATGGCCCCGGTTGTGCAGCCCATGCAGCCCTAATCCCCTGTTCAATGCTCCTCCC
TCTCCCATGGGTAGCCAGCCCGGCATGATGATGGGAACTGCCAGCCCTGCGCCAGCCGCAAGGCAG
CATGCAGGGTGCGCTGCGCGTCCCCGCCAGCCCTGCGCCCGCATGCCAGCCGCCCCGCCCCGG
GAGGTGCTGATGGGGAGGCGCAGAGATGCAGCAGCTGAGGCTGAGATCAACCAGTGCGTGCA
GAGCTCAACCAGAACTAA

FIG. 4

>Dunaliella salina Channelrhodopsin-1 (DChR1), codon-optimized for
mammalian expression
ATGGCGTAGAAGGGAGTCTCAGCTCGCATACCTTTGCCCTGTTCGTTTTGATCGCTGGCTGGCCCC
ACGTCTGACTGAAAGCGCCCCTGATCTAGCCGGCGGCCTCCCTCCGAGCGAACTGCGAAACACCCTT
ACGCCAATATTAAAAGGTGCCCAATATAACTGAACCGCCAACGCCAATGTGCAACTTGATGGGTGG
GCTCTGTACCAGGATTTTACTACCTGGCTGGTTCAGATAAGGAATGGGTCGTTGGCCCTAGCGA
CCAGTGTTACTGCCGAGCATGGTCTAAATCACACGGCACCGACACAGAGAGGGCGAGGCGCTGTGG
TGTGGGCGTACATTCGTATTCGCCATTTGTATCGTACAACTGGTTTATTTCATGTTTGCCGTTGG
AAGGCAACGGTCGGATGGGAGGAAGTCTACGTGAACATCATTGAGCTGGTGCACATTGGTTCCATGGT
GATTTGGGTCGAGTTCGATAAACCCGCCATGCCCTTCCTGCCCAGTCATCCTAATTCACCTGAGCAACTTAACAGGG
CTAAAGGGGACTATAGTAAGAGAACCATGGGGCTTTTGGTCTCTGACATCGGAACCATAGTGTT
TGGTACAAGCCGCCACTCGCTCCCGCCAAACCATGTCAAAGTCATCTTATTTACAATTGGGTTGC
TGTATGGACTCTTCACTTTTTTCACGGCAGGCTATGGCCTTATTCGTAAGTTGGCGATGTT
AAAGGCCAATGTAGAAACCTCGTGGAAGAGAGGGTTTGGCCATATTACATATTTTGCTCATCATCG
CCCCATCCGTTTATCCTGGAGATATTTCAAAAAATCTGTGGAGTCTACTGGGCCACGGATTACGGTAT
GACACTTCATACTGAGCAGCATATCATTCATTCATGCAATTGACAAAGAAGAATAAGATTAATATCGCAGG
CGCATAAGGCAGCAGCATATCATTCATTCATGCAATTGACAAAGAAGAATAAGATTAATATCGCAGG
GGACAACGTCGAAGTGGAAGAGTACGTGGATTCTAACGACAAGGACACAGGCGACGTT

FIG. 5

Dunaliella salina Channelrhodopsin-1 (DChR1)

MRRRESQLAYLCLFVLIAGWAPRLTESAPDLAERRPPSERNTPYANIKKVPNITEPNANV
QLDGWALYQDFYYLAGSDKEWVVGPSDQCYCRAWSKSHGTDREGEAAVVWAYIVFAICIV
QLVYFMFAAWKATVGWEEVYVNIIELVHIALVIWVEFDKPAMLYLNDGQMVPWLRYSAWL
LSCPVILIHLSNLTGLKGDYSKRTMGLLVSDIGTIVFGTSAALAPPNHVKVILFIIGLLY
GLFTFFTAAKVYIEAYHTVPKGQCRNLVRAMAWTYFVSWAMFPILFILGREGFGHITYFG
SSIGHFILEIFSKNLWSLLGHGLRYRIRQHIIHGNLTKKNKINIAGDNVEVEEYVDSND
KDSDVINNGTKEFSNRHSFMVMKDRMQKNGTQTRASLEGEAPPDEEMPSGKKGKLDTLEE
GSDSLEDDVPSSKGGLSGMGDGMPTLQPGRVVLVVPDMELVEFFRQQFSFLPVPFEVYP
AIGADQGVQLAQQGLQLGGTPYLDFVLVAPDFLHNRSPSGLVARLKMMGMRVCAFGWQPQ
GPQRELIESSGVDGFLMGPIHPQGIHRGQFVQLIARMQALKRMPTTQNMGGMNMGMGSMA
GMGMGMGSLGGMPPVAPMGSMGGSPGMYGSTMPRGAAPAPNPLFNAPPSPMGSQPGMM
MGGAAGMQPQGSMQGGAASPHGTASPAPPAPGGADGEAQMMQQLMAEINQLRAELNQN

FIG. 6

Opsin  TS  *YFP*  ER eArch-eYFP 2.0:

mdpialqagydlllgdgrpetlwlgigtllmligtfyflvrgwgvtdkdareyyavtilvpgiasaaylsmffgigltevtvggemldiyyaryadwlfttp
llllldlallakvdrvtigtlvgvdalmivtgligalshtaiaryswwlfsticmivvlvflatslrsaakergpevastfntltalvlvlwtaypilwiigtegag
vvglgietllfmvldvtakvgfgfillrsrailgdteapepsagadvsaadrpvvavskaaavskgeeftgvpilveldgdvnghkfsvsgegegdaty
gkltlkfjcittgklpvpwptlvtfgyglqcfarypdhmkqhdffksampegyvqertffkddgnyktraevkfegdtlvnrielkgidfkedgnilghkle
ynynshnvyimadkqkngikvnfkirhniedgsvqladhyqqntpigdgpvllpdnhylsyqsalskdpnekrdhmvllefvtaagitlgmdelykfc
yenev eArch-eYFP 3.0:

mdpialqagydlllgdgrpetlwlgigtllmligtfyflvrgwgvtdkdareyyavtilvpgiasaaylsmffgigltevtvggemldiyyaryadwlfttp
llllldlallakvdrvtigtlvgvdalmivtgligalshtaiaryswwlfsticmivvlvflatslrsaakergpevastfntltalvlvlwtaypilwiigtegag
vvglgietllfmvldvtakvgfgfillrsrailgdteapepsagadvsaadrpvvavskaaaksritsegeyipldqidinvskgeeftgvpilveldgd
vnghkfsvsgegegdatygkltlkfjcittgklpvpwptlvtfgyglqcfarypdhmkqhdffksampegyvqertffkddgnyktraevkfegdtlvnri
elkgidfkedgnilghkleynynshnvyimadkqkngikvnfkirhniedgsvqladhyqqntpigdgpvllpdnhylsyqsalskdpnekrdhmvll
efvtaagitlgmdelykfcyenev eArchT-eYFP 3.0:

mdpialqagydlllgdgrpetlwlgigtllmligtfyflvkgwgvtdkeareyysitilvpgiasaaylsmffgigltevtvagevldiyyaryadwlfttpl
llldlallakvdrvsigtlvgvdalmivtgligalshtplaryswwlfsticmivvlvflatslraaakergpevastfntltalvlvlwtaypilwiigtegag
vvglgietllfmvldvtakvgfgfillrsrailgdteapepaaaksritsegeyipldqidinvskgeeftgvpilveldgdvnghkfsvsgegegdaty
gkltlkfjcittgklpvpwptlvtfgyglqcfarypdhmkqhdffksampegyvqertffkddgnyktraevkfegdtlvnrielkgidfkedgnilghkle
ynynshnvyimadkqkngikvnfkirhniedgsvqladhyqqntpigdgpvllpdnhylsyqsalskdpnekrdhmvllefvtaagitlgmdelykfc
yenev

FIG. 7C eMac-eYFP 2.0:

mivdqfeevlmktsqlfplptatqsaqpthvapvptvlpdtpiyetvgdsgsktlwvvfvlmliasaaftalswkipvnrrlyhvittiitltaalsyfama
tghgvalnkivirtqhdhvpdtyetvvrqvyyaryidwaittplllldlglagmsgahifmaivadlimvltglfaafgsegtpqkwgwytiaciayifv
vwhlvlngganarvkgeklrsffvaigaytlilwtaypivwgladgarkigvdgeiiayavldvlakgvfgawllvthanlresdvelngfwanglnre
gairigeddgarpvvavskaaavskgeelftgvvpilveldgdvnghkfsvsgegegdatygkltlkfjcttgklpvpwptlvttfgyglqgfarypdhmk
qhdffksampegyvvqertiffkadgnyktraevkfegdtlvnrielkgidfkedgnilghkleynynshnvyimadkqkngikvnfkirhniedgsvqla
dhyqqntpigdgpvllpdnhylsyqsalskdpnekrdhmvllefvtaagitlgmdelykfcyenev

FIG. 7D eMac-eYFP 3.0:

mivdqfeevlmktsqlfplptatqsaqpthvapvptvlpdtpiyetvgdssgsktlwvvfvlmliasaaftalswkipvnrrlyhvittiitltaalsyfama
tghgvalnkivirtqhdhvpdtyetvvrqvyyaryidwaittplllldlglagmsgahifmaivadlimvltglfaafgsegtpqkwgwytiaciayifv
vwhlvlngganarvkgeklrsffvaigaytlilwtaypivwgladgarkigvdgeiiayavldvlakgvfgawllvthanlresdvelngfwanglnre
gairigeddgarpvvavskaaaksritsegeyiplqidinvskgeelftgvvpilveldgdvnghkfsvsgegegdatygkltlkfjcttgklpvpwptlv
ttfgyglqcfarypdhmkqhdffksampegyvqertiffkadgnyktraevkfegdtlvnrielkgidfkedgnilghkleynynshnvyimadkqkngi
kvnfkirhniedgsvqladlhyqqntpigdgpvllpdnhylsyqsalskdpnekrdhmvllefvtaagitlgmdelykfcyenev

FIG. 7E

GenBank BAA09452
*Halorubrum sodomense* archaerhodopsin-3

```
  1 mdpialqagy dllgqdgrpet lwlgigtllm ligtfyflvr gwgvtdkdar eyyavtilvp
 61 giasaaylsm ffgigltevt vggemldiyy aryadwlftt plildlall akvdrvtigt
121 lvgvdalmiv tgligalsht aiaryswwlf sticmivvly flatslrsaa kergpevast
181 fntltalvlv lwtaypilwi igtegagvvg lgietllfmv ldvtakvgfg fillrsrail
241 gdteapepsa gadvsaad
```

FIG. 8A

GenBank D50848
*Halorubrum sodomense* archaerhodopsin-3 coding sequence

```
  1 ctgggttggc atcggtctca atagagtata tactgtatca ggatgtgggt atggacccga
 61 tagcactaca ggcgggatac gacctactcg gggacggtcg cccgagacg ttgtggttgg
121 gtatcggaac gttactaatg ctcatcggga cctctactt cctcgtcaga gggtgggggg
181 tcaccgacaa ggacgcccgc gagtactacg cggtcacgat cctcgtgccg gggatcgcgt
241 cggcggcgta cctgtcgatg ttcttcggca tcggcctgac ggaagtcacg gtcggtggcg
301 aaatgctcga catctactac gcgcgtacg cggactggct gttcaccacg cgctgctgc
361 tgctcgacct cgcgctgctc gcaaaggtcg accggcgtcac catcgggacg ctcgcacacg
421 tcgacgcgct gatgatcgtc accggcctca tcgggcgct cgtgctgtac gcgatcgcgc
481 ggtactcctg gtggctgttc agcacgattt gcatgatcgt cgtgctgtac ttcctcgcca
541 cgagcctccg gagcgcggcg aaggagcgcg gacctgaagt cgcgagcacc ttcaacacgt
601 tgaccgcgct ggtcctggtg ctctggacgg cctacccgat cctgtggatc atcggaaccg
661 agggcgccgg cgtcgtcggc ctcgtcggc agacctct gttcatggtt ctcgacgtga
721 cggccaaggt cggcttcggc ttcatcctgc tccgcagccg cgccatcctc ggcgacaccg
781 agggcccgga gccctccgcg ggcgccgacg tctccgccgc ggactgatcg gctagcggac
841 ccagcgaaac tgaacagcgc gcgaacgact ttcacaaacc attcttcaca tgagcgctac
901 gaacaccgaa cagccggcag tgctgaatac gcggtccgtc gtcgggct
```

FIG. 8B

GenBank GU045593
*Halorubrum sodomense* archaerhodopsin-3 coding sequence; codon optimized for mammalian expression

```
  1  atggacccca tcgctctgca ggctggttac gacctgctgg gtgacggcag acctgaaact
 61  ctgtggctgg gcatcggcac tctgctgatg ctgattggaa ccttctactt tctggtccgc
121  ggatggggag tcaccgataa ggatgcccgg aatattacg ctgtgactat cctggtgccc
181  ggaatcgcat ccgccgcata tctgtctatg ttctttggta tcgggcttac tgaggtgacc
241  gtcggggcg aaatgttgga tatctattat gccaggtacg ccgactggct gtttaccacc
301  ccacttctgc tgctggatct ggcccttctc gctaaggtgg atcgggtgac catcggcacc
361  ctggtgggtg tggacgccct gatgatcgtc actggcctca tcgagcct gagccacacg
421  gccatagcca gatacagttg gtggttgttc tctacaattt gcatgatagt ggtgctctat
481  tttctggcta catccctgcg atctgctgca aaggagcggg gccccgaggt ggcatctacc
541  tttaacaccc tgacagctct ggtcttggtg ctgtggaccg cttaccctat cctgtggatc
601  ataggcactg agggcctgg cgtggtgggc ctgggcatcg aaactctgct gtttatggtg
661  ttgacgtga ctgccaaggt cggctttggc tttatcctgt tgagatcccg ggctattctg
721  ggcgacaccg aggcaccaga acccagtgcc ggtgccgatg tcagtgccgc cgactaa
```

FIG. 8C

GenBank ABT17417.1
*Halorubrum sodomense* strain TP009 opsin

```
  1 mdpialqagy dllgdgrpet lwlgigtllm ligtfyfivk gwgvtdkear eyysitilvp
 61 giasaaylsm ffgigltevt vagevldiyy aryadwlftt pllldlall akvdrvsigt
121 lvgvdalmiv tgligalsht plaryswwlf sticmivvly flatslraaa kergpevast
181 fntltalvlv lwtaypilwi igtegagvvg lgietllfmv ldvtakvgfg fillrsrail
241 gdteapepsa gaeasaad
```

FIG. 9A

GenBank EF558549
*Halorubrum sodomense* strain TP009 opsin coding sequence

```
  1 tcagtcccgc gcgagggcct cagcgcccgc ggagggctcc gggcctcgg tgtcgccgag
 61 gatcgcgcgg ctgcggagca ggatgaagcc gaagccgacc ttggcggtca cgtcgagaac
121 catgaacagg agggtctcga tgccgaggcc gacgacgccg gctccctcag taccgatgat
181 ccagaacagg gggtacgcgg tccagaggac gagcaccaac gcggtcagcg tgttgaacgt
241 gctcgcgact tcggggccgc gctccttcgc cgcggcgcgc aggctcgtgg cgaggaagta
301 cagcacgacg atcatgcaga tcgtgctgaa cagccaccag gagtaccgcg cgagcgggcg
361 gtgcgagagc gcgccgatga ggccggtcga cccttcgcca gcagccgagg cgtcgacgc cgacgagcgt
421 cccgatgctc acgcggtcga cctgcgccag cagccggagg tcgagcagca gcagcgggcgt
481 ggtgaacagc cagtccgcgt accgcgcgta gtagatgtcg agcacttctc cggccgaccgt
541 gacttccgtc aggccgattc cgaagaacat cgacaggtac gccgccgacg cgatcccccgg
601 cacgaggatc gtaatcgagt agtactcacg ggcctccttg tcggtgaccc cccatccttt
661 gacgatgaag tagaaggtcc cgatgagcat tagtagcgtg cctataccca accaaagcgt
721 ctcgggacgt ccgtccccga gcaggtcgta tcccgcctgt agcgctatcg ggtccat
```

FIG. 9B

GenBank AAG01180
*Leptosphaeria maculans* opsin

```
  1 mivdqfeevl mktsqlfplp tatqsaqpth vapvptvlpd tpiyetvgds gsktlwvvfv
 61 lmliasaaft alswkipvnr rlyhvittii tltaalsyfa matghgvaln kivirtqhdh
121 vpdtyetvyr qvyyaryidw aittplllld lgllagmsga hifmaivadl imvltglfaa
181 fgsegtpqkw gwytiaciay ifvvwhlvln gganarvkge klrsffvaig aytlilwtay
241 pivwgladga rkigvdgeii ayavldvlak gvfgawllvt hanlresdve lngfwangln
301 regairiged dga
```

FIG. 10A

GenBank AF290180

*Leptosphaeria maculans* opsin coding sequence

```
  1 atgattgttg accaattcga ggaagtcctg atgaagacgt cacagctctt cccgctgccg
 61 acggccaccc aatcggccca gcctacccat gtggcgcctg tgcccacggt cctaccagac
121 actcccatct acgagacggt cggcgattcc ggcagcaaga cgctctgggt ggtcttcgtg
181 ctcatgctga ttgcctctgc tgctttcact gccttgtcat ggaagatccc agttaacagg
241 cgtttgtacc atgtcatcac gacaatcatc acgttgactg ctgctctttc ttactttgcc
301 atggccactg gccacggcgt tgccctcaac aagattgtca ttcgcactca gcatgaccat
361 gtccccgaca cgtacgagac cgtataccgc caggtctact atgctcgtta cattgactgg
421 gccatcacca ctcctcttct gctcctcgat cttggtctcc tggctggcat gtccggtgcc
481 cacatcttca tggccattgt cgctgatttg atcatggtct tgactggtct cttcgctgcc
541 ttcggttccg agggcactcc ccagaagtgg ggctggtaca ctattgcctg cattgcctac
601 atcttcgttg tctggcacct ggtcctgaac ggaggtgcca acgccagggt caagggcgag
661 aagctccgat ctttctttgt tgccattggt gcctacactc tgattctttg gaccgcctat
721 cccattgttt ggggtctagc agatggtgcc cgcaagatcg gtgttgacgg tgagatcatt
781 gcctacgccg ttcttgacgt ccttgccaag ggtgtctttg gtgcatggct tctagtcacc
841 cacgccaatc ttcgtgagag cgatgttgag ctcaacggct tctgggccaa cggcctcaac
901 cgtgagggtg ctattcgcat tggtgaggat gacggtgctt aa
```

FIG. 10B

GenBank
*Leptosphaeria maculans* opsin coding sequence; codon optimized for mammalian expression

```
  1 atgatcgtgg accagttcga ggaggtgctg atgaagacca gccagctgtt cccactgcca
 61 accgctaccc agagcgccca gccaacccac gtggcccccg tgccaaccgt gctgcccgac
121 acccccatct acgagaccgt gggcgacagc ggcagcaaga ccctgtgggt ggtgttcgtg
181 ctgatgctga tcgccagcgc cgccttcacc gccctgagct ggaagatccc cgtgaacagg
241 aggctgtacc acgtgatcac caccatcatc accctgaccg ccgccctgag ctacttcgct
301 atggctaccg gccacggagt ggccctgaac aagatcgtga tcaggaccca gcacgaccac
361 gtgcccgaca cctacgagac cgtgtaccga caggtgtact acgccaggta catcgactgg
421 gctatcacca ccccactgct gctgctggac ctgggactgc tggctggaat gagcggagcc
481 cacatcttca tggccatcgt ggctgacctg atcatggtgc tgaccggcct gttcgctgct
541 ttcggcagcg agggaacccc acagaagtgg ggatggtaca ccatcgcctg catcgcctac
601 atcttcgtgg tgtggcacct ggtgctgaac ggcggcgcca acgccagggt gaagggcgag
661 aagctgagga gcttcttcgt ggccatcgga gcttacaccc tgatcctgtg gaccgcttac
721 ccaatcgtgt ggggactggc tgacggagct aggaagatcg gagtggacgg agagatcatc
781 gcttacgctg tgctggacgt gctggctaag ggagtgttcg gagcttggct gctggtgacc
841 cacgccaacc tgagggagag cgacgtggag ctgaacggct tctgggccaa cggcctgaac
901 agggagggcg ccatcaggat cggcgaggac gacggcgcct aa
```

FIG. 10C

SEQUENCE LISTING

<160> NUMBER OF SEQ ID NOS: 35

<210> SEQ ID NO 1
<211> LENGTH: 5
<212> TYPE: PRT
<213> ORGANISM: Artificial sequence
<220> FEATURE:
<223> OTHER INFORMATION: Synthetic sequence

<400> SEQUENCE: 1

Val Lys Glu Ser Leu
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic sequence

<400> SEQUENCE: 2

Val Leu Gly Ser Leu
1               5

```
<210> SEQ ID NO 3
<211> LENGTH: 16
<212> TYPE: PRT
<213> ORGANISM: Artificial sequence
<220> FEATURE:
<223> OTHER INFORMATION: Synthetic sequence

<400> SEQUENCE: 3

Asn Ala Asn Ser Phe Cys Tyr Glu Asn Glu Val Ala Leu Thr Ser Lys
1               5                   10                  15

<210> SEQ ID NO 4
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 4

Phe Xaa Tyr Glu Asn Glu
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic sequence

<400> SEQUENCE: 5

Phe Cys Tyr Glu Asn Glu Val
1               5

<210> SEQ ID NO 6
<211> LENGTH: 26
<212> TYPE: PRT
<213> ORGANISM: Artificial sequence
<220> FEATURE:
<223> OTHER INFORMATION: Synthetic sequence

<400> SEQUENCE: 6

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 7
<211> LENGTH: 27
<212> TYPE: PRT
<213> ORGANISM: Artificial sequence
<220> FEATURE:
<223> OTHER INFORMATION: Synthetic sequence

<400> SEQUENCE: 7

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 8
<211> LENGTH: 23
```

```
<212> TYPE: PRT
<213> ORGANISM: Artificial sequence
<220> FEATURE:
<223> OTHER INFORMATION: Synthetic sequence

<400> SEQUENCE: 8

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 9
<211> LENGTH: 18
<212> TYPE: PRT
<213> ORGANISM: Artificial sequence
<220> FEATURE:
<223> OTHER INFORMATION: Synthetic sequence

<400> SEQUENCE: 9

Met Arg Gly Thr Pro Leu Leu Leu Val Val Ser Leu Phe Ser Leu Leu
1               5                   10                  15

Gln Asp

<210> SEQ ID NO 10
<211> LENGTH: 20
<212> TYPE: PRT
<213> ORGANISM: Artificial sequence
<220> FEATURE:
<223> OTHER INFORMATION: Synthetic sequence

<400> SEQUENCE: 10

Lys Ser Arg Ile Thr Ser Glu Gly Glu Tyr Ile Pro Leu Asp Gln Ile
1               5                   10                  15

Asp Ile Asn Val
            20

<210> SEQ ID NO 11
<211> LENGTH: 35
<212> TYPE: DNA
<213> ORGANISM: Artificial sequence
<220> FEATURE:
<223> OTHER INFORMATION: Synthetic sequence

<400> SEQUENCE: 11
gtggcgcgcc ctattacttg tacagctcgt ccatg                          35

<210> SEQ ID NO 12
<211> LENGTH: 30
<212> TYPE: DNA
<213> ORGANISM: Artificial sequence
<220> FEATURE:
<223> OTHER INFORMATION: Synthetic sequence

<400> SEQUENCE: 12
tatgctagcc accatggact atggcggcgc                                30

<210> SEQ ID NO 13
<211> LENGTH: 36
<212> TYPE: DNA
<213> ORGANISM: Artificial sequence
<220> FEATURE:
<223> OTHER INFORMATION: Synthetic sequence

<400> SEQUENCE: 13
gttatgctag cgccaccatg tcgcggaggc catggc                         36
```

<210> SEQ ID NO 14
<211> LENGTH: 4
<212> TYPE: PRT
<213> ORGANISM: Artificial sequence
<220> FEATURE:
<223> OTHER INFORMATION: Synthetic sequence

<400> SEQUENCE: 14

Lys Asp Glu Leu
1

<210> SEQ ID NO 15
<211> LENGTH: 23
<212> TYPE: PRT
<213> ORGANISM: Dunaliella salina

<400> SEQUENCE: 15

Gln Met Val Pro Trp Leu Arg Tyr Ser Ala Trp Leu Leu Ser Cys Pro
1               5                   10                  15

Val Ile Leu Ile His Leu Ser
            20

<210> SEQ ID NO 16
<211> LENGTH: 23
<212> TYPE: PRT
<213> ORGANISM: Chlamydomonas reinhardtii

<400> SEQUENCE: 16

Asn Lys Thr Val Trp Leu Arg Tyr Ala Glu Trp Leu Leu Thr Cys Pro
1               5                   10                  15

Val Ile Leu Ile His Leu Ser
            20

<210> SEQ ID NO 17
<211> LENGTH: 23
<212> TYPE: PRT
<213> ORGANISM: Chlamydomonas reinhardtii

<400> SEQUENCE: 17

His Arg Val Gln Trp Leu Arg Tyr Ala Glu Trp Leu Leu Thr Cys Pro
1               5                   10                  15

Val Ile Leu Ile His Leu Ser
            20

<210> SEQ ID NO 18
<211> LENGTH: 23
<212> TYPE: PRT
<213> ORGANISM: Volvox carteri

<400> SEQUENCE: 18

Asn Gly Val Val Trp Met Arg Tyr Gly Glu Trp Leu Leu Thr Cys Pro
1               5                   10                  15

Val Leu Leu Ile His Leu Ser
            20

<210> SEQ ID NO 19
<211> LENGTH: 23
<212> TYPE: PRT
<213> ORGANISM: Volvox carteri

<400> SEQUENCE: 19

Asn Arg Val Leu Trp Leu Arg Tyr Gly Glu Trp Leu Leu Thr Cys Pro

```
1               5                  10                 15
Val Ile Leu Ile His Leu Ser
          20

<210> SEQ ID NO 20
<211> LENGTH: 2163
<212> TYPE: DNA
<213> ORGANISM: Dunaliella salina

<400> SEQUENCE: 20
atgaggcgac gcgaaagcca gcttgcgtac ctgtgtctgt ttgtgctcat tgcgggctgg      60
gcacctcgac tgacggaatc ggctccagac ttggctgaga ggcgcccacc ctcggagcgc     120
aacacaccct acgccaacat caaaaaggtt ccgaacatca ctgagccaaa tgcaaacgtg     180
cagctggatg ggtgggctct gtaccaggac ttttattacc tcgcgggcag tgacaaggag     240
tgggtcgtgg cccttcaga ccaatgctac tgcagggcct ggtctaagag tcatggcact      300
gacagagagg gagaagctgc tgtggtctgg cgtacattg tgttcgccat ctgcattgtg      360
cagctggtat atttcatgtt tgcagcatgg aaggccacag tcggctggga ggaggtctac     420
gttaacatta ttgagttggt gcacattgcc ctggtcattt gggtcgagtt cgacaagccg     480
gccatgctgt acttgaatga tggacagatg gtgccttggc tgcgctactc tgcctggctt     540
ctctcatgcc cagtcatcct gatccacttg tccaacttga cagggttgaa gggcgattac     600
agcaagcgca caatgggcct cctggttttct gatatcggaa ccattgtgtt tggaacatcg     660
gcagcgctgg cgccacccaa ccatgttaag gttatttttgt tcatcatcgg tcttctgtac     720
ggcctgttca ctttcttcac agctgcaaag gtgtacattg aggcatacca cacagtgccc     780
aaggggcaat gccggaacct tgtgcgtgcc atggcatgga cctactttgt gagctgggcc     840
atgttcccca ttcttttcat cctgggccgc gaagggtttg gccacatcac atattttgga     900
tccagcattg ccacttcat ccttgaaatc ttctccaaga acttgtggtc actgctgggt      960
cacggtctcc gttacaggat ccgccagcac atcatcatcc atggcaacct gaccaagaag    1020
aacaagatca acattgcggg tgacaatgtg gaggtggagg agtacgtgga ttccaacgac    1080
aaggactccg atgtcattaa caacggcacc aaggagtttt ccaacaggca ctccttcatg    1140
gtcatgaaag atcgtatgca aagaacggc actcaaacac gcgcgtccct cgagggcgag     1200 gccccctcctg atgaagaaat gcccagcggc aagaagggca agctggacac gttggaggag    1260
ggcagcgaca gcttggagga cgatgtgccc agttcaaagg gaggactgag tggcatgggc    1320
atggacggca tgcccacgct gcagcctggg cgtgtggtgc ttgtggtgcc agacatggag    1380
ctggtggagt tcttcaggca gcagttctcc ttcctacccg tgccctttga ggtgtatccc    1440
gccattggcg ccgaccaggg tgtgcagctg gcgcagcagg gcctgcagct gggaggcacc    1500
ccctacttgg actttgtgct ggtggcccct gacttcctgc acaaccgcag ccctctggc     1560 ctggtagccc gcctgaagat gatgggcatg cgcgtgtgcg catttggctg gcagccccag    1620
ggtccccagc gggaactcat cgagtcttct ggtgtcgacg gcttcctcat gggccccatc    1680
cacccacagg gcatccaccg cgggcagttt gtgcagctca tcgcgcgcat gcaggccctc    1740
aagcgcatgc ccaccacaca gaacatgggc ggcatgaaca tgggcatggg cagcatggca    1800
ggcatgggca tgggcatggg catgggaagc ttgggggcca tgcctcctgt ggcccccatg    1860
ggctccatgg gtgcagccc cggcatgtac ggctccacca tgcccgtgg tgcagcccca     1920 gcccctaatc ccctgttcaa tgctcctccc tctcccatgg gtagccagcc cggcatgatg    1980
```

```
atgggcggtg ctgcgggcat gcagccgcaa ggcagcatgc agggtggcgc tgcgtccccg      2040
catggaactg ccagccctgc gccccctgcc ccgccccggg aggtgctga tggggaggcg       2100 cagatgatgc agcagctgat ggctgagatc aaccagctgc gtgcagagct caaccagaac      2160
taa                                                                    2163
```

<210> SEQ ID NO 21
<211> LENGTH: 1095
<212> TYPE: DNA
<213> ORGANISM: Artificial sequence
<220> FEATURE:
<223> OTHER INFORMATION: Synthetic sequence

<400> SEQUENCE: 21

```
atgcgtagaa gggagtctca gctcgcatac ctttgcctgt tcgttttgat cgctggctgg       60
gccccacgtc tgactgaaag cgcccctgat ctagccgagc ggcggcctcc ctccgagcga      120
aacacccctt acgccaatat taaaaaggtg cccaatataa ctgaacccaa cgccaatgtg      180
caacttgatg ggtgggctct gtaccaggat ttttactacc tggctggttc agataaggaa      240
tgggtcgttg ccctagcga ccagtgttac tgccgagcat ggtctaaatc acacggcacc       300
gacagagagg gcgaggcggc tgtggtgtgg gcgtacatcg tattcgccat ttgtatcgta      360
caactggttt atttcatgtt tgccgcttgg aaggcaacgg tcggatggga ggaagtctac      420
gtgaacatca ttgagctggt gcacattgcc ctggtgattt gggtcgagtt cgataaaccc      480
gccatgctct accttaacga cggtcagatg gttccatggt gcgctatag tgcatggctc       540 ctttcctgcc cagtcatcct aattcacctg agcaacttaa cagggctaaa gggggactat      600
agtaagagaa ccatggggct tttggtctct gacatcggaa ccatagtgtt tggtacaagc      660
gccgcactcg ctccgccaaa ccatgtcaaa gtcatcttat ttacaattgg gttgctgtat      720
ggactcttca cttttttcac ggcagcgaag gtatatattg aggcctacca caccgttcca      780
aaaggccaat gtagaaacct cgtgagggct atggcctgga cttatttcgt aagttgggcg      840
atgttcccca tcctgtttat cctgggaaga gagggttttg gccatattac atattttggc      900
tcatccatcg gacacttcat actggagata ttttcaaaaa atctgtggag tctactgggc      960
cacggattac ggtatcgcat aaggcagcat atcatcattc atggcaattt gacaaagaag     1020
aataagatta tatcgcagg ggacaacgtc gaagtggaag agtacgtgga ttctaacgac     1080
aaggacagcg acgtt                                                      1095
```

<210> SEQ ID NO 22
<211> LENGTH: 720
<212> TYPE: PRT
<213> ORGANISM: Dunaliella salina

<400> SEQUENCE: 22

```
Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
            20                  25                  30

Glu Arg Arg Pro Pro Ser Glu Arg Asn Thr Pro Tyr Ala Asn Ile Lys
        35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80
```

```
Trp Val Val Gly Pro Ser Asp Gln Cys Tyr Cys Arg Ala Trp Ser Lys
                85              90                  95

Ser His Gly Thr Asp Arg Glu Gly Ala Ala Val Val Trp Ala Tyr
            100             105             110

Ile Val Phe Ala Ile Cys Ile Val Gln Leu Val Tyr Phe Met Phe Ala
            115             120             125

Ala Trp Lys Ala Thr Val Gly Trp Glu Glu Val Tyr Val Asn Ile Ile
130             135             140

Glu Leu Val His Ile Ala Leu Val Ile Trp Val Glu Phe Asp Lys Pro
145             150             155             160

Ala Met Leu Tyr Leu Asn Asp Gly Gln Met Val Pro Trp Leu Arg Tyr
                165             170             175

Ser Ala Trp Leu Leu Ser Cys Pro Val Ile Leu Ile His Leu Ser Asn
            180             185             190

Leu Thr Gly Leu Lys Gly Asp Tyr Ser Lys Arg Thr Met Gly Leu Leu
            195             200             205

Val Ser Asp Ile Gly Thr Ile Val Phe Gly Thr Ser Ala Ala Leu Ala
    210             215             220

Pro Pro Asn His Val Lys Val Ile Leu Phe Ile Ile Gly Leu Leu Tyr
225             230             235             240

Gly Leu Phe Thr Phe Phe Thr Ala Ala Lys Val Tyr Ile Glu Ala Tyr
                245             250             255

His Thr Val Pro Lys Gly Gln Cys Arg Asn Leu Val Arg Ala Met Ala
            260             265             270

Trp Thr Tyr Phe Val Ser Trp Ala Met Phe Pro Ile Leu Phe Ile Leu
            275             280             285

Gly Arg Glu Gly Phe Gly His Ile Thr Tyr Phe Gly Ser Ser Ile Gly
    290             295             300

His Phe Ile Leu Glu Ile Phe Ser Lys Asn Leu Trp Ser Leu Leu Gly
305             310             315             320

His Gly Leu Arg Tyr Arg Ile Arg Gln His Ile Ile His Gly Asn
                325             330             335

Leu Thr Lys Lys Asn Lys Ile Asn Ile Ala Gly Asp Asn Val Glu Val
            340             345             350

Glu Glu Tyr Val Asp Ser Asn Asp Lys Asp Ser Asp Val Ile Asn Asn
            355             360             365

Gly Thr Lys Glu Phe Ser Asn Arg His Ser Phe Met Val Met Lys Asp
    370             375             380

Arg Met Gln Lys Asn Gly Thr Gln Thr Arg Ala Ser Leu Glu Gly Glu
385             390             395             400

Ala Pro Pro Asp Glu Glu Met Pro Ser Gly Lys Lys Gly Lys Leu Asp
                405             410             415

Thr Leu Glu Glu Gly Ser Asp Ser Leu Glu Asp Val Pro Ser Ser
            420             425             430

Lys Gly Gly Leu Ser Gly Met Gly Met Asp Gly Met Pro Thr Leu Gln
            435             440             445

Pro Gly Arg Val Val Leu Val Val Pro Asp Met Glu Leu Val Glu Phe
    450             455             460

Phe Arg Gln Gln Phe Ser Phe Leu Pro Val Pro Phe Glu Val Tyr Pro
465             470             475             480

Ala Ile Gly Ala Asp Gln Gly Val Gln Leu Ala Gln Gln Gly Leu Gln
                485             490             495

Leu Gly Gly Thr Pro Tyr Leu Asp Phe Val Leu Val Ala Pro Asp Phe
```

```
                500              505              510
Leu His Asn Arg Ser Pro Ser Gly Leu Val Ala Arg Leu Lys Met Met
            515                  520                  525

Gly Met Arg Val Cys Ala Phe Gly Trp Gln Pro Gln Gly Pro Gln Arg
    530                  535                  540

Glu Leu Ile Glu Ser Ser Gly Val Asp Gly Phe Leu Met Gly Pro Ile
545                  550                  555                  560

His Pro Gln Gly Ile His Arg Gly Gln Phe Val Gln Leu Ile Ala Arg
                565                  570                  575

Met Gln Ala Leu Lys Arg Met Pro Thr Thr Gln Asn Met Gly Gly Met
            580                  585                  590

Asn Met Gly Met Gly Ser Met Ala Gly Met Gly Met Gly Met Gly Met
        595                  600                  605

Gly Ser Leu Gly Gly Met Pro Pro Val Ala Pro Met Gly Ser Met Gly
    610                  615                  620

Gly Ser Pro Gly Met Tyr Gly Ser Thr Met Pro Arg Gly Ala Ala Pro
625                  630                  635                  640

Ala Pro Asn Pro Leu Phe Asn Ala Pro Pro Ser Pro Met Gly Ser Gln
                645                  650                  655

Pro Gly Met Met Met Gly Gly Ala Ala Gly Met Gln Pro Gln Gly Ser
            660                  665                  670

Met Gln Gly Gly Ala Ala Ser Pro His Gly Thr Ala Ser Pro Ala Pro
        675                  680                  685

Pro Ala Pro Ala Pro Gly Gly Ala Asp Gly Glu Ala Gln Met Met Gln
    690                  695                  700

Gln Leu Met Ala Glu Ile Asn Gln Leu Arg Ala Glu Leu Asn Gln Asn
705                  710                  715                  720

<210> SEQ ID NO 23
<211> LENGTH: 514
<212> TYPE: PRT
<213> ORGANISM: Artificial sequence
<220> FEATURE:
<223> OTHER INFORMATION: Synthetic sequence

<400> SEQUENCE: 23

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
```

Phe Leu Ala Thr Ser Leu Arg Ser Ala Ala Lys Glu Arg Gly Pro Glu
145                 150                 155                 160

Val Ala Ser Thr Phe Asn Thr Leu Thr Ala Leu Val Leu Val Leu Trp
            165                 170                 175

Thr Ala Tyr Pro Ile Leu Trp Ile Ile Gly Thr Gly Ala Gly Val
        180                 185                 190

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
            245                 250                 255

Ala Asp Arg Pro Val Val Ala Val Ser Lys Ala Ala Val Ser Lys
            260                 265                 270

Gly Glu Glu Leu Phe Thr Gly Val Val Pro Ile Leu Val Glu Leu Asp
            275                 280                 285

Gly Asp Val Asn Gly His Lys Phe Ser Val Ser Gly Glu Gly Glu Gly
290                 295                 300

Asp Ala Thr Tyr Gly Lys Leu Thr Leu Lys Phe Ile Cys Thr Thr Gly
305                 310                 315                 320

Lys Leu Pro Val Pro Trp Pro Thr Leu Val Thr Thr Phe Gly Tyr Gly
            325                 330                 335

Leu Gln Cys Phe Ala Arg Tyr Pro Asp His Met Lys Gln His Asp Phe
            340                 345                 350

Phe Lys Ser Ala Met Pro Glu Gly Tyr Val Gln Glu Arg Thr Ile Phe
            355                 360                 365

Phe Lys Asp Asp Gly Asn Tyr Lys Thr Arg Ala Glu Val Lys Phe Glu
            370                 375                 380

Gly Asp Thr Leu Val Asn Arg Ile Glu Leu Lys Gly Ile Asp Phe Lys
385                 390                 395                 400

Glu Asp Gly Asn Ile Leu Gly His Lys Leu Glu Tyr Asn Tyr Asn Ser
                405                 410                 415

His Asn Val Tyr Ile Met Ala Asp Lys Gln Lys Asn Gly Ile Lys Val
            420                 425                 430

Asn Phe Lys Ile Arg His Asn Ile Glu Asp Gly Ser Val Gln Leu Ala
            435                 440                 445

Asp His Tyr Gln Gln Asn Thr Pro Ile Gly Asp Gly Pro Val Leu Leu
450                 455                 460

Pro Asp Asn His Tyr Leu Ser Tyr Gln Ser Ala Leu Ser Lys Asp Pro
465                 470                 475                 480

Asn Glu Lys Arg Asp His Met Val Leu Leu Glu Phe Val Thr Ala Ala
            485                 490                 495

Gly Ile Thr Leu Gly Met Asp Glu Leu Tyr Lys Phe Cys Tyr Glu Asn
            500                 505                 510

Glu Val

<210> SEQ ID NO 24
<211> LENGTH: 534
<212> TYPE: PRT
<213> ORGANISM: Artificial sequence
<220> FEATURE:
<223> OTHER INFORMATION: Synthetic sequence

<400> SEQUENCE: 24

-continued

```
Met Asp Pro Ile Ala Leu Gln Ala Gly Tyr Asp Leu Leu Gly Asp Gly
1               5                  10                 15

Arg Pro Glu Thr Leu Trp Leu Gly Ile Gly Thr Leu Leu Met Leu Ile
            20                  25                 30

Gly Thr Phe Tyr Phe Leu Val Arg Gly Trp Gly Val Thr Asp Lys Asp
        35                  40                 45

Ala Arg Glu Tyr Tyr Ala Val Thr Ile Leu Val Pro Gly Ile Ala Ser
50                  55                 60

Ala Ala Tyr Leu Ser Met Phe Phe Gly Ile Gly Leu Thr Glu Val Thr
65                  70                 75                 80

Val Gly Gly Glu Met Leu Asp Ile Tyr Tyr Ala Arg Tyr Ala Asp Trp
                85                  90                 95

Leu Phe Thr Thr Pro Leu Leu Leu Leu Asp Leu Ala Leu Leu Ala Lys
            100                 105                110

Val Asp Arg Val Thr Ile Gly Thr Leu Val Gly Val Asp Ala Leu Met
        115                 120                125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                160

Phe Leu Ala Thr Ser Leu Arg Ser Ala Ala Lys Glu Arg Gly Pro Glu
                165                 170                175

Val Ala Ser Thr Phe Asn Thr Leu Thr Ala Leu Val Leu Val Leu Trp
            180                 185                190

Thr Ala Tyr Pro Ile Leu Trp Ile Ile Gly Thr Glu Gly Ala Gly Val
        195                 200                205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                240

Gly Asp Thr Glu Ala Pro Glu Pro Ser Ala Gly Ala Asp Val Ser Ala
                245                 250                255

Ala Asp Arg Pro Val Val Ala Val Ser Lys Ala Ala Ala Lys Ser Arg
            260                 265                270

Ile Thr Ser Glu Gly Glu Tyr Ile Pro Leu Asp Gln Ile Asp Ile Asn
        275                 280                285

Val Val Ser Lys Gly Glu Glu Leu Phe Thr Gly Val Val Pro Ile Leu
    290                 295                 300

Val Glu Leu Asp Gly Asp Val Asn Gly His Lys Phe Ser Val Ser Gly
305                 310                 315                320

Glu Gly Glu Gly Asp Ala Thr Tyr Gly Lys Leu Thr Leu Lys Phe Ile
                325                 330                335

Cys Thr Thr Gly Lys Leu Pro Val Pro Trp Pro Thr Leu Val Thr Thr
            340                 345                350

Phe Gly Tyr Gly Leu Gln Cys Phe Ala Arg Tyr Pro Asp His Met Lys
        355                 360                365

Gln His Asp Phe Phe Lys Ser Ala Met Pro Glu Gly Tyr Val Gln Glu
    370                 375                380

Arg Thr Ile Phe Phe Lys Asp Asp Gly Asn Tyr Lys Thr Arg Ala Glu
385                 390                 395                400

Val Lys Phe Glu Gly Asp Thr Leu Val Asn Arg Ile Glu Leu Lys Gly
                405                 410                415
```

Ile Asp Phe Lys Glu Asp Gly Asn Ile Leu Gly His Lys Leu Glu Tyr
                420                 425                 430

Asn Tyr Asn Ser His Asn Val Tyr Ile Met Ala Asp Lys Gln Lys Asn
            435                 440                 445

Gly Ile Lys Val Asn Phe Lys Ile Arg His Asn Ile Glu Asp Gly Ser
        450                 455                 460

Val Gln Leu Ala Asp His Tyr Gln Gln Asn Thr Pro Ile Gly Asp Gly
465                 470                 475                 480

Pro Val Leu Leu Pro Asp Asn His Tyr Leu Ser Tyr Gln Ser Ala Leu
                485                 490                 495

Ser Lys Asp Pro Asn Glu Lys Arg Asp His Met Val Leu Leu Glu Phe
            500                 505                 510

Val Thr Ala Ala Gly Ile Thr Leu Gly Met Asp Glu Leu Tyr Lys Phe
        515                 520                 525

Cys Tyr Glu Asn Glu Val
    530

<210> SEQ ID NO 25
<211> LENGTH: 516
<212> TYPE: PRT
<213> ORGANISM: Artificial sequence
<220> FEATURE:
<223> OTHER INFORMATION: Synthetic sequence

<400> SEQUENCE: 25

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
        35                  40                  45

Ala Arg Glu Tyr Tyr Ser Ile Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
        115                 120                 125

Ile Val Thr Gly Leu Ile Gly Ala Leu Ser His Thr Pro Leu Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

-continued

Gly Asp Thr Glu Ala Pro Glu Pro Ala Ala Lys Ser Arg Ile Thr
            245                 250                 255

Ser Glu Gly Glu Tyr Ile Pro Leu Asp Gln Ile Asp Ile Asn Val Val
        260                 265                 270

Ser Lys Gly Glu Glu Leu Phe Thr Gly Val Val Pro Ile Leu Val Glu
    275                 280                 285

Leu Asp Gly Asp Val Asn Gly His Lys Phe Ser Val Ser Gly Glu Gly
290                 295                 300

Glu Gly Asp Ala Thr Tyr Gly Lys Leu Thr Leu Lys Phe Ile Cys Thr
305                 310                 315                 320

Thr Gly Lys Leu Pro Val Pro Trp Pro Thr Leu Val Thr Thr Phe Gly
                325                 330                 335

Tyr Gly Leu Gln Cys Phe Ala Arg Tyr Pro Asp His Met Lys Gln His
            340                 345                 350

Asp Phe Phe Lys Ser Ala Met Pro Glu Gly Tyr Val Gln Glu Arg Thr
        355                 360                 365

Ile Phe Phe Lys Asp Asp Gly Asn Tyr Lys Thr Arg Ala Glu Val Lys
    370                 375                 380

Phe Glu Gly Asp Thr Leu Val Asn Arg Ile Glu Leu Lys Gly Ile Asp
385                 390                 395                 400

Phe Lys Glu Asp Gly Asn Ile Leu Gly His Lys Leu Glu Tyr Asn Tyr
                405                 410                 415

Asn Ser His Asn Val Tyr Ile Met Ala Asp Lys Gln Lys Asn Gly Ile
            420                 425                 430

Lys Val Asn Phe Lys Ile Arg His Asn Ile Glu Asp Gly Ser Val Gln
        435                 440                 445

Leu Ala Asp His Tyr Gln Gln Asn Thr Pro Ile Gly Asp Gly Pro Val
    450                 455                 460

Leu Leu Pro Asp Asn His Tyr Leu Ser Tyr Gln Ser Ala Leu Ser Lys
465                 470                 475                 480

Asp Pro Asn Glu Lys Arg Asp His Met Val Leu Leu Glu Phe Val Thr
                485                 490                 495

Ala Ala Gly Ile Thr Leu Gly Met Asp Glu Leu Tyr Lys Phe Cys Tyr
            500                 505                 510

Glu Asn Glu Val
            515

<210> SEQ ID NO 26
<211> LENGTH: 569
<212> TYPE: PRT
<213> ORGANISM: Artificial sequence
<220> FEATURE:
<223> OTHER INFORMATION: Synthetic sequence

<400> SEQUENCE: 26

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

Ala Ser Ala Ala Phe Thr Ala Leu Ser Trp Lys Ile Pro Val Asn Arg
65                  70                  75                  80

-continued

```
Arg Leu Tyr His Val Ile Thr Thr Ile Ile Thr Leu Thr Ala Ala Leu
                85                  90                  95
Ser Tyr Phe Ala Met Ala Thr Gly His Gly Val Ala Leu Asn Lys Ile
            100                 105                 110
Val Ile Arg Thr Gln His Asp His Val Pro Asp Thr Tyr Glu Thr Val
        115                 120                 125
Tyr Arg Gln Val Tyr Tyr Ala Arg Tyr Ile Asp Trp Ala Ile Thr Thr
    130                 135                 140
Pro Leu Leu Leu Leu Asp Leu Gly Leu Leu Ala Gly Met Ser Gly Ala
145                 150                 155                 160
His Ile Phe Met Ala Ile Val Ala Asp Leu Ile Met Val Leu Thr Gly
                165                 170                 175
Leu Phe Ala Ala Phe Gly Ser Glu Gly Thr Pro Gln Lys Trp Gly Trp
            180                 185                 190
Tyr Thr Ile Ala Cys Ile Ala Tyr Ile Phe Val Val His Leu Val
        195                 200                 205
Leu Asn Gly Gly Ala Asn Ala Arg Val Lys Gly Glu Lys Leu Arg Ser
    210                 215                 220
Phe Phe Val Ala Ile Gly Ala Tyr Thr Leu Ile Leu Trp Thr Ala Tyr
225                 230                 235                 240
Pro Ile Val Trp Gly Leu Ala Asp Gly Ala Arg Lys Ile Gly Val Asp
                245                 250                 255
Gly Glu Ile Ile Ala Tyr Ala Val Leu Asp Val Leu Ala Lys Gly Val
            260                 265                 270
Phe Gly Ala Trp Leu Leu Val Thr His Ala Asn Leu Arg Glu Ser Asp
        275                 280                 285
Val Glu Leu Asn Gly Phe Trp Ala Asn Gly Leu Asn Arg Glu Gly Ala
    290                 295                 300
Ile Arg Ile Gly Glu Asp Asp Gly Ala Arg Pro Val Val Ala Val Ser
305                 310                 315                 320
Lys Ala Ala Ala Val Ser Lys Gly Glu Glu Leu Phe Thr Gly Val Val
                325                 330                 335
Pro Ile Leu Val Glu Leu Asp Gly Asp Val Asn Gly His Lys Phe Ser
            340                 345                 350
Val Ser Gly Glu Gly Glu Gly Asp Ala Thr Tyr Gly Lys Leu Thr Leu
        355                 360                 365
Lys Phe Ile Cys Thr Thr Gly Lys Leu Pro Val Pro Trp Pro Thr Leu
    370                 375                 380
Val Thr Thr Phe Gly Tyr Gly Leu Gln Cys Phe Ala Arg Tyr Pro Asp
385                 390                 395                 400
His Met Lys Gln His Asp Phe Phe Lys Ser Ala Met Pro Glu Gly Tyr
                405                 410                 415
Val Gln Glu Arg Thr Ile Phe Phe Lys Asp Asp Gly Asn Tyr Lys Thr
            420                 425                 430
Arg Ala Glu Val Lys Phe Glu Gly Asp Thr Leu Val Asn Arg Ile Glu
        435                 440                 445
Leu Lys Gly Ile Asp Phe Lys Glu Asp Gly Asn Ile Leu Gly His Lys
    450                 455                 460
Leu Glu Tyr Asn Tyr Asn Ser His Asn Val Tyr Ile Met Ala Asp Lys
465                 470                 475                 480
Gln Lys Asn Gly Ile Lys Val Asn Phe Lys Ile Arg His Asn Ile Glu
                485                 490                 495
Asp Gly Ser Val Gln Leu Ala Asp His Tyr Gln Gln Asn Thr Pro Ile
```

```
            500                 505                 510
Gly Asp Gly Pro Val Leu Leu Pro Asp Asn His Tyr Leu Ser Tyr Gln
        515                 520                 525

Ser Ala Leu Ser Lys Asp Pro Asn Glu Lys Arg Asp His Met Val Leu
        530                 535                 540

Leu Glu Phe Val Thr Ala Ala Gly Ile Thr Leu Gly Met Asp Glu Leu
545                 550                 555                 560

Tyr Lys Phe Cys Tyr Glu Asn Glu Val
                565

<210> SEQ ID NO 27
<211> LENGTH: 589
<212> TYPE: PRT
<213> ORGANISM: Artificial sequence
<220> FEATURE:
<223> OTHER INFORMATION: Synthetic sequence

<400> SEQUENCE: 27

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Ile Ile Thr Leu Thr Ala Ala Leu
                85                  90                  95

Ser Tyr Phe Ala Met Ala Thr Gly His Gly Val Ala Leu Asn Lys Ile
                100                 105                 110

Val Ile Arg Thr Gln His Asp His Val Pro Asp Thr Tyr Glu Thr Val
            115                 120                 125

Tyr Arg Gln Val Tyr Tyr Ala Arg Tyr Ile Asp Trp Ala Ile Thr Thr
        130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
```

```
            290                 295                 300
Ile Arg Ile Gly Glu Asp Asp Gly Ala Arg Pro Val Ala Val Ser
305                 310                 315                 320

Lys Ala Ala Lys Ser Arg Ile Thr Ser Glu Gly Glu Tyr Ile Pro
            325                 330                 335

Leu Asp Gln Ile Asp Ile Asn Val Val Ser Lys Gly Glu Glu Leu Phe
            340                 345                 350

Thr Gly Val Val Pro Ile Leu Val Glu Leu Asp Gly Asp Val Asn Gly
            355                 360                 365

His Lys Phe Ser Val Ser Gly Glu Gly Glu Gly Asp Ala Thr Tyr Gly
            370                 375                 380

Lys Leu Thr Leu Lys Phe Ile Cys Thr Thr Gly Lys Leu Pro Val Pro
385                 390                 395                 400

Trp Pro Thr Leu Val Thr Thr Phe Gly Tyr Gly Leu Gln Cys Phe Ala
            405                 410                 415

Arg Tyr Pro Asp His Met Lys Gln His Asp Phe Phe Lys Ser Ala Met
            420                 425                 430

Pro Glu Gly Tyr Val Gln Glu Arg Thr Ile Phe Phe Lys Asp Asp Gly
            435                 440                 445

Asn Tyr Lys Thr Arg Ala Glu Val Lys Phe Glu Gly Asp Thr Leu Val
            450                 455                 460

Asn Arg Ile Glu Leu Lys Gly Ile Asp Phe Lys Glu Asp Gly Asn Ile
465                 470                 475                 480

Leu Gly His Lys Leu Glu Tyr Asn Tyr Asn Ser His Asn Val Tyr Ile
            485                 490                 495

Met Ala Asp Lys Gln Lys Asn Gly Ile Lys Val Asn Phe Lys Ile Arg
            500                 505                 510

His Asn Ile Glu Asp Gly Ser Val Gln Leu Ala Asp His Tyr Gln Gln
            515                 520                 525

Asn Thr Pro Ile Gly Asp Gly Pro Val Leu Leu Pro Asp Asn His Tyr
            530                 535                 540

Leu Ser Tyr Gln Ser Ala Leu Ser Lys Asp Pro Asn Glu Lys Arg Asp
545                 550                 555                 560

His Met Val Leu Leu Glu Phe Val Thr Ala Ala Gly Ile Thr Leu Gly
            565                 570                 575

Met Asp Glu Leu Tyr Lys Phe Cys Tyr Glu Asn Glu Val
            580                 585

<210> SEQ ID NO 28
<211> LENGTH: 258
<212> TYPE: PRT
<213> ORGANISM: Halorubrum sodomense

<400> SEQUENCE: 28

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
            50                  55                  60

Ala Ala Tyr Leu Ser Met Phe Phe Gly Ile Gly Leu Thr Glu Val Thr
65                  70                  75                  80
```

```
Val Gly Gly Glu Met Leu Asp Ile Tyr Tyr Ala Arg Tyr Ala Asp Trp
            85                  90                  95
Leu Phe Thr Thr Pro Leu Leu Leu Asp Leu Ala Leu Leu Ala Lys
        100                 105                 110
Val Asp Arg Val Thr Ile Gly Thr Leu Val Gly Val Asp Ala Leu Met
        115                 120                 125
Ile Val Thr Gly Leu Ile Gly Ala Leu Ser His Thr Ala Ile Ala Arg
    130                 135                 140
Tyr Ser Trp Trp Leu Phe Ser Thr Ile Cys Met Ile Val Val Leu Tyr
145                 150                 155                 160
Phe Leu Ala Thr Ser Leu Arg Ser Ala Ala Lys Glu Arg Gly Pro Glu
                165                 170                 175
Val Ala Ser Thr Phe Asn Thr Leu Thr Ala Leu Val Leu Val Leu Trp
            180                 185                 190
Thr Ala Tyr Pro Ile Leu Trp Ile Ile Gly Thr Glu Gly Ala Gly Val
        195                 200                 205
Val Gly Leu Gly Ile Glu Thr Leu Leu Phe Met Val Leu Asp Val Thr
    210                 215                 220
Ala Lys Val Gly Phe Gly Phe Ile Leu Leu Arg Ser Arg Ala Ile Leu
225                 230                 235                 240
Gly Asp Thr Glu Ala Pro Glu Pro Ser Ala Gly Ala Asp Val Ser Ala
                245                 250                 255
Ala Asp

<210> SEQ ID NO 29
<211> LENGTH: 948
<212> TYPE: DNA
<213> ORGANISM: Halorubrum sodomense

<400> SEQUENCE: 29
ctgggttggc atcggtctca atagagtata tactgtatca ggatgtgggt atggacccga    60
tagcactaca ggcgggatac gacctactcg gggacggtcg ccccgagacg ttgtggttgg   120
gtatcggaac gttactaatg ctcatcggga ccttctactt cctcgtcaga gggtgggggg   180
tcaccgacaa ggacgcccgc gagtactacg cggtcacgat cctcgtgccg gggatcgcgt   240
cggcggcgta cctgtcgatg ttcttcggca tcggcctgac ggaagtcacg gtcggtggcg   300
aaatgctcga catctactac gcgcggtacg cggactggct gttcaccacg ccgctgctgc   360
tgctcgacct cgcgctgctc gcaaaggtcg accgcgtcac catcgggacg ctcgtcggcg   420
tcgacgcgct gatgatcgtc accggcctca tcggcgcgct ctcgcacacg gcgatcgcgc   480
ggtactcctg gtggctgttc agcacgattt gcatgatcgt cgtgctgtac ttcctcgcca   540
cgagcctccg gagcgcggcg aaggagcgcg gacctgaagt cgcgagcacc ttcaacacgt   600
tgaccgcgct ggtcctggtg ctctggacgg cctacccgat cctgtggatc atcggaaccg   660
agggcgccgg cgtcgtcggc ctcggcatcg agacctcct gttcatggtt ctcgacgtga   720
cggccaaggt cggcttcggc ttcatcctgc tccgcagccg cgccatcctc ggcgacaccg   780
aggcgccgga gccctccgcg ggcgccgacg tctccgccgc ggactgatcg gctagcggac   840
ccagcgaaac tgaacagcgc gcgaacgact ttcacaaccc attcttcaca tgagcgctac   900
gaacaccgaa cagccggcag tgctgaatac gcggtccgtc gtcgggct                948

<210> SEQ ID NO 30
<211> LENGTH: 777
<212> TYPE: DNA
```

<213> ORGANISM: Artificial sequence
<220> FEATURE:
<223> OTHER INFORMATION: Synthetic sequence

<400> SEQUENCE: 30

```
atggacccca tcgctctgca ggctggttac gacctgctgg gtgacggcag acctgaaact      60
ctgtggctgg gcatcggcac tctgctgatg ctgattggaa ccttctactt tctggtccgc     120
ggatggggag tcaccgataa ggatgcccgg gaatattacg ctgtgactat cctggtgccc     180
ggaatcgcat ccgccgcata tctgtctatg ttctttggta tcgggcttac tgaggtgacc     240
gtcgggggcg aaatgttgga tatctattat gccaggtacg ccgactggct gtttaccacc     300
ccacttctgc tgctggatct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
tttctggcta catccctgcg atctgctgca aaggagcggg ccccgaggt ggcatctacc      540
tttaacaccc tgacagctct ggtcttggtg ctgtggaccc ttaccctat cctgtggatc      600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaga acccagtgcc ggtgccgatg tcagtgccgc cgactaa        777
```

<210> SEQ ID NO 31
<211> LENGTH: 258
<212> TYPE: PRT
<213> ORGANISM: Halorubrum sodomense

<400> SEQUENCE: 31

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
        35                  40                  45

Ala Arg Glu Tyr Tyr Ser Ile Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
        115                 120                 125

Ile Val Thr Gly Leu Ile Gly Ala Leu Ser His Thr Pro Leu Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205
```

```
Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Glu Ala Ser Ala
                245                 250                 255

Ala Asp

<210> SEQ ID NO 32
<211> LENGTH: 777
<212> TYPE: DNA
<213> ORGANISM: Halorubrum sodomense

<400> SEQUENCE: 32
tcagtccgcg gcggaggcct cagcgcccgc ggagggctcc ggggcctcgg tgtcgccgag    60
gatcgcgcgg ctgcggagca ggatgaagcc gaagccgacc ttggcggtca cgtcgagaac   120
catgaacagg agggtctcga tgccgaggcc gacgacgccg gctccctcag taccgatgat   180
ccagaggatc gggtacgcgg tccagaggac gagcaccaac gcggtcagcg tgttgaacgt   240
gctcgcgact cgggccgcc gctccttcgc cgcggcgcgc aggctcgtgg cgaggaagta   300
cagcacgacg atcatgcaga tcgtgctgaa cagccaccag gagtaccgcg cgagcggcgt   360
gtgcgagagc cgccgatga ggccggtgac gatcatcagc gcgtcgacgc cgacgagcgt   420
cccgatgctc acgcggtcga ccttcgccag cagcgcgagg tcgagcagca gcagcggcgt   480
ggtgaacagc cagtccgcgt accgcgcgta gtagatgtcg agcacttctc cggcgaccgt   540
gacttccgtc aggccgattc cgaagaacat cgacaggtac gccgccgacg cgatccccgg   600
cacgaggatc gtaatcgagt agtactcacg ggcctccttg tcggtgaccc ccatccttt    660 gacgatgaag tagaaggtcc cgatgagcat tagtagcgtg cctataccca accaaagcgt   720
ctcgggacgt ccgtccccga gcaggtcgta tcccgcctgt agcgctatcg ggtccat      777

<210> SEQ ID NO 33
<211> LENGTH: 313
<212> TYPE: PRT
<213> ORGANISM: Leptosphaeria maculans

<400> SEQUENCE: 33

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
                20                  25                  30

Pro Val Pro Thr Val Leu Pro Asp Thr Pro Ile Tyr Glu Thr Val Gly
            35                  40                  45

Asp Ser Gly Ser Lys Thr Leu Trp Val Val Phe Val Leu Met Leu Ile
        50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Ile Thr Leu Thr Ala Ala Leu
                85                  90                  95

Ser Tyr Phe Ala Met Ala Thr Gly His Gly Val Ala Leu Asn Lys Ile
                100                 105                 110

Val Ile Arg Thr Gln His Asp His Val Pro Asp Thr Tyr Glu Thr Val
            115                 120                 125

Tyr Arg Gln Val Tyr Tyr Ala Arg Tyr Ile Asp Trp Ala Ile Thr Thr
        130                 135                 140
```

```
Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
            165                 170                 175

Leu Phe Ala Ala Phe Gly Ser Glu Gly Thr Pro Gln Lys Trp Gly Trp
        180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
                260                 265                 270

Phe Gly Ala Trp Leu Leu Val Thr His Ala Asn Leu Arg Glu Ser Asp
            275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala
305                 310

<210> SEQ ID NO 34
<211> LENGTH: 942
<212> TYPE: DNA
<213> ORGANISM: Leptosphaeria maculans

<400> SEQUENCE: 34
atgattgttg accaattcga ggaagtcctg atgaagacgt cacagctctt cccgctgccg      60
acggccaccc aatcggccca gcctacccat gtggcgcctg tgcccacggt cctaccagac     120
actcccatct acgagacggt cggcgattcc ggcagcaaga cgctctgggt ggtcttcgtg     180
ctcatgctga ttgcctctgc tgctttcact gccttgtcat ggaagatccc agttaacagg     240
cgtttgtacc atgtcatcac gacaatcatc acgttgactg ctgctctttc ttactttgcc     300
atggccactg ccacggcgt tgccctcaac aagattgtca ttcgcactca gcatgaccat     360
gtccccgaca cgtacgagac cgtataccgc caggtctact atgctcgtta cattgactgg     420
gccatcacca ctcctcttct gctcctcgat cttggtctcc tggctggcat gtccggtgcc     480
cacatcttca tggccattgt cgctgatttg atcatggtct tgactggtct cttcgctgcc     540
ttcggttccg agggcactcc ccagaagtgg ggctggtaca ctattgcctg cattgcctac     600
atcttcgttg tctggcacct ggtcctgaac ggaggtgcca acgccagggt caagggcgag     660
aagctccgat ctttctttgt tgccattggt gcctacactc tgattctttg gaccgcctat     720
cccattgttt ggggtctagc agatggtgcc cgcaagatcg gtgttgacgg tgagatcatt     780
gcctacgccg ttcttgacgt ccttgccaag ggtgtctttg gtgcatggct tctagtcacc     840
cacgccaatc ttcgtgagag cgatgttgag ctcaacggct ctgggccaa cggcctcaac     900
cgtgagggtg ctattcgcat tggtgaggat gacggtgctt aa                        942

<210> SEQ ID NO 35
<211> LENGTH: 942
<212> TYPE: DNA
<213> ORGANISM: Artificial sequence
```

```
<220> FEATURE:
<223> OTHER INFORMATION: Synthetic sequence

<400> SEQUENCE: 35
atgatcgtgg accagttcga ggaggtgctg atgaagacca gccagctgtt cccactgcca      60
accgctaccc agagcgccca gccaacccac gtggcccccg tgccaaccgt gctgcccgac     120
acccccatct acgagaccgt gggcgacagc ggcagcaaga ccctgtgggt ggtgttcgtg     180
ctgatgctga tcgccagcgc cgccttcacc gccctgagct ggaagatccc cgtgaacagg     240
aggctgtacc acgtgatcac caccatcatc accctgaccg ccgccctgag ctacttcgct     300
atggctaccg ccacggagt ggccctgaac aagatcgtga tcaggaccca gcacgaccac     360
gtgcccgaca cctacgagac cgtgtaccga caggtgtact acgccaggta catcgactgg     420
gctatcacca ccccactgct gctgctggac ctgggactgc tggctggaat gagcggagcc     480
cacatcttca tggccatcgt ggctgacctg atcatggtgc tgaccggcct gttcgctgct     540
ttcggcagcg agggaacccc acagaagtgg ggatggtaca ccatcgcctg catcgcctac     600
atcttcgtgg tgtggcacct ggtgctgaac ggcggcgcca acgccagggt gaagggcgag     660
aagctgagga gcttcttcgt ggccatcgga gcttacaccc tgatcctgtg gaccgcttac     720
ccaatcgtgt ggggactggc tgacggagct aggaagatcg gagtggacgg agagatcatc     780
gcttacgctg tgctggacgt gctggctaag ggagtgttcg gagcttggct gctggtgacc     840
cacgccaacc tgagggagag cgacgtggag ctgaacggct tctgggccaa cggcctgaac     900
agggagggcg ccatcaggat cggcgaggac gacggcgcct aa                        942
```

OPSIN POLYPEPTIDES AND METHODS OF USE THEREOF

CROSS-REFERENCE

This application is a divisional application of U.S. patent application Ser. No. 15/334,007, filed Oct. 25, 2016, which is a divisional application of U.S. patent application Ser. No. 15/097,925, filed Apr. 13, 2016, now U.S. Pat. No. 9,505,817, which is a divisional application of U.S. patent application Ser. No. 14/365,477, filed Jun. 13, 2014, now U.S. Pat. No. 9,365,628, which is a national stage filing under 35 U.S.C. § 371 of PCT/US2012/069133, filed Dec. 12, 2012, which claims the benefit of U.S. Provisional Patent Application No. 61/576,858, filed Dec. 16, 2011, each of which applications is incorporated herein by reference in its entirety.

BACKGROUND

Diverse and elegant mechanisms have evolved to enable organisms to harvest light for a variety of survival functions, including energy generation and the identification of suitable survival environments. A major class of light-sensitive protein consists of 7-transmembrane rhodopsins that can be found across all kingdoms of life and serve a diverse range of functions. Many prokaryotes employ these proteins to control proton gradients and to maintain membrane potential and ionic homeostasis, and many motile microorganisms have evolved opsin-based photoreceptors to modulate flagellar beating and thereby direct phototaxis toward environments with optimal light intensities for photosynthesis.

Owing to their structural simplicity (both light sensation and effector domains are encoded within a single gene) and fast kinetics, microbial opsins can be treated as precise and modular photosensitization components for introduction into non-light sensitive cells to enable rapid optical control of specific cellular processes. In recent years, the development of cellular perturbation tools based on these and other light sensitive proteins has resulted in a technology called optogenetics, referring to the integration of genetic and optical control to achieve gain- or loss-of-function of precisely defined events within specified cells of living tissue.

There is a need in the art for depolarizing and hyperpolarizing optogenetic tools, e.g., for use in controlling neural activity.

SUMMARY

The present disclosure provides opsins, including variant opsins with increased activity and/or increased trafficking to the plasma membrane. The opsins are useful in therapeutic and screening applications, which are also provided.

BRIEF DESCRIPTION OF THE DRAWINGS

FIGS. 1A-1F depict properties of hyperpolarizing tools.

FIGS. 2A-2F depict performance of hyperpolarizing tools.

FIGS. 3A-3F depict characterization of a ChR from *Dunaliella salina*. For FIG. 3B: DChR1 (SEQ ID NO: 15), CChR1 (SEQ ID NO: 16), CChR2 (SEQ ID NO: 17), VChR1 (SEQ ID NO: 18), and VChR2 (SEQ ID NO: 19).

FIG. 4 depicts a nucleotide sequence encoding a ChR from *Dunaliella salina* (SEQ ID NO: 20).

FIG. 5 depicts a nucleotide sequence encoding a ChR from *Dunaliella salina*, codon optimized for expression in mammalian cells (SEQ ID NO: 21).

FIG. 6 depicts an amino acid sequence of *Dunaliella salina* ChR (SEQ ID NO: 22).

FIGS. 7A-7E depict the amino acid sequences of exemplary variant opsins: FIG. 7A (SEQ ID NO: 23); FIG. 7B (SEQ ID NO: 24); FIG. 7C (SEQ ID NO: 25); FIG. 7D (SEQ ID NO: 26); and FIG. 7E (SEQ ID NO: 27).

FIGS. 8A-8C depict an amino acid sequence of *Halorubrum sodomense* archaerhodopsin-3; and nucleotide sequences encoding same: FIG. 8A (SEQ ID NO: 28); FIG. 8B (SEQ ID NO: 29); and FIG. 8C (SEQ ID NO: 30).

FIGS. 9A and 9B depict an amino acid sequence of *Halorubrum sodomense* strain TP009 opsin; and a nucleotide sequence encoding same: FIG. 9A (SEQ ID NO: 31) and FIG. 9B (SEQ ID NO: 32).

FIGS. 10A-10C depict an amino acid sequence of *Leptosphaeria maculans* opsin and nucleotides sequences encoding same: FIG. 10A (SEQ ID NO: 33); FIG. 10B (SEQ ID NO: 34); and FIG. 10C (SEQ ID NO: 35).

DEFINITIONS

Figure 1A:
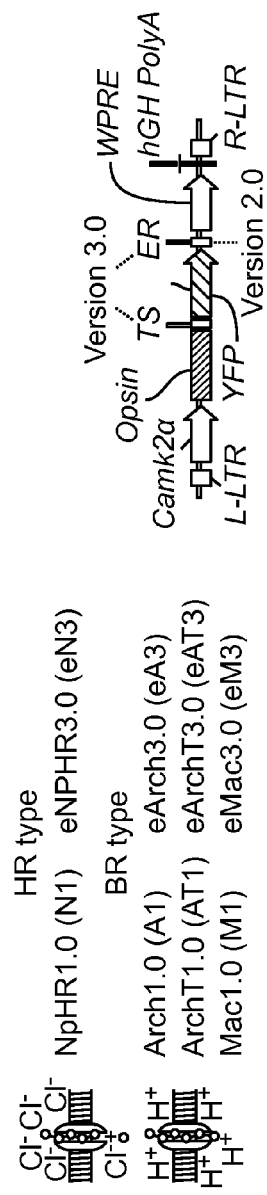

The terms "polypeptide," "peptide," and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than the in vitro manipulations; however, such nucleic acids, once produced recombinantly, although subsequently replicated non-recombinantly, are still considered recombinant for the purposes of the invention.

Nucleic acid sequence identity (as well as amino acid sequence identity) is calculated based on a reference sequence, which may be a subset of a larger sequence, such as a conserved motif, coding region, flanking region, etc. A reference sequence will usually be at least about 18 residues long, more usually at least about 30 residues long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17).

The term "genetic modification" and refers to a permanent or transient genetic change induced in a cell following introduction into the cell of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells. An isolated polypeptide will in some embodiments be synthetic. "Synthetic polypeptides" are assembled from amino acids, and are chemically synthesized in vitro, e.g., cell-free chemical synthesis, using procedures known to those skilled in the art.

By "purified" is meant a compound of interest (e.g., a polypeptide) has been separated from components that accompany it in nature. "Purified" can also be used to refer to a compound of interest separated from components that can accompany it during manufacture (e.g., in chemical synthesis). In some embodiments, a compound is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. A substantially pure polypeptide can be obtained, for example, by chemically synthesizing the polypeptide, or by a combination of purification and chemical modification. A substantially pure polypeptide can also be obtained by, for example, affinity chromatography. Purity can be measured by any appropriate method, e.g., chromatography, mass spectroscopy, high performance liquid chromatography analysis, etc.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some embodiments, the individual is a human. In some embodiments, the individual is a murine.

The terms "treatment," "treating," "treat," and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

A "therapeutically effective amount" or "efficacious amount" means the amount of an agent that, when administered to a mammal or other subject for treating a disease, is sufficient to effect such treatment for the disease. The "therapeutically effective amount" will vary depending on agent, the disease or condition and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a variant opsin polypeptide" includes a plurality of such polypeptides and reference to "the trafficking signal" includes reference to one or more trafficking signals and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides opsins, including variant opsins with increased activity and/or increased trafficking to the plasma membrane. The opsins are useful in therapeutic and screening applications, which are also provided.

Opsins

The present disclosure provides opsin polypeptides, and nucleic acids ("opsin nucleic acids") comprising nucleotide sequences encoding the opsin polypeptides. The present disclosure also provides genetically modified host cells comprising an opsin nucleic acid. An opsin polypeptide is also referred to herein as a "tool."

A subject isolated opsin polypeptide comprises an amino acid sequence having at least about 85%, at least about 90%, at least about 95%, at least about 97%, at least about 98%, at least about 99%, or 100%, amino acid sequence identity to a contiguous stretch of from about 500 amino acids to about 550 amino acids, from about 550 amino acids to about 600 amino acids, from about 600 amino acids to about 650 amino acids, from about 650 amino acids to about 700 amino acids, or from about 700 amino acids to 720 amino acids, of the amino acid sequence depicted in FIG. 6. Such an opsin can be referred to as "DChR1."

A subject isolated opsin polypeptide can have a length of from about 500 amino acids to about 550 amino acids, from about 550 amino acids to about 600 amino acids, from about 600 amino acids to about 650 amino acids, from about 650 amino acids to about 700 amino acids, or from about 700 amino acids to 720 amino acids.

An isolated opsin polypeptide of the present disclosure can be encoded by a nucleotide sequence having at least about 85%, at least about 90%, at least about 95%, at least about 97%, at least about 98%, at least about 99%, or 100%, nucleotide sequence identity to a contiguous stretch of from about 1800 nucleotides to about 1900 nucleotides, from about 1900 nucleotides to about 2000 nucleotides, from about 2000 nucleotides to about 2100 nucleotides, or from about 2100 nucleotides to 2163 nucleotides, of the nucleotide sequence depicted in FIG. 4 or FIG. 5.

An isolated opsin polypeptide of the present disclosure functions as a light-activated proton channel, e.g., a subject isolated opsin functions as a proton pump.

In some embodiments, a subject DChR1 opsin is modified to include an ER export sequence and/or a trafficking sequence, as described in detail below. Thus, in some embodiments, a subject DChR1 opsin comprises, in order from amino terminus to carboxyl terminus, a DChR1 opsin; and an ER export sequence. In some embodiments, a subject DChR1 opsin comprises, in order from amino terminus to carboxyl terminus, a DChR1 opsin; a trafficking sequence; and an ER export sequence. In some embodiments, a subject DChR1 opsin comprises, in order from amino terminus to carboxyl terminus, a DChR1 opsin; a trafficking sequence; an intervening sequence; and an ER export sequence. Suitable ER export sequences, trafficking sequences, and intervening sequences are described in detail below.

The present disclosure provides a composition comprising a subject opsin polypeptide. A subject opsin polypeptide composition can comprise, in addition to a subject opsin polypeptide, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acids

The present disclosure provides a nucleic acid comprising a nucleotide sequence encoding a subject opsin. A nucleotide sequence encoding a subject opsin can be operably linked to one or more regulatory elements, such as a promoter and enhancer, that allow expression of the nucleotide sequence in the intended target cells (e.g., a cell that is genetically modified to synthesize the encoded opsin).

In some embodiments, a DChR1-encoding nucleotide sequence has at least about 85%, at least about 90%, at least about 95%, at least about 97%, at least about 98%, at least about 99%, or 100%, nucleotide sequence identity to a contiguous stretch of from about 1800 nucleotides to about 1900 nucleotides, from about 1900 nucleotides to about 2000 nucleotides, from about 2000 nucleotides to about 2100 nucleotides, or from about 2100 nucleotides to 2163 nucleotides, of the nucleotide sequence depicted in FIG. 4. In some cases, the nucleotide sequence is codon-optimized for expression in a mammalian cell.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter;

in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LaI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject opsin can be present in an expression vector and/or a cloning vector. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding a protein of interest (e.g., an opsin). A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Also provided herein is a recombinant vector comprising a subject polynucleotide encoding a subject opsin or any variant thereof. A subject recombinant vector also include vectors comprising a polynucleotide which encodes an RNA (e.g., an mRNA) that when transcribed from the polynucleotides of the vector will result in the accumulation of a subject opsin on the plasma membranes of target animal cells. Vectors which may be used include, without limitation, lentiviral, HSV, adenoviral, and andeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and sites-pecific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" in *Parvoviruses* (J R Kerr, S F Cotmore. M E Bloom, R M Linden, C R Parrish, Eds.) p5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p 15-23, Hudder Arnold, London, UK (2006), the disclosures of which are hereby incorporated by reference herein in their entireties). Methods for purifying for vectors may be found in, for example, U.S. Pat. Nos. 6,566,118, 6,989,264, and 6,995,006 and International Patent Application Publication No.: WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos: WO 91/18088 and WO 93/09239; U.S. Pat. Nos: 4,797,368, 6,596,535, and 5,139,941; and European Patent No: 0488528, all of which are herein incorporated by reference in their entirety). These publications describe various AAV-derived constructs in which the rep and/or cap genes are deleted and replaced by a gene of interest, and the use of these constructs for transferring the gene of interest in vitro (into cultured cells) or in vivo (directly into an organism). A replication defective recombinant AAV can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, a subject recombinant vector is encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535.

In some cases, a subject opsin nucleic acid comprises a nucleotide sequence encoding the opsin, where the nucleotide sequence is operably linked to a neuron-specific transcription control element.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) Gene Therapy 11:52-60); a motor neuron-specific gene Hb9 promoter (see, e.g., U.S. Pat. No. 7,632,679; and Lee et al. (2004) Development 131:3295-3306); and an alpha subunit of Ca$(^{2+})$-calmodulin-dependent protein kinase II (CaMKIIα) promoter (see, e.g., Mayford et al. (1996) Proc. Natl. Acad. Sci. USA 93:13250).

Host Cells

The present disclosure provides isolated genetically modified host cells (e.g., in vitro cells) that are genetically modified with a subject nucleic acid. In some embodiments, a subject isolated genetically modified host cell can produce an opsin of the present disclosure.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. In some cases, the mammalian cell is a neuron, e.g., a non-immortalized (primary) neuron. In other cases, the mammalian cell is an immortalized cell line.

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

Suitable yeast cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium graminerum*, *Fusarium venenatum*, *Neurospora crassa*, *Chlamydomonas reinhardtii*, and the like.

Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science*

270:299-302. Examples of Salmonella strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Variant Opsins with Enhanced Membrane Trafficking

The present disclosure provides variant opsins with improved membrane trafficking properties. The present disclosure also provides nucleic acids encoding the variant opsins. In particular, a subject variant opsin is a hyperpolarizing opsin that includes an endoplasmic reticulum (ER) export sequence, a trafficking sequence (TS), or both an ER export sequence and a TS. The presence of the ER export sequence and/or the TS provides for enhanced membrane (e.g., plasma membrane) localization and ER export. In some cases, a subject variant opsin comprises one or more additional amino acids, which may be disposed between the TS and the ER and/or between the opsin and the TS.

Thus, in some cases, a variant opsin comprises, in order from amino terminus to carboxyl terminus: an opsin polypeptide; a trafficking sequence; and an ER export sequence.

Hyperpolarizing Opsins

Opsin amino acid sequences that are suitable for inclusion in a subject variant opsin include, e.g., an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 220 amino acids, from about 220 amino acids to about 230 amino acids, from about 230 amino acids to about 240 amino acids, or from about 240 amino acids to 257 amino acids, of the amino acid sequence depicted in FIG. 8A (*Halorubrum sodomense* archaerhodopsin-3).

Opsin amino acid sequences that are suitable for inclusion in a subject variant opsin include, e.g., an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 220 amino acids, from about 220 amino acids to about 230 amino acids, from about 230 amino acids to about 240 amino acids, or from about 240 amino acids to 257 amino acids, of the amino acid sequence depicted in FIG. 9A (*Halorubrum sodomense* strain TP009 archaerhodopsin).

Opsin amino acid sequences that are suitable for inclusion in a subject variant opsin include, e.g., an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 225 amino acids, from about 225 amino acids to about 250 amino acids, from about 250 amino acids to about 275 amino acids, from about 275 amino acids to about 300 amino acids, or from about 300 amino acids to 313 amino acids, of the amino acid sequence depicted in FIG. 10A (*Leptosphaeria maculans* opsin).

Endoplasmic Reticulum Export Sequences

Endoplasmic reticulum (ER) export sequences that are suitable for use in a modified opsin of the present disclosure include, e.g., VXXSL (where X is any amino acid) (e.g., VKESL (SEQ ID NO: 1); VLGSL (SEQ ID NO: 2); etc.); NANSFCYENEVALTSK (SEQ ID NO: 3); FXYENE (SEQ ID NO: 4) (where X is any amino acid), e.g., FCYENEV (SEQ ID NO: 5); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

Trafficking Sequences

Trafficking sequences that are suitable for use in a modified opsin of the present disclosure comprise an amino acid sequence having 90%, 91%, 92%, 93%, 94%, 95%, 96%, 97%, 98%, 99%, or 100%, amino acid sequence identity to an amino acid sequence such as one of the following:

1) the signal peptide of hChR2

(e.g., MDYGGALSAVGRELLFVTNPVVVNGS (SEQ ID NO: 6))

2) the β2 subunit signal peptide of the neuronal nicotinic acetylcholine receptor (e.g., MAGHSNSMALFSFSLLWLCSGVLGTEF (SEQ ID NO: 7));

3) a nicotinic acetylcholine receptor signal sequence (e.g., MGLRALMLWLLAAAGLVRESLQG (SEQ ID NO: 8));

4) a nicotinic acetylcholine receptor signal sequence (e.g., MRGTPLLLVVSLFSLLQD (SEQ ID NO: 9));

5) a signal sequence of human inward rectifier potassium channel Kir2.1

(e.g., KSRITSEGEYIPLDQIDINV (SEQ ID NO: 10)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Additional Sequences

As noted above, in some embodiments, a subject variant opsin comprises one or more amino acids in addition to the opsin, the TS, and the ER export sequence. For example, in some embodiments, a subject variant opsin comprises, in order from amino terminus to carboxyl terminus: an opsin; a TS; an intervening amino acid sequence; and an ER export signal sequence.

Suitable intervening amino acid sequences include, e.g., linkers; epitope tags; fluorescent proteins; peptides that provide for ease of purification; cleavable linker peptides; and the like.

Suitable fluorescent proteins that can be included in a subject variant opsin include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; mCherry; any of a variety of fluorescent and colored proteins from Anthozoan species, as described in, e.g., Matz et al. (1999) *Nature Biotechnol.* 17:969-973; and the like.

Exemplary Variant Opsins

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 220 amino acids, from about 220 amino acids to about 230 amino acids, from about 230 amino acids to about 240 amino acids, or from about 240 amino acids to 257 amino acids, of the amino acid sequence depicted in FIG. 8A (*Halorubrum sodomense* archaerhodopsin-3); and b) an ER export sequence. For example, the ER export sequence is selected from VXXSL (where X is any amino acid) (e.g., VKESL (SEQ ID NO:1); VLGSL (SEQ ID NO:2);VLGSL (SEQ ID NO:2); etc.); NANSFCYENEVALTSK (SEQ ID NO:3); and FXYENE (SEQ ID NO:4) (where X is any amino acid), e.g., FCYENEV (SEQ ID NO:5).

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 220 amino acids, from about 220 amino acids to about 230 amino acids, from about 230 amino acids to about 240 amino acids, or from about 240 amino acids to 257 amino acids, of the amino acid sequence depicted in FIG. 8A (*Halorubrum sodomense* archaerhodopsin-3); b) a fluorescent protein; and c) an ER export sequence. For example, the ER export sequence is selected from VXXSL (where X is any amino acid) (e.g., VKESL (SEQ ID NO: 1); VLGSL (SEQ ID NO:2); VLGSL (SEQ ID NO:2); etc.); NANSFCYENEVALTSK (SEQ ID NO:3); and FXYENE (SEQ ID NO:4) (where X is any amino acid), e.g., FCYENEV (SEQ ID NO:5).

In some embodiments, a subject variant opsin comprises an amino acid sequence having at least about 85%, or at least about 90%, 91%, 92%, 93%, 94%, 95%, 96%, 97%, 98%, 99%, or 100%, amino acid sequence identity to the amino acid sequence depicted in FIG. 7A.

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 220 amino acids, from about 220 amino acids to about 230 amino acids, from about 230 amino acids to about 240 amino acids, or from about 240 amino acids to 257 amino acids, of the amino acid sequence depicted in FIG. 8A (*Halorubrum sodomense* archaerhodopsin-3); b) a TS sequence; and c) an ER export sequence. For example, a TS sequence can comprise an amino acid sequence having 90%, 91%, 92%, 93%, 94%, 95%, 96%, 97%, 98%, 99%, or 100%, amino acid sequence identity to an amino acid sequence selected from: MDYGGALSAVGRELLFVTNPVVVNGS (SEQ ID NO:6); MAGHSNSMALFSFSLLWLCSGVLGTEF (SEQ ID NO:7); MGLRALMLWLLAAAGLVRESLQG (SEQ ID NO:8); MRGTPLLLVVSLFSLLQD (SEQ ID NO: 9); and KSRITSEGEYIPLDQIDINV (SEQ ID NO:10). For example, the ER export sequence is selected from VXXSL (where X is any amino acid) (e.g., VKESL (SEQ ID NO:1); VLGSL (SEQ ID NO:2); etc.); NANSFCYENEVALTSK (SEQ ID NO:3); and FXYENE (SEQ ID NO:4) (where X is any amino acid), e.g., FCYENEV (SEQ ID NO:5).

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 220 amino acids, from about 220 amino acids to about 230 amino acids, from about 230 amino acids to about 240 amino acids, or from about 240 amino acids to 257 amino acids, of the amino acid sequence depicted in FIG. 8A (*Halorubrum sodomense* archaerhodopsin-3); b) a TS sequence; c) a fluorescent protein; and d) an ER export sequence. For example, a TS sequence can comprise an amino acid sequence having 90%, 91%, 92%, 93%, 94%, 95%, 96%, 97%, 98%, 99%, or 100%, amino acid sequence identity to an amino acid sequence selected from: MDYGGALSAVGRELLFVTNPVVVNGS (SEQ ID NO:6); MAGHSNSMALFSFSLLWLCSGVLGTEF (SEQ ID NO:7); MGLRALMLWLLAAAGLVRESLQG (SEQ ID NO:8); MRGTPLLLVVSLFSLLQD (SEQ ID NO:9); and KSRITSEGEYIPLDQIDINV (SEQ ID NO:10). For example, the ER export sequence is selected from VXXSL (where X is any amino acid) (e.g., VKESL (SEQ ID NO:1); VLGSL (SEQ ID NO:2); etc.); NANSFCYENEVALTSK (SEQ IDNO:3); and FXYENE (SEQ ID NO:4) (where X is any amino acid), e.g., FCYENEV (SEQ ID NO:5).

In some embodiments, a subject variant opsin comprises an amino acid sequence having at least about 85%, or at least about 90%, 91%, 92%, 93%, 94%, 95%, 96%, 97%, 98%, 99%, or 100%, amino acid sequence identity to the amino acid sequence depicted in FIG. 7B.

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 220 amino acids, from about 220 amino acids to about 230 amino acids, from about 230 amino acids to about 240 amino acids, or from about 240 amino acids to 257 amino acids, of the amino acid sequence depicted in FIG. 9A (*Halorubrum sodomense* strain TP009 opsin); b) a TS sequence; and c) an ER export sequence. For example, a TS sequence can comprise an amino acid sequence having 90%, 91%, 92%, 93%, 94%, 95%, 96%, 97%, 98%, 99%, or 100%, amino acid sequence identity to an amino acid sequence selected from: MDYGGALSAVGRELLFVTNPVVVNGS (SEQ ID NO:6); MAGHSNSMALFSFSLLWLCSGVLGTEF (SEQ ID NO:7); MGLRALMLWLLAAAGLVRESLQG (SEQ ID NO:8); MRGTPLLLVVSLFSLLQD (SEQ ID NO:9); and KSRITSEGEYIPLDQIDINV (SEQ ID NO:10). For example, the ER export sequence is selected from VXXSL (where X is any amino acid) (e.g., VKESL (SEQ ID NO:1); VLGSL (SEQ ID NO:2); etc.); NANSFCYENEVALTSK (SEQ ID NO:3); and FXYENE (SEQ ID NO:4) (where X is any amino acid), e.g., FCYENEV (SEQ ID NO:5).

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 220 amino acids, from about 220 amino acids to about 230 amino acids, from about 230 amino acids to about 240 amino acids, or from about 240 amino acids to 257 amino acids, of the amino acid sequence depicted in FIG. 9A (*Halorubrum sodomense* strain TP009 opsin); b) a TS sequence; c) a fluorescent protein; and d) an ER export sequence. For example, a TS sequence can comprise an amino acid sequence having 90%, 91%, 92%, 93%, 94%, 95%, 96%, 97%, 98%, 99%, or 100%, amino acid sequence identity to an amino acid sequence selected from: MDYGGALSAVGRELLFVTNPVVVNGS (SEQ ID NO: 6); MAGHSNSMALFSFSLLWLCSGVLGTEF (SEQ ID NO: 7); MGLRALMLWLLAAAGLVRESLQG (SEQ ID NO: 8); MRGTPLLLVVSLFSLLQD (SEQ ID NO: 9); and KSRITSEGEYIPLDQIDINV (SEQ ID NO: 10). For example, the ER export sequence is selected from VXXSL (where X is any amino acid) (e.g., VKESL (SEQ ID NO: 1); VLGSL (SEQ ID NO: 2); etc.); NANSFCYENEVALTSK (SEQ ID NO: 3); and FXYENE (SEQ ID NO: 4) (where X is any amino acid), e.g., FCYENEV (SEQ ID NO: 5).

In some embodiments, a subject variant opsin comprises an amino acid sequence having at least about 85%, or at least about 90%, 91%, 92%, 93%, 94%, 95%, 96%, 97%, 98%, 99%, or 100%, amino acid sequence identity to the amino acid sequence depicted in FIG. 7C.

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 225 amino acids, from about 225 amino acids to about 250 amino acids, from about 250 amino acids to about 275 amino acids, from about 275 amino acids to about 300 amino acids, or from about 300 amino acids to 313 amino acids, of the amino acid sequence depicted in FIG. 10A (*Leptosphaeria maculans* opsin); and b) an ER export sequence. For example, the ER export sequence is selected from VXXSL (where X is any amino acid) (e.g., VKESL (SEQ ID NO: 1); VLGSL (SEQ ID NO: 2); etc.); NANSFCYENEVALTSK (SEQ ID NO: 3); and FXYENE (SEQ ID NO: 4) (where X is any amino acid), e.g., FCYENEV (SEQ ID NO: 5).

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 225 amino acids, from about 225 amino acids to about 250 amino acids, from about 250 amino acids to about 275 amino acids, from about 275 amino acids to about 300 amino acids, or from about 300 amino acids to 313 amino acids, of the amino acid sequence depicted in FIG. 10A (*Leptosphaeria maculans* opsin); b) a fluorescent protein; and c) an ER export sequence. For example, the ER export sequence is selected from VXXSL (where X is any amino acid) (e.g., VKESL (SEQ ID NO: 1); VLGSL (SEQ ID NO: 2); etc.); NANSFCYENEVALTSK (SEQ ID NO: 3); and FXYENE (SEQ ID NO: 4) (where X is any amino acid), e.g., FCYENEV (SEQ ID NO: 5).

In some embodiments, a subject variant opsin comprises an amino acid sequence having at least about 85%, or at least about 90%, 91%, 92%, 93%, 94%, 95%, 96%, 97%, 98%, 99%, or 100%, amino acid sequence identity to the amino acid sequence depicted in FIG. 7D.

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 225 amino acids, from about 225 amino acids to about 250 amino acids, from about 250 amino acids to about 275 amino acids, from about 275 amino acids to about 300 amino acids, or from about 300 amino acids to 313 amino acids, of the amino acid sequence depicted in FIG. 10A (*Leptosphaeria maculans* opsin); b) a TS sequence; and c) an ER export sequence. For example, a TS sequence can comprise an amino acid sequence having 90%, 91%, 92%, 93%, 94%, 95%, 96%, 97%, 98%, 99%, or 100%, amino acid sequence identity to an amino acid sequence selected from:

```
                                    (SEQ ID NO: 6)
MDYGGALSAVGRELLFVTNPVVVNGS;

(SEQ ID NO: 7)
MAGHSNSMALFSFSLLWLCSGVLGTEF;

(SEQ ID NO: 8)
MGLRALMLWLLAAAGLVRESLQG;

(SEQ ID NO: 9)
MRGTPLLLVVSLFSLLQD;
and
                                    (SEQ ID NO: 10)
KSRITSEGEYIPLDQIDINV.

For example, the ER export sequence is selected
from VXXSL (where X is any amino acid) (e.g.,
VKESL (SEQ ID NO: 1); VLGSL (SEQ ID NO: 2); etc.);
NANSFCYENEVALTSK (SEQ ID NO: 3); and FXYENE (SEQ
ID NO: 4) (where X is any amino acid), e.g.,
FCYENEV (SEQ ID NO: 5).
```

In some embodiments, a subject variant opsin comprises, in order from amino terminus to carboxyl terminus: a) a hyperpolarizing opsin comprising an amino acid sequence having at least about 85%, or at least about 90%, 91%, 92%, 93%, 94%, 95%, 96%, 97%, 98%, 99%, or 100%, amino acid sequence identity to a contiguous stretch of from about 200 amino acids to about 225 amino acids, from about 225 amino acids to about 250 amino acids, from about 250 amino acids to about 275 amino acids, from about 275 amino acids to about 300 amino acids, or from about 300 amino acids to 313 amino acids, of the amino acid sequence depicted in FIG. 10A (*Leptosphaeria maculans* opsin); b) a TS sequence; c) a fluorescent protein; and d) an ER export sequence. For example, a TS sequence can comprise an amino acid sequence having 90%, 91%, 92%, 93%, 94%, 95%, 96%, 97%, 98%, 99%, or 100%, amino acid sequence identity to an amino acid sequence selected from:

```
                                    (SEQ ID NO: 6)
MDYGGALSAVGRELLFVTNPVVVNGS;

(SEQ ID NO: 7)
MAGHSNSMALFSFSLLWLCSGVLGTEF;

(SEQ ID NO: 8)
MGLRALMLWLLAAAGLVRESLQG;
```

-continued

MRGTPLLLVVSLFSLLQD; (SEQ ID NO: 9)
and

KSRITSEGEYIPLDQIDINV. (SEQ ID NO: 10)

For example, the ER export sequence is selected
from VXXSL (where X is any amino acid) (e.g.,
VKESL (SEQ ID NO: 1); VLGSL (SEQ ID NO: 2); etc.);
NANSFCYENEVALTSK (SEQ ID NO: 3); and FXYENE (SEQ
ID NO: 4) (where X is any amino acid), e.g.,
FCYENEV (SEQ ID NO: 5).

In some embodiments, a subject variant opsin comprises an amino acid sequence having at least about 85%, or at least about 90%, 91%, 92%, 93%, 94%, 95%, 96%, 97%, 98%, 99%, or 100%, amino acid sequence identity to the amino acid sequence depicted in FIG. 7E.

Nucleic Acids

The present disclosure provides nucleic acids comprising a nucleotide sequence encoding a subject variant opsin. A nucleotide sequence encoding a subject variant opsin can be operably linked to one or more regulatory elements, such as a promoter and enhancer, that allow expression of the nucleotide sequence in the intended target cells (e.g., a cell that is genetically modified to synthesize the encoded variant opsin). In some cases, the variant opsin-encoding nucleotide sequence is operably linked to a transcriptional control element(s) that provides for neuron-specific expression. In some cases, a nucleotide sequence encoding a subject variant opsin is codon-optimized for expression in a mammalian cell.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a METS promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject opsin can be present in an expression vector and/or a cloning vector. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding a protein of interest (e.g., a variant opsin). A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Also provided herein is a recombinant vector comprising a subject polynucleotide encoding a subject variant opsin or any variant thereof. A subject recombinant vector also include vectors comprising a polynucleotide which encodes an RNA (e.g., an mRNA) that when transcribed from the polynucleotides of the vector will result in the accumulation of a subject opsin on the plasma membranes of target animal cells. Vectors which may be used include, without limitation, lentiviral, HSV, adenoviral, and andeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are

DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" in Parvoviruses (J R Kerr, S F Cotmore. M E Bloom, R M Linden, C R Parrish, Eds.) p5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p15-23, Hudder Arnold, London, UK (2006), the disclosures of which are hereby incorporated by reference herein in their entireties). Methods for purifying for vectors may be found in, for example, U.S. Pat. Nos. 6 566 118, 6 989 264, and 6 995 006 and International Patent Application Publication No.: WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos: WO 91/18088 and WO 93/09239; U.S. Pat. Nos: 4,797,368, 6,596,535, and 5,139,941; and European Patent No: 0488528, all of which are herein incorporated by reference in their entirety). These publications describe various AAV-derived constructs in which the rep and/or cap genes are deleted and replaced by a gene of interest, and the use of these constructs for transferring the gene of interest in vitro (into cultured cells) or in vivo (directly into an organism). A replication defective recombinant AAV can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, a subject recombinant vector is encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535.

As noted above, in some cases, a subject variant opsin-encoding nucleotide sequence is operably linked to a neuron-specific promoter. Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) *Gene Therapy* 11:52-60); a motor neuron-specific gene Hb9 promoter (see, e.g., U.S. Pat. No. 7,632,679; and Lee et al. (2004) *Development* 131:3295-3306); and an alpha subunit of $Ca^{2+}$-calmodulin-dependent protein kinase II (CaMKIIα) promoter (see, e.g., Mayford et al. (1996) *Proc. Natl. Acad. Sci. USA* 93:13250).

Utility

A subject opsin finds use in modulating the voltage potential of a cell. A subject opsin finds use in therapeutic and drug screening applications. A subject opsin finds use in generating disease models.

Modulating the Voltage Potential of a Cell

For example, a subject opsin is useful for modulating the voltage potential of a cell, e.g., a neuron. The cell can be in vitro or in vivo. Thus, e.g., the present disclosure provides a method for adjusting the voltage potential of cells, subcellular regions, or extracellular regions, the method generally involving: introducing a nucleic acid comprising a nucleotide sequence encoding a subject opsin (e.g., a light-driven proton pump) into at least one target cell, subcellular region, or extracellular region, the opsin operating to change transmembrane potential in response to a specific wavelength of light; and causing the expression of the nucleic acid by exposing the target cell, subcellular region, or extracellular region to the specific wavelength of light in a manner designed to cause the voltage potential of the target cell, subcellular region, or extracellular region to increase or decrease.

In some cases, a subject method further involves the step of increasing or decreasing the voltage potential of the target cell, subcellular region, or extracellular region until it is hyperpolarized. Where the target cell, subcellular region, or extracellular region is a neuron, the hyperpolarization achieves neural silencing.

In some cases, a subject method further involves the step of using a plurality of different opsins (e.g., light-activated proton pumps) responsive to different wavelengths of light to achieve multi-color neural silencing by the steps of: expressing each opsin (e.g., light-activated proton pump) in a different population of cells; and illuminating the cells with different colors of light.

The present disclosure provides a method for adjusting the pH of a cell, subcellular region, or extracellular region, the method generally involving: introducing a nucleic acid comprising a nucleotide sequence encoding a subject opsin (e.g., light-driven proton pump) into at least one target cell, subcellular region, or extracellular region, the opsin operating to change cell, subcellular region, or extracellular region pH in response to a specific wavelength of light; and causing the expression of the nucleic acid by exposing the target cell, subcellular region, or extracellular region to the specific wavelength of light in a manner designed to cause the pH of the target cell, subcellular region, or extracellular region to increase or decrease.

The present disclosure provides method for causing cells, subcellular regions, or extracellular regions to release protons as chemical transmitters, the method generally involving: introducing a nucleic acid comprising a nucleotide sequence encoding a subject opsin (e.g., light-driven proton pump) into at least one target cell, subcellular region, or extracellular region, the opsin operating to cause proton release in response to a specific wavelength of light; and causing the expression of the nucleic acid by exposing the target cell, subcellular region, or extracellular region to the specific wavelength of light in a manner designed to cause the target cell, subcellular region, or extracellular region to release protons.

Target Cell-Modulating Applications

In some embodiments, a target cell is genetically modified with a subject nucleic acid (e.g., a nucleic acid comprising a nucleotide sequence encoding an opsin, e.g., a variant opsin). In some cases, target cells are neurons located in the brain of a mammal. The target cells are genetically modified to express a photosensitive opsin, for example, a subject opsin (e.g., a subject variant opsin), as described above. Light can then be used to stimulate the neurons. Depending upon a number of factors, such as the location within the brain and the frequency and length of stimulation, different objectives can be achieved. For instance, current techniques for deep brain stimulus (DBS) use electrodes to apply a current directly to the targeted area of the brain. The frequency of the electrical stimulus is sometimes referred to as either low-frequency DBS or high-frequency DBS. Studies have suggested that high-frequency DBS inhibits the generation of impulses from the stimulated cells, while low-frequency DBS facilitates the generation of impulses from the stimulated cells. The frequencies that produce the effects of high-frequency of low-frequency DBS have also been shown to vary depending upon the specific area of the brain being stimulated. According to one example of high-frequency DBS, the neurons are stimulated using electrodes supplying current pulses at frequencies around 100 Hz or more. Such a frequency has been shown to be effective in certain applications, as discussed further herein.

A specific example of DBS is used for the treatment of Parkinson's disease. In this application, DBS is often applied to the globus pallidus interna, or the subthalamic nucleus within a patient's brain. By implanting a biological arrangement that modifies the cells to respond to light, a light flashing light can be used in place of electrodes. Thus, the targeted neuron cells and external electrical signal need not be directly applied to the targeted cells. Moreover, light can often travel from its point of origin farther than electricity, thereby increasing the effective area relative to the stimulation source and only those neurons that have been photosensitized are stimulated.

As with the electrode-based DBS methods, one embodiment of the present invention can be implemented using high-frequency DBS to inhibit neuron generated impulses. While high-frequency DBS has been accomplished at frequencies around 100 Hz, high-frequency DBS using various embodiments of the present disclosure may not necessarily require the same frequency. For instance, it may be possible to reproduce the inhibiting effects of high-frequency DBS at lower frequencies (e.g., 50 Hz) when using light activated techniques. For example, activation of a hyperpolarizing opsin can result in hyperpolarization and resistance to action potential generation. Various frequencies can be used depending upon the particular application (e.g., the targeted portion of the brain and the desired effect), and the stimulation modality being applied.

Consistent with another example embodiment of the present invention, gene transfer vectors inducing the expression of photosensitive bio-molecules are used to target a specific type of cell. For instance, viral-based proteins (e.g., lentiviruses, adeno-associated viruses or retroviruses) can be created to target specific types of cells, based upon the proteins that they uniquely express. The targeted cells are then infected by the viral-based gene-transfer proteins, and begin to produce a new type of ion channel (for example a subject opsin; a subject variant opsin), thereby becoming photosensitive. This can be particularly useful for stimulating the targeted cells without stimulating other cells that are in proximity to the targeted cells. For example, neurons of disparate length, diameter, chronaxie, other membrane properties, electrical insulation, neurotransmitter output, and overall function, lie in close proximity to one another, and thus, can be inadvertently stimulated when using electrodes to provide the stimulation of the neurons. See, e.g., Gradinaru et al. (2007) *J. Neurosci.* 27(52): 14231-14238, Zhang et al. (2007) *Nature* 446: 633-639, Zhang et al. (2007) *Nature Reviews Neuroscience* Vol. 8: 577-581.

The present disclosure provides an implantable arrangement for in vivo use. A light-emitting diode, laser or similar light source is included for generating light. A biological portion that modifies target cells to include light responsive molecules which facilitate stimulation of the target cells in response to light generated by the light source.

Another embodiment of the present invention employs an arrangement for stimulating target cells using a photosensitive protein that allows the target cells to be stimulated in response to light. A biological delivery device is used for implanting vectors that modify the target cells to include the photosensitive protein. An implantation component (e.g., an implantable component comprising a recombinant expression vector encoding a subject opsin), is used for implanting a light generating device near the target cells. A control device is used for activating the light generating device to generate light to be received by the target cells, thereby stimulating the target cells in response to the generated light.

For example, light can be delivered to a site internal to an organism (e.g., a mammal). A light generator, such as an an implantable device that generates light in vivo, is used. A subject opsin (e.g., a subject variant opsin) present in target cells at the site provides for stimulation of the target cells in response to light generated by the light generator, which light strikes the target cells. The light generator can be a small electronic device on the order of a few millimeters in size. The small size is particularly useful for minimizing the intrusiveness of the device and associated implantation procedure. In another instance, the light generator can include a fiber optic device that can be used to transmit light from an external source to the target cells. For example, the target cells are modified to contain light-activated proton pump/channel proteins.

A subject light-sensitive protein can be implanted using a number of different methods. Example methods include, but are not limited to, the use of various delivery devices, such as gelatin capsules, liquid injections and the like. Such methods also include the use of stereotactic surgery techniques such as frames or computerized surgical navigation systems to implant or otherwise access areas of the body.

As one example, target cells that have been modified to be photosensitive, e.g., modified to produce a subject opsin (e.g., a subject variant opsin). The target cells are thus photosensitive. Stimulation of the target cells can be controlled by the implantable device. For example, a control circuit can be arranged to respond to an external signal by activating, or deactivating a light source, or by charging the battery that powers light source. In one instance, the external signal is electromagnetic radiation that is received by a control circuit. For example, radio frequency (RP) signals can be transmitted by an external radiofrequency (RF) transmitter and received by a control circuit. In another example, a magnetic field can be used to activate and/or power the control circuit.

A control circuit can be implemented using varying degrees of complexity. In one instance, the circuit is a simple coil that when exposed to a magnetic field generates a current. The current is then used to a power light source. Such an implementation can be particularly useful for limiting the size and complexity as well as increasing the longevity of the device. In another instance, a control circuit can include an RF antenna. Optionally, a battery or similar power source, such as a capacitive element, can be used by a control circuit. While charged, the power source allows the circuitry to continue to operate without need for concurrent energy delivery from outside the body. This can be particularly useful for providing precise control over the light emitted by a light source and for increased intensity of the emitted light. In one embodiment, a light source is implemented using a light-emitting-diode (LED). LEDs have been proven to be useful for low power applications and also to have a relatively fast response to electrical signals.

In another embodiment, a matrix (e.g., which can include a gelatin or similar substance) that contains recombinant expression vectors encoding a subject opsin (e.g., a subject variant opsin), which recombinant expression vectors enter target cells and provide for target cell photosensitivity. In one instance, the vectors are released once implanted into the body. This can be accomplished, for example, by using a containment material that allows the vectors to be released into aqueous solution {e.g., using dehydrated or water soluble materials such as gelatins). The release of the vectors results in the target cells being modified such that they are simulated in response to light from a light source.

In another embodiment, a synthetic mesh that contains the photosensitive cells is used. In one instance, the cells are neurons that have been modified to be photosensitive (e.g., modified to include a subject opsin, e.g., a subject variant opsin. The synthetic mesh can be constructed so as to allow the dendrites and axons to pass through the mess without allowing the entire neuron {e.g., the cell body) to pass. One example of such a mesh has pores that are on the order of 3-7 microns in diameter and is made from polyethylene terephthalate. In another example embodiment, an injection mechanism is used to deliver a subject opsin (e.g., a subject variant opsin), e.g., a recombinant expression vector encoding a subject opsin.

For example, an implantable device can be responsive to a magnetic field. For example, an inductor generates a current/Voltage in response to a magnetic field. The current is passed to a control circuit through a conductive path. In response, a control circuit activates a light source using a conductive path. A light source illuminates a biological portion in order to stimulate the target cells. In one instance, the biological portion includes a gelatin, synthetic mesh, or injection mechanism as discussed above.

In one embodiment, the control portion can be a simple electrical connection, resistive element, or can be removed completely. In such an embodiment, the intensity, duration and frequency of light generated would be directly controlled by the current generated from a magnetic field. This can be particularly useful for creating inexpensive, long lasting and small devices.

In another embodiment, the control portion can be implemented as a more complex circuit. For instance the control circuit may include and otherwise implement different rectifier circuits, batteries, pulse timings, comparator circuits and the like. In a particular example, the control circuit includes an integrated circuit (IC) produced using CMOS or other processes. Integrated circuit technology allows for the use of a large number of circuit elements in a very small area, and thus, a relatively complex control circuit can be implemented for some applications.

As an example, an inductor is a surface mount inductor, such as a 100 uH inductor part number CF1008-103K supplied by Gowanda Electronics Corp. The light generating portion is a blue LED, such as LEDs in 0603 or 0805 package sizes. A particular example is a blue surface mount LED having part number SML0805, available from LEDtronics, Inc (Torrance, Calif.). Connective paths can be implemented using various electrical conductors, such as conductive epoxies, tapes, solder or other adhesive materials. LEDs emitting light in the appropriate spectrum (as applicable to a subject opsin) are available through commercial sources including this same manufacturer.

The present disclosure provides a method for genetically modifying neurons to express a light-sensitive opsin described herein. For example, a subject opsin can be used to impart photosensitivity upon mammalian nerve cells, by using an expression vector to deliver a nucleic acid encoding a subject opsin into targeted nerve cells, which subsequently produce the encoded opsin. Stimulation of the target cells with light results in hyperpolarization of the target cells.

The present disclosure provides methods for generating an inhibitory neuron-current flow in a neuron, the methods involving modifying the neuron to express a subject opsin;

and exposing the neuron to a light stimulus. The present disclosure provides methods for controlling action potential of a neuron, the methods involving modifying the neuron to express a subject opsin; and exposing the neuron to a light stimulus. The present disclosure provides methods for controlling a voltage level across a cell membrane of a cell, the methods involving modifying the cell to express a subject opsin; and exposing the cell to a light stimulus.

The present disclosure provides a system for controlling an action potential of a neuron in vivo. The system includes a delivery device, a light source, and a control device. The delivery device introduces a light responsive protein (a subject opsin) to the neuron, with the light responsive protein producing an inhibitory current. The light source generates light for stimulating the light responsive protein, and the control device controls the generation of light by the light source.

The present disclosure provides methods of treating a disorder. The method targets a group of neurons associated with the disorder; the target neurons are modified to express a subject opsin; the modified target neurons produce an inhibitory current that reduces depolarization of the neurons; the modified neurons are exposed to a light stimulus, thereby reducing depolarization of the neurons.

Drug Screening

Certain embodiments of the present invention can be useful in drug screening. The various light-sensitive proteins, serving to regulate membrane voltage using ion switches that, when activated (or deactivated) in response to light, function as channels or pumps and are referred to hereafter as light-responsive ion switches or light-activated membrane potential switches (LAMPS).

For example, the present disclosure provides for screening for ion-channel and ion-pump affecting compounds. The system introduces one or more drug candidates that could either block or enhance the activity of a subject opsin in a cell modified to synthesize a subject opsin. Light triggers optically responsive ion channels in the cells causing a change in the voltage seen across the cell membrane. The voltage change stimulates voltage-gated ion channels in the cells which will then cause a change in ion concentrations that can be read as optical outputs. These optical signals are detected and used to determine what effect, if any, the drug candidates have on the voltage-gated ion channels. In a more specific embodiment a protein expressing a proton pump is introduced into the cell.

In one instance, the system allows for different drug candidates to be screened without necessitating extensive setup between screenings. For example, an assay may be performed using optics both to stimulate the optically responsive cells and to detect the effectiveness of the drug. The use of optics instead of manual contacts, e.g., using a whole-cell patch clamp, can be particularly useful in increasing the throughput of the assay screening process. For instance, the time between screenings can be reduced by minimizing or eliminating physical manipulations otherwise necessary to stimulate or detect ion flow in the target cells. The cells can also be prepared prior to the screening process because the test equipment need only be optically coupled to the prepared cells. In another instance, throughput may be increased by screening a number of different drugs simultaneously using, for example, an array of photo detectors and a corresponding array of modified cells exposed to different drugs.

Optical stimulation of the modified cells can be altered to determine specific properties of an introduced drug candidate. For example, the intensity of the optical stimulus may be modified to change the corresponding level of depolarization. The level of desired depolarization can be tuned to further characterize the effectiveness of the drug under test. In another example, the optical stimulus may include rapid pulsing of the light. By correlating the temporal relationship between the optical stimulus and the resultant detected fluorescence, the drug may be further characterized in terms of a kinetic response. Thus, the drug may be characterized for a variety of different aspects including, but not limited to, the steady state effect on ion concentrations, a change in the level of depolarization necessary to open voltage gated ion channels, and the effect on repeated depolarization.

In one embodiment, the system allows for simple calibration of the optical stimulation and/or detection. The modified cells may be optically stimulated prior to introduction of the drug candidate. The ion channel responsiveness is detected and recorded. The recorded values may be used as a baseline for comparison to the ion channel responsiveness of the same modified cells after the introduction of the drug under test. The recorded values may also be used to modify the optical stimulus or the sensitivity of the optical detector. Such modifications may be applied to an individual test sample or an array of test samples. For such an array of test samples, each test sample may be individually calibrated by adjusting the corresponding optical stimulus. Similarly, each corresponding photo detector may be individually adjusted.

The amount of time allotted for light delivery may vary, and depends on factors including the level of light-gated proton or ion channel/pump expression, and the density and characteristics of other proton/ionic channel characteristics of that cell population. The amount of time allotted for light receipt may vary, and depends upon factors including the degree of accuracy required for the screening session. The amount of time allotted for well-plate (tray) changing may vary, and depends upon factors including the mechanical speed of the automated apparatus. If fast neurons are used as the cells being tested, the cellular stimulation and LEIA detection process may be accomplished in milliseconds.

The process above may be repeated under varying conditions. For example, a given set of cells may be tested with no drug present, and subsequently with one or more drugs present. The response of electrically-excitable cells under those conditions may be thereby documented, compared and studied. If the invention is implemented with at least one emitter/detector for each well on a tray and at least two concurrently operating devices, continuous operation may be maintained for extended periods of time.

Exemplary screening methods could include the collection of multiple data points without having to switch samples. Because control over the samples is reversible in the same sample preparation by simply turning the activating light on and off with fast shutters, the same samples can be reused. Further, a range of patterns of stimulation can be provided to the same cell sample so that testing can be performed for the effect of drugs without concern with regards to differences across different sample preparations. By modulating the level of excitation (e.g., by ramping the level from no light to a high or maximum intensity), the effect of the drug across a range of membrane potentials can be tested. This permits for the identification of drugs that are efficacious during hyperpolarized, natural, or depolarized membrane potentials.

The cell lines described herein may be a particularly useful for detailed characterization of drug candidates in a high-throughput manner. Optical control is relatively fast, thereby allowing for the testing the drug's activity under more physiological forms of activation. For example, different frequencies of depolarization and/or hyperpolarization may be used to determine how a drug interacts with the channel under physiological forms of neural activity. In some instances, the process may be accomplished without the application of expensive chemical dyes to the cell lines.

In conjunction with the various properties discussed herein, the use of various embodiments of the invention may be particularly useful for improving screening throughput by eliminating the need for cumbersome mechanical manipulation and liquid handling. Various embodiments may also be useful for repeatable the screening assay using the same samples, reducing screening cost by eliminating the need for chemically-based fluorescence reports, producing high temporal precision and low signal artifact (due to the optical nature of the voltage manipulation), modulating the level of depolarization by attenuating the light intensity used for stimulation, and ascertaining the kinetics of the drug's modulation on the ion channel through the use of pulsed light patterns.

The existence of multiple independently controllable excitation proteins and inhibition proteins opens the door for a variety of applications including, but not limited to, applications for treatment of a variety of disorders and the use of a plurality of light-responsive proteins that can be selected so as to respond to a plurality of respective optical wavelengths. Although not always expressly stated, inhibition can be used in combination with, in addition to, or in place of excitation in the applications. The family of single-component proteins has been shown to respond to multiple wavelengths and intensities of light. Aspects of the disclosure allow for further mutations and/or searches for sequences that allow for additional optical wavelengths and/or individually controllable protein channels. Variations on the optical stimulus (e.g., a wavelength, intensity or duration profile) can also be used. For instance, stimulation profiles may exploit overlaps in the excitation wavelengths of two different ion channel proteins to allow excitation of both proteins at the same time. In one such instance, the proteins may have different levels of responsibility. Thus, in a neural application, one set of ion channels may produce spiking at a different success percentage relative to a second set of ion channels Similarly, the overlaps in inhibition wavelengths of two different ion channels (or pumps) allows for inhibition of both proteins at the same time.

Alternatively, multiple light sources may be used allowing for stimulations of the light responsive proteins in the combination desired, while leaving other proteins unstimulated.

Therapeutic Applications

The present disclosure provides various therapeutic methods.

Addiction is associated with a variety of brain functions, including reward and expectation. Additionally, the driving cause of addiction may vary between individuals. According to one embodiment, addiction, for example nicotine addiction, may be treated with optogenetic stabilization of small areas on the insula. Optionally, functional brain imaging, for example cued-state PET or fMRI, may be used to locate a hyper metabolic focus in order to determine a precise target spot for the intervention on the insula surface.

Optogenetic excitation of the nucleus accumbens and septum may provide reward and pleasure to a patient without need for resorting to use of substances, and hence may hold a key to addiction treatment. Conversely, optogenetic stabilization of the nucleus accumbens and septum may be used to decrease drug craving in the context of addiction. In an alternative embodiment, optogenetic stabilization of hyper metabolic activity observed at the genu of the anterior cingulate (BA32) can be used to decrease drug craving. Optogenetic stabilization of cells within the arcuate nucleus of the medial hypothalamus which contain peptide products of pro-opiomelanocortin (POMC) and cocaine-and-amphetamine-regulating transcript (CART) can also be used to decrease drug addiction behavior.

Optogenetic stimulation of neuroendocrine neurons of the hypothalamic periventricular nucleus that secrete somatostatin can be used to inhibit secretion of growth hormone from the anterior pituitary, for example in acromegaly. Optogenetic stabilization of neuroendocrine neurons that secrete somatostatin or growth hormone can be used to increase growth and physical development. Among the changes that accompany "normal" aging, is a sharp decline in serum growth hormone levels after the $4^{th}$ and $5^{th}$ decades. Consequently, physical deterioration associated with aging may be lessened through optogenetic stabilization of the periventricular nucleus.

Optogenetic stabilization of the ventromedial nucleus of the hypothalamus, particularly the pro-opiomelanocortin (POMC) and cocaine-and-amphetamine-regulating transcript (CART) of the arcuate nucleus, can be used to increase appetite, and thereby treat anorexia nervosa. Alternatively, optogenetic stimulation of the lateral nuclei of the hypothalamus can be used to increase appetite and eating behaviors.

Optogenetic excitation in the cholinergic cells of affected areas including the temporal lobe, the NBM (Nucleus basalis of Meynert) and the posterior cingulate gyrus (BA 31) provides stimulation, and hence neurotrophic drive to deteriorating areas.

Because the affected areas are widespread within the brain, an analogous treatment with implanted electrodes may be less feasible than an opto-genetic approach.

Anxiety disorders are typically associated with increased activity in the left temporal and frontal cortex and amygdala, which trends toward normal as anxiety resolves. Accordingly, the affected left temporal and frontal regions and amygdala may be treated with optogenetic stabilization, so as to dampen activity in these regions.

In normal physiology, photosensitive neural cells of the retina, which depolarize in response to the light that they receive, create a visual map of the received light pattern. Optogenetic ion channels can be used to mimic this process in many parts of the body, and the eyes are no exception. In the case of visual impairment or blindness due to damaged retina, a functionally new retina can be grown, which uses natural ambient light rather than flashing light patterns from an implanted device. The artificial retina grown may be placed in the location of the original retina (where it can take advantage of the optic nerve serving as a conduit back to the visual cortex). Alternatively, the artificial retina may be placed in another location, such as the forehead, provided that a conduit for the depolarization signals are transmitted to cortical tissue capable of deciphering the encoded information from the optogenetic sensor matrix. Cortical blindness could also be treated by simulating visual pathways downstream of the visual cortex. The stimulation would be based on visual data produced up stream of the visual cortex or by an artificial light sensor.

Treatment of tachycardia may be accomplished with optogenetic stimulation to parasympathetic nervous system fibers including CN X or Vagus Nerve. This causes a decrease in the S A node rate, thereby decreasing the heart rate and force of contraction. Similarly, optogenetic stabilization of sympathetic nervous system fibers within spinal nerves T1 through T4, serves to slow the heart. For the treatment of pathological bradycardia, optogenetic stabilization of the Vagus nerve, or optogenetic stimulation of sympathetic fibers in T1 through T4 will serve to increase heart rate. Cardiac disrhythmias resulting from aberrant electrical foci that outpace the sinoatrial node may be suppressed by treating the aberrant electrical focus with moderate optogenetic stabilization. This decreases the intrinsic rate of firing within the treated tissue, and permits the sinoatrial node to regain its role in pacing the heart's electrical system. In a similar way, any type of cardiac arrhythmia could be treated. Degeneration of cardiac tissue that occurs in cardiomyopathy or congestive heart failure could also be treated using this invention; the remaining tissue could be excited using various embodiments of the invention.

Optogenetic excitation stimulation of brain regions including the frontal lobe, parietal lobes and hippocampi, may increase processing speed, improve memory, and stimulate growth and interconnection of neurons, including spurring development of neural progenitor cells. As an example, one such application of the present invention is directed to optogenetic excitation stimulation of targeted neurons in the thalamus for the purpose of bringing a patient out of a near- vegetative (barely-conscious) state. Growth of light-gated ion channels or pumps in the membrane of targeted thalamus neurons is affected. These modified neurons are then stimulated (e.g., via optics which may also gain access by the same passageway) by directing a flash of light thereupon so as to modulate the function of the targeted neurons and/or surrounding cells.

In an alternative embodiment, optogenetic excitation may be used to treat weakened cardiac muscle in conditions such as congestive heart failure. Electrical assistance to failing heart muscle of CHF is generally not practical, due to the thin-stretched, fragile state of the cardiac wall, and the difficulty in providing an evenly distributed electrical coupling between an electrodes and muscle. For this reason, methods to date for increasing cardiac contractility have involved either pharmacological methods such as Beta agonists, and mechanical approaches such as ventricular assist devices. In this embodiment of the present invention, optogenetic excitation is delivered to weakened heart muscle via light emitting elements on the inner surface of a jacket surround the heart or otherwise against the affected heart wall. Light may be diffused by means well known in the art, to smoothly cover large areas of muscle, prompting contraction with each light pulse.

Optogenetic stabilization in the subgenual portion of the cingulate gyms (Cg25), yellow light may be applied with an implanted device. The goal would be to treat depression by suppressing target activity in manner analogous to what is taught by Mayberg H S et al, "Deep Brain Stimulation for Treatment-Resistant Depression," Neuron, Vol. 45, 651-660, Mar. 3, 2005, pp. 651-660, which is fully incorporated herein by reference. In an alternative embodiment, an optogenetic excitation stimulation method is to increase activity in that region in a manner analogous to what is taught by Schlaepfer et al., "Deep Brain stimulation to Reward Circuitry Alleviates Anhedonia in Refractory Major Depression," Neuropsychopharmacology 2007, pp. 1-10, which is fully incorporated herein by reference.

In yet another embodiment, the left dorsolateral prefrontal cortex (LDPFC) is targeted with an optogenetic excitation stimulation method. Pacing the LDLPFC at 5-20 Hz serves to increase the basal metabolic level of this structure which, via connecting circuitry, serves to decrease activity in Cg 25, improving depression in the process. Suppression of the right dorsolateral prefrontal cortex (RDLPFC) is also an effective depression treatment strategy. This may be accomplished by optogenetic stabilization on the RDLPFC, or suppression may also be accomplished by using optogenetic excitation stimulation, and pulsing at a slow rate (e.g. 1 Hz or less) improving depression in the process. Vagus nerve stimulation (VNS) may be improved using an optogenetic approach. Use of optogenetic excitation may be used in order to stimulate only the vagus afferents to the brain, such as the nodose ganglion and the jugular ganglion.

Efferents from the brain would not receive stimulation by this approach, thus eliminating some of the side-effects of VNS including discomfort in the throat, a cough, difficulty swallowing and a hoarse voice. In an alternative embodiment, the hippocampus may be optogenetically excited, leading to increased dendritic and axonal sprouting, and overall growth of the hippocampus. Other brain regions implicated in depression that could be treated using this invention include the amygdala, accumbens, orbitofrontal and orbitomedial cortex, hippocampus, olfactory cortex, and dopaminergic, serotonergic, and noradrenergic projections. Optogenetic approaches could be used to control spread of activity through structures like the hippocampus to control depressive symptoms.

So long as there are viable alpha and beta cell populations in the pancreatic islets of Langerhans, the islets can be targeted for the treatment of diabetes. For example, when serum glucose is high (as determined manually or by closed loop glucose detection system), optogenetic excitation may be used to cause insulin release from the beta cells of the islets of Langerhans in the pancreas, while optogenetic stabilization is used to prevent glucagon release from the alpha cells of the islets of Langerhans in the pancreas. Conversely, when blood sugars are too low (as determined manually or by closed loop glucose detection system), optogenetic stabilization may be used to stop beta cell secretion of insulin, and optogenetic excitation may be used to increase alpha-cell secretion of glucagon.

For treatment of epilepsy, quenching or blocking epileptogenic activity is amenable to optogenetic approaches. Most epilepsy patients have a stereotyped pattern of activity spread resulting from an epileptogenic focus. Optogenetic stabilization could be used to suppress the abnormal activity before it spreads or truncated it early in its course. Alternatively, activation of excitatory tissue via optogenetic excitation stimulation could be delivered in a series of deliberately asynchronous patterns to disrupt the emerging seizure activity. Another alternative involves the activation of optogenetic excitation stimulation in GABAergic neurons to provide a similar result. Thalamic relays may be targeted with optogenetic stabilization triggered when an abnormal EEG pattern is detected.

Another embodiment involves the treatment of gastrointestinal disorders. The digestive system has its own, semi-autonomous nervous system containing sensory neurons, motor neurons and interneurons. These neurons control movement of the GI tract, as well as trigger specific cells in the gut to release acid, digestive enzymes, and hormones including gastrin, cholecystokinin and secretin. Syndromes that include inadequate secretion of any of these cellular products may be treated with optogenetic stimulation of the producing cell types, or neurons that prompt their activity.

Conversely, optogenetic stabilization may be used to treat syndromes in which excessive endocrine and exocrine products are being created. Disorders of lowered intestinal motility, ranging from constipation (particularly in patients with spinal cord injury) to megacolan may be treated with optogenetic excitation of motor neurons in the intestines.

Disorders of intestinal hypermotility, including some forms of irritable bowel syndrome may be treated with optogenetic stabilization of neurons that control motility.

Neurogenic gastric outlet obstructions may be treated with optogenetic stabilization of neurons and musculature in the pylons. An alternative approach to hypomobility syndromes would be to provide optogenetic excitation to stretch-sensitive neurons in the walls of the gut, increasing the signal that the gut is full and in need of emptying.

In this same paradigm, an approach to hypermobility syndromes of the gut would be to provide optogenetic stabilization to stretch receptor neurons in the lower GI, thus providing a "false cue" that the gut was empty, and not in need of emptying. In the case of frank fecal incontinence, gaining improved control of the internal and external sphincters may be preferred to slowing the motility of the entire tract. During periods of time during which a patient needs to hold feces in, optogenetic excitation of the internal anal sphincter will provide for retention. Providing optogenetic stimulation to the external sphincter may be used to provide additional continence. When the patient is required to defecate, the internal anal sphincter, and then external anal sphincter should be relaxed, either by pausing the optogenetic stimulation, or by adding optogenetic stabilization.

Conductive hearing loss may be treated by the use of optical cochlear implants. Once the cochlea has been prepared for optogenetic stimulation, a cochlear implant that flashes light may be used. Sensorineural hearing loss may be treated through optical stimulation of downstream targets in the auditory pathway.

Another embodiment of the present invention is directed toward the treatment of blood pressure disorders, such as hypertension. Baroreceptors and chemoreceptors in regions such as the aorta (aortic bodies and paraaortic bodies) and the carotid arteries ("carotic bodies") participate in the regulation of blood pressure and respiration by sending afferents via the vagus nerve (CN X), and other pathways to the medulla and pons, particularly the solitary tract and nucleus. Optogenetic excitation of the carotid bodies, aortic bodies, paraortic bodies, may be used to send a false message of "hypertension" to the solitary nucleus and tract, causing it to report that blood pressure should be decreased. Optogenetic excitation or stabilization directly to appropriate parts of the brainstem may also be used to lower blood pressure. The opposite modality causes the optogenetic approach to serve as a pressor, raising blood pressure. A similar effect may also be achieved via optogenetic excitation of the Vagus nerve, or by optogenetic stabilization of sympathetic fibers within spinal nerves T1-T4. In an alternative embodiment, hypertension may be treated with optogenetic stabilization of the heart, resulting in decreased cardiac output and lowered blood pressure. According to another embodiment, optogenetic stabilization of aldosterone-producing cells within the adrenal cortex may be used to decrease blood pressure. In yet another alternative embodiment, hypertension may be treated by optogenetic stabilization of vascular smooth muscle. Activating light may be passed transcutaneousiy to the peripheral vascular bed.

Another example embodiment is directed toward the treatment of hypothalamic-pituitary-adrenal axis disorders. In the treatment of hypothyroidism, optogenetic excitation of parvocellular neuroendocrine, neurons in the paraventricular and anterior hypothalamic nuclei can be used to increase secretion of thyrotropin-releasing hormone (TRH). TRH, in turn, stimulates anterior pituitary to secrete TSH. Conversely, hyperthyroidism may be treated with optogenetic stabilization of the provocellular neuroendocrine neurons. For the treatment of adrenal insufficiency, or of Addison's disease, optogenetic excitation of parvocellular neuroendocrine neurons in the supraoptic nucleus and paraventricular nuclei may be used to increase the secretion of vasopressin, which, with the help of corticotropin-releasing hormone (CRH), stimulate anterior pituitary to secrete ACTH. Cushing syndrome, frequently caused by excessive ACTH secretion, may be treated with optogenetic stabilization of the parvocellular neuroendocrine neurons of supraoptic nucleus via the same physiological chain of effects described above. Neuroendocrine neurons of the arcuate nucleus produce dopamine, which inhibits secretion of prolactin from the anterior pituitary. Hyperprolactinemia can therefore be treated via optogenetic excitation, while hypoprolactinemia can be treated with optogenetic stabilization of the neuroendocrine cells of the arcuate nucleus.

In the treatment of hyperautonomic states, for example anxiety disorders, optogenetic stabilization of the adrenal medulla may be used to reduce norepinephrine output. Similarly, optogenetic stimulation of the adrenal medulla may be used in persons with need for adrenaline surges, for example those with severe asthma, or disorders that manifest as chronic sleepiness.

Optogenetic stimulation of the adrenal cortex will cause release of chemicals including Cortisol, testosterone, and aldosterone. Unlike the adrenal medualla, the adrenal cortex receives its instructions from neuroendocrine hormones secreted from the pituitary and hypothalamus, the lungs, and the kidneys. Regardless, the adrenal cortex is amenable to optogenetic stimulation. Optogenetic stimulation of the cortisol-producing cells of the adrenal cortex may be used to treat Addison's disease. Optogenetic stabilization of cortisol-producing cells of the adrenal cortex may be used to treat Cushing's disease. Optogenetic stimulation of testosterone-producing cells may be used to treat disorders of sexual interest in women: Optogenetic stabilization of those same cells may be used to decrease facial hair in women. Optogenetic stabilization of aldosterone-producing cells within the adrenal cortex may be used to decrease blood pressure. Optogenetic excitation of aldosterone- producing cells within the adrenal cortex may be used to increase blood pressure.

Optogenetic excitation stimulation of specific affected brain regions may be used to increase processing speed, and stimulate growth and interconnection of neurons, including spurring the maturation of neural progenitor cells. Such uses can be particularly useful for treatment of mental retardation.

According to another embodiment, various muscle diseases and injuries can be treated. Palsies related to muscle damage, peripheral nerve damage and to dystrophic diseases can be treated with optogenetic excitation to cause contraction, and optogenetic stabilization to cause relaxation. This latter relaxation via optogenetic stabilization approach can also be used to prevent muscle wasting, maintain tone, and permit coordinated movement as opposing muscle groups are contracted. Likewise, frank spasticity can be treated via optogenetic stabilization.

In areas as diverse as peripheral nerve truncation, stroke, traumatic brain injury and spinal cord injury, there is a need to foster the growth of new neurons, and assist with their integration into a functional network with other neurons and with their target tissue. Re-growth of new neuronal tracts may be encouraged via optogenetic excitation, which serves to signal stem cells to sprout axons and dendrites, and to integrate themselves with the network. Use of an optogenetic technique (as opposed to electrodes) prevents receipt of signals by intact tissue, and serves to ensure that new target tissue grows by virtue of a communication set up with the developing neurons, and not with an artificial signal like current emanating from an electrode.

Obesity can be treated with optogenetic excitation to the ventromedial nucleus of the hypothalamus, particularly the pro-opiomelanocortin (POMC) and cocaine-and-amphetamine-regulating transcript (CART) of the arcuate nucleus. In an alternative embodiment, obesity can be treated via optogenetic stabilization of the lateral nuclei of the hypothalamus. In another embodiment, optogenetic stimulation to leptin-producing cells or to cells with leptin receptors within the hypothalamus may be used to decrease appetite and hence treat obesity.

Destructive lesions to the anterior capsule and analogous DBS to that region are established means of treating severe, intractable obsessive-compulsive disorder 48 (OCD48). Such approaches may be emulated using optogenetic stabilization to the anterior limb of the internal capsule, or to regions such as BA32 and Cg24 which show metabolic decrease as OCD remits.

Chronic pain can be treated using another embodiment of the present disclosure. Electrical stimulation methods include local peripheral nerve stimulation, local cranial nerve stimulation and "sub threshold" motor cortex stimulation. Reasonable autogenic approaches include optogenetic stabilization at local painful sites. Attention to promoter selection would ensure that other sensory and motor fibers would be unaffected.

Selective optogenetic excitation of interneurons at the primary motor cortex also may provide effective pain relief. Also, optogenetic stabilization at the sensory thalamus, (particularly medial thalamic nuclei), periventricular grey matter, and ventral raphe nuclei, may be used to produce pain relief. In an alternative embodiment, optogenetic stabilization of parvalbumin-expressing cells targeting as targeting strategy, may be used to treat pain by decreasing Substance P production. The release of endogenous opiods may be accomplished by using optogenetic excitation to increase activity in the nucleus accumbens. In an alternative embodiment, when POMC neurons of the arcuate nucleus of the medial hypothalamus are optogenetically excited, beta endorphin are increased, providing viable treatment approaches for depression and for chronic pain.

Certain personality disorders, including the borderline and antisocial types, demonstrate focal deficits in brain disorders including "hypofrontality." Direct or indirect optogenetic excitation of these regions is anticipated to produce improvement of symptoms. Abnormal bursts of activity in the amygdala are also known to precipitate sudden, unprompted flights into rage: a symptom of borderline personality disorder, as well as other conditions, which can benefit from optogenetic stabilization of the amygdala. Optogenetic approaches could improve communication and synchronization between different parts of the brain, including amygdala, striatum, and frontal cortex, which could help in reducing impulsiveness and improving insight.

The amygdalocentric model of post-traumatic-stress disorder (PTSD) proposes that it is associated with hyperarousal of the amygdala and insufficient top-down control by the medial prefrontal cortex and the hippocampus. Accordingly, PTSD may be treated with optogenetic stabilization of the amygdale or hippocampus.

Schizophrenia is characterized by abnormalities including auditory hallucinations. These might be treated by suppression of the auditory cortex using optogenetic stabilization. Hypofrontality associated with schizophrenia might be treated with optogenetic excitation in the affected frontal regions. Optogenetic approaches could improve communication and synchronization between different parts of the brain which could help in reducing misattribution of self-generated stimuli as foreign.

Optogenetic stabilization of cells within the arcuate nucleus of the medial hypothalamus, which contain peptide products of pro-opiomelanocortin (POMC) and cocaine-and-amphetamine-regulating transcript (CART), can be used to reduce compulsive sexual behavior. Optogenetic excitation of cells within the arcuate nucleus of the medial hypothalamus which contain peptide products of pro-opiomelanocortin (POMC) and cocaine-and-amphetamine-regulating transcript (CART) may be used to increase sexual interest in the treatment of cases of disorders of sexual desire. In the treatment of disorders of hypoactive sexual desire testosterone production by the testes and the adrenal glands can be increased through optogenetic excitation of the pituitary gland. Optogenetic excitation of the nucleus accumbens can be used for the treatment of anorgasmia.

The suprachiasmatic nucleus secretes melatonin, which serves to regulate sleep/wake cycles. Optogenetic excitation to the suprachiasmic nucleus can be used to increase melatonin production, inducing sleep, and thereby treating insomnia. Orexin (hypocretin) neurons strongly excite numerous brain nuclei in order to promote wakefulness. Optogenetic excitation of orexin-producing cell populations can be used to treat narcolepsy, and chronic daytime sleepiness.

Optogenetic stimulation of the supraoptic nucleus may be used to induce secretion of oxytocin, can be used to promote parturition during childbirth, and can be used to treat disorders of social attachment.

Like muscular palsies, the motor functions that have been de-afferented by a spinal cord injury may be treated with optogenetic excitation to cause contraction, and optogenetic stabilization to cause relaxation. This latter relaxation via optogenetic stabilization approach may also be used to prevent muscle wasting, maintain tone, and permit coordinated movement as opposing muscle groups are contracted. Likewise, frank spasticity may be treated via optogenetic stabilization. Re-growth of new spinal neuronal tracts may be encouraged via optogenetic excitation, which serves to signal stem cells to sprout axons and dendrites, and to integrate themselves with the network.

Stroke deficits include personality change, motor deficits, sensory deficits, cognitive loss, and emotional instability. One strategy for the treatment of stroke deficits is to provide optogenetic stimulation to brain and body structures that have been deafferented from excitatory connections. Similarly, optogenetic stabilization capabilities can be imparted on brain and body structures that have been deafferented from inhibitory connections.

Research indicates that the underlying pathobiology in Tourette's syndrome is a phasic dysfunction of dopamine transmission in cortical and subcortical regions, the thalamus, basal ganglia and frontal cortex. In order to provide therapy, affected areas are preferably first identified using techniques including functional brain imaging and magnetoencephalography (MEG). Whether specifically identified or not, optogenetic stabilization of candidate tracts may be used to suppress motor tics. Post-implantation empirical testing of device parameters reveals which sites of optogenetic stabilization, and which are unnecessary to continue.

In order to selectively excite/inhibit a given population of neurons, for example those involved in the disease state of an illness, several strategies can be used to target the optogenetic proteins/molecules to specific populations.

For various embodiments of the present invention, genetic targeting may be used to express various optogenetic proteins or molecules. Such targeting involves the targeted expression of the optogenetic proteins/molecules via genetic control elements such as promoters (e.g., Parvalbumin, Somatostatin, Cholecystokinin, GFAP), enhancers/silencers (e.g., Cytomaglovirus Immediate Early Enhancer), and other transcriptional or translational regulatory elements (e.g., Woodchuck Hepatitis Virus Post-transcriptional Regulatory Element). Permutations of the promoter+enhancer+regulatory element combination can be used to restrict the expression of optogenetic probes to genetically-defined populations.

Various embodiments of the present invention may be implemented using spatial/anatomical targeting. Such targeting takes advantage of the fact that projection patterns of neurons, virus or other reagents carrying genetic information (DNA plasmids, fragments, etc.), can be focally delivered to an area where a given population of neurons project to. The genetic material will then be transported back to the bodies of the neurons to mediate expression of the optogenetic probes. Alternatively, if it is desired to label cells in a focal region, viruses or genetic material may be focally delivered to the interested region to mediate localized expression.

Gene Delivery Systems

Various gene delivery systems are useful in implementing one or more embodiments of the present disclosure. One such delivery system is Adeno-Associated Virus (AAV). AAV can be used to deliver a promoter+optogenetic probe (opsin) cassette to a specific region of interest. As used herein, "optogenetic probe" refers to an opsin, e.g., an opsin, or a variant opsin, of the present disclosure. The choice of promoter will drive expression in a specific population of neurons. For example, using the CaMKIIα promoter will drive excitatory neuron specific expression of optogenetic probes. AAV will mediate long-term expression of the optogenetic probe (opsin) for at least one year or more. To achieve more specificity, AAV may be pseudotyped with specific serotypes 1, 2, 3, 4, 5, 6, 7, and 8, with each having different tropism for different cell types. For instance, serotype 2 and 5 is known to have good neuron-specific tropism.

Another gene delivery mechanism is the use of a retrovirus. HIV or other lentivirus-based retroviral vectors may be used to deliver a promoter+optogenetic probe cassette to a specific region of interest. Retroviruses may also be pseudo-typed with the Rabies virus envelope glycoprotein to achieve retrograde transport for labeling cells based on their axonal projection patterns. Retroviruses integrate into the host cell's genome, therefore are capable of mediating permanent expression of the optogenetic probes. Non-lentivirus based retroviral vectors can be used to selectively label dividing cells.

Gutless Adenovirus and Herpes Simplex Virus (HSV) are two DNA-based viruses that can be used to deliver promoter+optogenetic probe cassette into specific regions of the brain as well. HSV and Adenovirus have much larger packaging capacities and therefore can accommodate much larger promoter elements and can also be used to deliver multiple optogenetic probes or other therapeutic genes along with optogenetic probes.

Focal Electroporation can also be used to transiently transfect neurons. DNA plasmids or fragments can be focally delivered into a specific region of the brain. By applying mild electrical current, surrounding local cells will receive the DNA material and expression of the optogenetic probes.

In another instance, lipofection can be used by mixing genetic material with lipid reagents and then subsequently injected into the brain to mediate transfection of the local cells.

Various embodiments involve the use of various control elements. In addition to genetic control elements, other control elements (particularly promoters and enhancers whose activities are sensitive to chemical, magnetic stimulation or infrared radiation) can be used to mediate temporally-controlled expression of the optogenetic probes. For example, a promoter whose transcriptional activity is subject to infrared radiation allows one to use focused radiation to fine tune the expression of optogenetic probes in a focal region at only the desired time.

Parkinson's Disease can be treated by expressing optogenetic stabilization in the glutamatergic neurons in either the subthalamic nucleus (STN) or the globus pallidus interna (GPi) using an excitatory-specific promoter such as CaMKIIa, and apply optogenetic stabilization. Unlike electrical modulation in which all cell-types are affected, only glutamatergic STN neurons would be suppressed.

Disease Models

Aspects of the present disclosure provide for testing a model of a neural circuit or disease. The model can define output response of the circuit as a function of input signals. The output response can be assessed using a number of different measurable characteristics. For instance, characteristics can include an electrical response of downstream neurons and/or behavioral response of a patient. To test the model, optogenetic probes are expressed at an input position for the model. The optogenetic probes are stimulated and the output characteristics are monitored and compared to an output predicted by the model.

In certain implementations, the use of optogenetic probes allows for fine tuning of models defined using electrical probes. As electrical probes provide only limited ability to direct the stimulus and thus are not well suited for stimulus of certain areas without also directly stimulating nearby areas. Optogenetic probes disclosed herein provide a mechanism for more precise selection of the stimulus location. For instance, the stimulus from the optogenetic probes can be directed to very specific types of circuits/cells, such as afferent fibers. The following description provides an example implementation consistent with such an embodiment and is meant to show the feasibility and wide-ranging applicability for aspects of present invention.

According to one embodiment of the present disclosure, the invention may be used in animal models of DBS, for example in Parkinsonian rats, to identify the target cell types responsible for therapeutic effects (an area of intense debate and immense clinical importance). This knowledge alone may lead to the development of improved pharmacological and surgical strategies for treating human disease.

One such application involves long-term potentiation (LTP) and/or long-term depression (LTD) between two neural groups. By targeting the expression of a subject opsin to different neural populations and stimulating each with a different frequency of light, LTP or LTD can be accomplished between the two groups. Each group can be individually controlled using the respective wavelength of light. This can be particularly useful for applications in which the spatial arrangement of the two groups presents issues with individual control using the same wavelength of light. Thus, the light delivery device(s) are less susceptible to exciting the wrong neural group and can be less reliant upon precise spatial location of the optical stimulus.

The delivery of the proteins to cells in vivo can be accomplished using a number of different deliver devices, methods and systems. On such delivery device is an implantable device that delivers a nucleotide sequence for modifying cells in vivo, such as a viral-vector. The implantable device can also include a light delivery mechanism. The light delivery can be accomplished using, for example, light-emitting diodes (LEDs), fiber optics and/or Lasers.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Hyperpolarizing Opsins

Material and Methods

All experiments were conducted under protocols approved by the Stanford Administrative Panel on Laboratory Animal Care.

Molecular Cloning

Lentiviral constructs contained BamHI between the promoter and the opsin, NotI between the opsin and the fluorophore, and EcoRI between the fluorophore and the WPRE. Opsin-eYFP fragments were polymerase chain reaction (PCR)-amplified to add AscI and NheI, using gtggcgcgcccattacttgtacagctcgtccatg (SEQ ID NO:11) (for all opsins), tatgctagccaccatggactatggcggcgc (SEQ ID NO: 12) (for the ChR2 mutants), and gttatgctagcgccaccatgtcgcggaggccatggc (SEQ ID NO:13) (for ChIEF), and then ligated to an AAV-Ef1α-DIO backbone cut with those sites.

Mac and Arch were obtained from Addgene as green fluorescent protein (GFP) fusion genes, and switched to enhanced yellow fluorescent protein (eYFP) for consistency. Humanized ArchT was synthesized by DNA2.0. Mac, Arch, and ArchT were enhanced to the 2.0 versions using the endoplasmic reticulum (ER) export element alone and to the 3.0 versions with both the ER export motif and the trafficking signal as described previously[33].

All constructs were fully sequenced to check for accuracy and all AAV vectors were tested for in vitro expression prior to viral production. Complete sequence information is on the website: www(dot)optogenetics(dot)org.

Hippocampal Neuron Culture and Calcium Phosphate Transfections

Primary cultured hippocampal neurons were prepared from P0 Sprague-Dawley rat pups (Charles River). CA1 and CA3 were isolated, digested with 0.4 mg/mL papain (Worthington), and plated onto glass coverslips pre-coated with 1:30 Matrigel (Beckton Dickinson Labware). Cultures were maintained in a 5% $CO_2$ humid incubator with Neurobasal-A medium (Invitrogen) containing 1.25% fetal bovine serum (FBS) (Hyclone), 4% B-27 supplement (Gibco), 2 mM Glutamax (Gibco), and 2 mg/mL 5-Fluoro-2'-deoxyuridine (FUDR) (Sigma), and grown on coverslips in a 24-well plate at a density of 65,000 cells per well.

For each well a $DNA/CaCl_2$ mix was prepared with 2 μg DNA (Qiagen endotoxin-free preparation) and 1.875 μL 2M $CaCl_2$ (final $Ca^{2+}$ concentration 250 mM) in 15 μL $H_2O$. To $DNA/CaCl_2$ was added 15 μL of 2× HEPES-buffered saline (pH 7.05). After 20 mM at room temperature (RT), the mix was added drop-wise into each well (from which the growth medium had been removed and replaced with pre-warmed MEM) and transfection proceeded for 45-60 minutes at 37° C., after which each well was washed with 3×1 mL warm MEM before the original growth medium was returned.

Stereotactic Injections

Adeno-associated virus (AAV) serotype 2/5 was produced by the University of Carolina Chapel Hill Vector Core. Genomic titers were $1.5 \times 10^{12}$ cfu $mL^{-1}$ for $ChETA_A$, $ChETA_{TR}$, and ChIEF, and $4 \times 10^{12}$ cfu $mL^{-1}$ for eYFP, eNpHR3.0, and eArch3.0. 1 μL of virus was stereotactically injected bilaterally into the medial prefrontal cortex of 3-4 week-old mice at +1.7 anteroposterior, 0.4 mediolateral, and 2.5 dorsoventral (in mm from bregma).

Whole-Cell Electrophysiology Recordings

Recordings in cultured neurons were performed 4-6 days post-transfection in Tyrode's solution (320 mOsm): 125 mM NaCl, 2 mM KCl, 2 mM $CaCl_2$, 2 mM $MgCl_2$, 30 mM glucose, and 25 mM HEPES, titrated to pH 7.3-7.4 with NaOH. Tyrode was perfused at a rate of 1-2 mL $min^{-1}$ and was kept at room temperature (20-22° C.). Intracellular solution (300 mOsm) contained 130 mM K-gluconate, 10 mM KCl, 10 mM HEPES, 10 mM EGTA, and 2 mM $MgCl_2$, titrated to pH 7.3 with KOH. Characterization of excitatory opsins was done with bath-applied tetrodotoxin (TTX) (1 μM; Sigma-Aldrich) and intracellular QX-314 chloride (1 mM; Tocris Bioscience). In vitro patching of hyperpolarizing opsins and current clamp recordings for depolarizing opsins were performed in the presence of synaptic transmission blockers 6-cyano-7-nitroquinoxaline-2,3-dione (CNQX; 10 μM; Sigma-Aldrich) and D(-)-2-amino-5-phosphonovaleric acid (APV; 25 μM, Sigma-Aldrich) as well as gabazine for the current clamp experiments (10 μM; Sigma-Aldrich). All recordings of cultured neurons were performed on an upright Leica DM-LFSA microscope.

Recordings of eYFP, eNpHR3.0, and eArch3.0-expressing pyramidal cells were performed in acute slices from wild-type C57BL/6 mice 6-7 weeks after virus injection. ACSF contained CNQX, APV, and gabazine. Intracellular solution (280 mOsm) contained 135 mM K-gluconate, 5 mM KCl, 10 mM HEPES, 0.1 mM EGTA, 2 mM $MgCl_2$, 2 mM Mg-ATP, and 0.2 mM $Na_2$-GTP, titrated to pH 7.4 with KOH. Pyramidal cells were identified by morphology and characteristic electrophysiological properties. Recordings were performed on an upright Olympus BX51 microscope. For all patching experiments, borosilicate glass (Sutter Instruments) pipette resistances were 3-6 MΩ. For cell-attached electrophysiology recordings, upon obtaining GΩ seals, holding potential was set so that no net current flowed across the membrane; the same stimulation protocol used for whole-cell spiking experiments. After the cell-attached recording had been performed, we applied suction to the pipette to break into the cell and repeated the same experiments in whole-cell to provide a direct within-cell comparison. No exogenous retinal co-factor was added to neurons in any preparation.

Light delivery

All experiments were performed using single-photon activation. For cultured neurons, light was emitted from a 300 W DG-4 lamp (Sutter Instruments, Novato, Calif.) and was delivered through a 40×, 0.8 NA water-immersion objective. Pulsed input signals were delivered to the DG-4 from pClamp (Axon Instruments) via a BNC connection. The delay from the DG-4 trigger signal to full light output was measured using an amplified photodetector (Thorlabs) as ~1 ms, with a 200 μs rise-time. All measurements of time-to-peak and latency were corrected for this delay.

For light sensitivity measurements, light was passed through a 470/40 nm filter (for blue-light sensitive excitatory opsins) or a 562/40 nm filter (for C1V1s and all inhibitory opsins), and then through a series of neutral-density (ND) filters to achieve power densities ranging from ~0.1 to 20 mW mm$^{-2}$. Other properties were studied at ~5 mW mm$^{-2}$. For these experiments, the light was passed through a Lambda 10-3 filter wheel (Sutter Instruments) with a 10-position wheel for filters of different wavelengths, ND-normalized to generate closely-matched power densities. Filters were: 406/15; 427/20; 445/20; 470/20; 494/20; 520/15; 542/20; 560/25; 590/20. Inhibitory spectra also used a 607/45 filter. Functional performance of depolarizing tools in culture used a 470/40 nm filter (for blue-light sensitive excitatory tools) or a 562/40 nm filter (for C1V1Ts), and then ND filters to achieve power densities of 2, 6, and 20 mW mm$^{-2}$.

For experiments investigating fast depolarizing tools in slice, light was emitted from the same 300 W DG-4 lamp (Sutter Instruments) and delivered through a 40×, 0.8NA water-immersion objective. Light was passed through a 470/40 nm filter and adjusted to achieve a light power density of 5.1 mW mm$^{-2}$. For experiments investigating hyperpolarizing tools in slice, a 40×/0.8 NA LUMPlanFL/IR Objective (Olympus), XCite halogen light source (EXPO) was used. Light was passed through a 589/15 filter (eNpHR3.0) or a 560/14 filter (eArch3.0). For experiments comparing the photocurrent and hyperpolarization magnitudes under matched conditions, light power density was adjusted to ~5 mW mm$^{-2}$. For the remaining experiments light was adjusted across a range of light power densities (5-10 mW mm$^{-2}$ for eNpHR3.0; 0.25-5 mW mm$^{-2}$ for eArch3.0) in order to achieve a comparable range of photocurrents for both opsins.

All experiments contained at least 30 s of dark between sweeps in order to allow recovery to baseline. All filters are given here as wavelength in nm/bandwidth in nm. All light power densities were measured coming out of the 40× objective, at approximately the sample distance.

Data Analysis

Analyses of physiological results were performed using ClampFit software (Axon Instruments) or custom software written in MATLAB (Mathworks).

Access resistance ($R_a$) and input resistance ($R_{in}$) were monitored continually and data was only included when $R_a$ was <30 MΩ and $R_{in}$ was >90 MΩ. Any traces containing escaped spikes were excluded from analyses of peak photocurrent or of kinetics, but steady-state photocurrents were still measured when possible. For current clamp recordings in culture, only cells that fit those criteria and had leak currents >−150 pA (holding at −65 mV) were included for analysis. For current clamp recordings in acute slice, only cells that fit those criteria and had resting potentials <−55 mV were included for analysis.

To identify the peak photocurrent, traces were smoothed using the robust Loess method with a filter width of 2 ms and the peak was defined as the extremum from laser onset to 200 ms post laser onset, less the baseline current (from the average over 500 ms prior to laser onset). Visual inspection ensured that no escape spikes or other anomalies occurred. Time-to-peak was measured from laser onset to this marked peak time. The steady-state photocurrent was determined by fitting a monoexponential curve to the smoothed waveform from 2 ms after the peak to the laser offset time. Steady-state current was taken from the parameters of this fit. $\tau_{off}$ and $\tau_{des}$ were calculated using ClampFit. The trace was first smoothed using a lowpass Gaussian filter with a −3 dB cutoff at 1,000 Hz; then a monoexponential curve was fit to the smoothed waveform. All curves were visually inspected for goodness of fit.

Photocurrent properties of the depolarizing tools ChR2, ChETA$_A$, and ChIEF were characterized in vitro using both the lentiviral and the adenoassociated virus (AAV) constructs. For parameters that depend on single-molecule properties (steady-state: peak ratio, action spectrum, light sensitivity, and kinetics), values were pooled across experiments after confirming that datasets were not statistically different. Photocurrent properties of the hyperpolarizing tools were assessed in two separate rounds of experiments. eNpHR3.0 photocurrent magnitudes were statistically different between the two datasets, so we only combine datasets when considering normalized values, or intrinsic single-molecule properties (action spectrum, light sensitivity, and kinetics) after confirming that eNpHR3.0 performed similarly across datasets.

Whole-cell spikes were defined as rising above a high threshold (−20 mV for the comparison of fast depolarizing opsins in slice; 0 mV for all other comparisons) and then dropping below a low threshold (−30 mV). Subsequent spikes that occurred within 2 ms of a prior spike were ignored. To detect spikes elicited by light, a window of time from 1-50 ms after the pulse onset was defined. Above 20 Hz, this window was truncated to 1 ms after the current pulse onset to 1 ms after the subsequent pulse onset. The window around the last light pulse was truncated to the same length. Cell-attached spikes were identified using the threshold function in ClampFit. Very small, broad events were not included as spikes. Where the spike data was ambiguous, the trace was inspected manually. For each whole-cell pulse train we calculated the proportion of light pulses that elicited ≥1 spike (pulse efficacy) and that elicited >1 spike (multiple spike likelihood).

Plateau potentials were defined as the offset of the spike waveform from the baseline. For the depolarizing tools in vitro, all cells that fired ≥one spike were included for analysis. For the fast-spiking cells in slice, only traces that had 100% pulse efficacy were included for analysis. Temporal stationarity, the extent to which spiking is sustained at the same reliability over time, was calculated by dividing the light pulses into quartiles and computing the pulse efficacy each quartile. Latency and latency spread across pulse trains were determined as follows: For each light pulse, we measured the time delta from the light pulse onset to the spike time. Latency is the average of these time deltas, and latency spread is the standard deviation of these time deltas. Note that latency spread therefore is a measure of how variable the latencies are within each cell, whereas the error bars on latency are the standard error of mean latencies across cells. Traces in which the cell fired <5 action potentials were excluded from analysis.

Statistical Analysis

All statistical analysis was performed using Graphpad Prism version 5.04 for Windows (GraphPad Software, www (dot)graphpad(dot)com). For two-sample comparisons of a single variable (such as kinetics of $ChETA_A$ vs. ChIEF in slice) it was first tested whether the data followed a Gaussian distribution (Shapiro-Wilk normality test). If the data were detectably non-Gaussian, a non-parametric Mann-Whitney test was performed. If the data well-approximated a Gaussian, an independent, two-sample t-test (equal variance) was performed. In the case of unequal variance (determined by an F test), Welch's correction was applied. All tests were two-tailed with confidence levels of 95%.

For multi-way comparisons of a single variable (such as kinetics of all depolarizing opsins in culture) it was first tested whether the data followed a Gaussian distribution (Shapiro-Wilk normality test). In cases in which distributions were detectably non-Gaussian, a square root transformation was used to stabilize the variance and make the data approximately normal; all data were then compared against one specified "control", correcting for family-wise error using Dunnett's test. If the transformed data were still non-Gaussian, we used the non-parametric Dunn's test. In all cases, overall significance levels of alpha=0.05 (95% confidence interval) were maintained. Comparisons between larger numbers of opsins will therefore have a more conservative alpha (more stringent requirement for significance). This may also result in different significance values assigned to the same comparison, depending on how many comparisons are being performed in parallel. In particular, since some of the same ChR2 and $ChETA_A$ data were included in two comparisons, discrepancies in reported significance values can be attributed to the total number of opsins included in each set of comparisons.

For comparisons across multiple variables (such as spiking performance across frequencies), two-way ANOVAs were performed, followed by post-tests between pairs or against a specified "control". A conservative Bonferroni's correction was used to control the false positive rate. To test the relationship between two opsin properties (such as $\tau_{off}$ vs. EPD50), a nonparametric, two-tailed Spearman correlation with a confidence level of 95% was performed. To estimate the slope, a least-squares regression (either linear or linear on log-log transformed data), minimizing relative distance squared ($1/Y^2$) was performed.

To test the dependency of an opsin property on an experimental condition (e.g. photocurrent vs. light power density), regressions were performed, as follows. First, for analysis of time-to-peak vs. light power density, we performed linear regression on log-log transformed data was performed; and it was compared whether, for each opsin, the best-fit slope differs significantly from 0. Second, for analysis of recovery from desensitization, a non-linear regression was used to fit the mean photocurrent recovery data with a two-phase association curve, constraining $Y_0=0$ and plateau =1. This fit was used to generate the curves and the R-squared values. In a separate analysis, we fit the data for each individual cell, to calculate the time required for 50% recovery. Third, for analysis of light sensitivities, the raw population means was fit with a one-site specific binding curve: $Y=B_{max}*X/(Kd+X)$. In a separate analysis, the photocurrents for each cell were normalized; and the population means and standard errors for each opsin were plotted. This population data was fit the same way to generate the curves and the R-squared values. For each individual cell, a Kd (equilibrium binding constant), which we refer to as EPD50 (50% effective light power density), was obtained.

Population significance thresholds were always set at P<0.05 (*), P<0.01 (), and P<0.001 (*) for the entire family of comparisons. All graphs are shown as mean±standard error of the mean (s.e.m.).

Immunohistochemistry 6 or 4 weeks post-injection, mice were perfused transcardially with PBS followed by 4% paraformaldehyde (PFA). After an overnight post-fix in PFA, brains were equilibrated in 30% sucrose in PBS for at least 24 hours. 40 µm sections were obtained using a frozen microtome, DAPI-stained (1:50,000), and coverslipped with PVA-DABCO (Sigma-Aldrich). Transfected primary hippocampal cultures were fixed for 15 min with 4% PFA. For staining with KDEL (SEQ ID NO: 14), cultures were then permeabilized for 30 min with 0.4% saponin in 2% normal donkey serum (NDS). Primary antibody incubations were performed overnight at 4° C. using a monoclonal antibody marking endogenous ER-resident proteins containing the KDEL (SEQ ID NO:14) retention signal (anti-KDEL 1:200, Abcam). Secondary antibodies (Jackson Laboratories) were applied in 2% NDS for 1 hour at room temperature.

Equipment and Settings

Figure 1B:
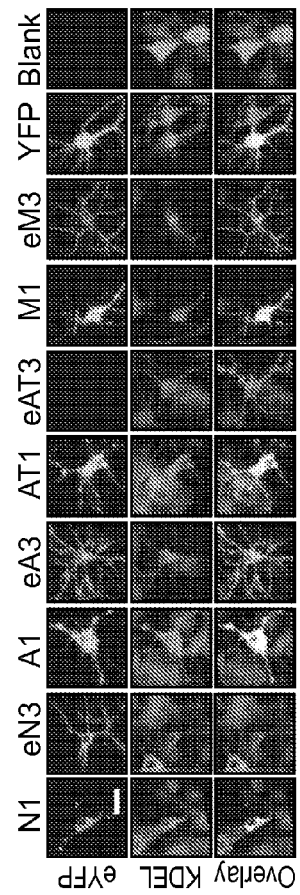

All images were obtained on a Leica confocal microscope (DM600B) as 1024×1024 resolution (pixel dimensions=3.03 µm²). Images were acquired using the following objectives: 10×/0.40 NA (air), 40×/1.25 NA (oil), and 63×/1.4 NA (oil). Excitation and emission wavelengths were as follows: eYFP in FIG. 1b, 514 nm/512-600 nm; eYFP for all other figures, 488 nm/500-545 nm; GFP, 488 nm/500-600 nm; Cy5, 633 nm/650-750 nm. The following figures used line-averaging: FIG. 1b and FIG. 2a. Consistent settings were used for all images in each given figure panel. The brightness and contrast of all eYFP images for FIG. 1b were uniformly and identically modified in Photoshop (Adobe). All other images were unprocessed after acquisition.

Quantification of Fluorescence Levels in Transfected Cells

Fluorescence images were acquired from the same cells that were patched to enable quantification of expression levels and photocurrent/fluorescence relationships. Images were acquired with Metamorph, maintaining constant settings, and processed off-line using ImageJ. Hand-drawn ROIs encompassed the soma and proximal dendrites.

Results

Hyperpolarizing Tools and Properties

Various hyperpolarizing optogenetic tools were compared head-to-head. Although each experiment will have its own unique set of requirements for hyperpolarizing photocurrent properties, some common guiding principles initially seem clear. First, in most experimental applications, hyperpolarizing photocurrents will need to be sufficiently large to robustly and safely inhibit spiking even in the presence of excitatory inputs. Second, higher light sensitivity will likely enable modulation of larger volumes of tissue, the use of lower light powers, and/or less invasive light delivery. Third, precise, time-locked inhibition will presumably require photocurrents with rapid onset and offset, while longer-term inhibition will require photocurrents that are stable, with minimal desensitization. Finally the nature of the action spectrum will dictate feasibility of combining with other light-activated reagents in the same preparation[32, 33].

The first hyperpolarizing tool shown to be efficacious in neurons was the N. pharaonis halorhodopsin (NpHR), a yellow light-activated chloride pump that has now been used in preparations ranging across mammalian brain slice[32], freely moving worms[32], cultured neurons[32, 34], and behaving mammals[35-38]. Two versions modified for enhanced membrane targeting in mammalian neurons, termed eNpHR2.0[39] and eNpHR3.0[33] have since been reported. The outward proton pumps Arch[40] (from *Halorubrum sodomense*), ArchT[41] (from *Halorubrum* strain TP009), eBR[33] (from *Halobacterium*) and Mac[40] (from *Leptosphaeria maculans*) have also recently been shown to achieve successful neuronal inhibition. eNpHR3.0 has larger photocurrents than eNpHR2.0, and Arch has larger photocurrents than eNpHR2.0[40], but no direct comparison between eNpHR3.0 and Arch or any of the proton pumps has yet been reported. Below is presented a direct comparison of the most potent hyperpolarizing opsins (FIG. 1a), including novel membrane trafficking-enhanced versions of proton pumps resulting in the highest expression levels and inhibitory photocurrents yet described. Properties were charaterized in vitro; then the functional performance of two of the most promising candidates in acute slice was tested.

Each hyperpolarizing tool was fused in-frame with enhanced yellow fluorescence protein (eYFP), cloned the opsins into an identical lentiviral backbone with the excitatory CaMKIIα promoter (FIG. 1a); and the opsins were expressed in cultured neurons (FIG. 1b). eNpHR3.0 was well-targeted to the membrane, but Arch, ArchT, and Mac all showed intracellular accumulations reminiscent of the endoplasmic reticulum (ER)-aggregations observed with NpHR1.0[39]. The same accumulations were also observed in the GFP versions of the constructs; the GFP and YFP 1.0 versions had similar photocurrents. ER-aggregation was confirmed by co-staining with the ER marker KDEL (SEQ ID NO: 14) (FIG. 1b). Trafficking modifications applied to eNpHR3.0 were applied to Arch, ArchT, and Mac. These novel trafficking-enhanced versions, which are termed (by analogy with NpHR version progression) eArch3.0, eArchT3.0, and eMac3.0, had markedly reduced intracellular labeling and improved membrane-localization with labeling of cellular processes (FIG. 1b). Intermediate "2.0" versions were potent but not as successful as the 3.0 versions.

Figure 1C:
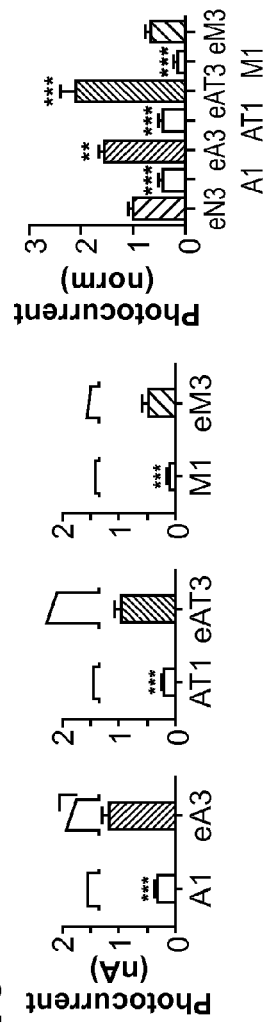

Because only those proteins expressed on the membrane can contribute to the measured photocurrent, it was anticipated that this improved opsin trafficking should increase photocurrent size. Indeed, all three enhanced proton pumps had dramatically increased photocurrents (P<0.001; FIG. 1c). While the 1.0 versions of the proton pumps had significantly smaller photocurrents than eNpHR3.0, eArch3.0 and eArchT3.0 photocurrents were significantly larger (P<0.001 for each comparison; FIG. 1c). eNpHR3.0-expressing cells had the dimmest fluorescence, but the greatest photocurrent per fluorescence, of these tools.

Although maximal eMac3.0 photocurrents were the smallest among the enhanced opsins (and significantly smaller than eNpHR3.0; P<0.05), Mac has been reported to have an activation spectrum sufficiently blue-shifted to allow dual-inhibition in combination with eNpHR3.0[64]. After verifying that membrane trafficking did not change the spectra, the spectra of the enhanced pumps were compared, and plotted with ChR2, for reference (FIG. 1d). eNpHR3.0 was red-shifted (peaking at 560-590 nm) relative to the three proton pumps (peaking at 520-560 nm), exhibiting the least overlap with ChR2; no functionally relevant differences were seen among the proton pumps.

The temporal precision of hyperpolarizing photocurrents was investigated by quantifying on-kinetics ($\tau_{on}$) and off-kinetics ($\tau_{off}$) at the beginning and end of a 1 s light pulse. All pumps activated rapidly, with proton pumps activating significantly faster than eNpHR3.0 (all within the range of 1.5-3 ms, FIG. 1e). Both Mac variants had much slower off-kinetics compared with the other pumps (P<0.001; FIG. 1e).

The light sensitivity of the hyperpolarizing pumps was assessed by measuring photocurrents across a range of light power densities ranging from ~0.05 to ~20 mW mm$^{-2}$ (FIG. 1f); due to small photocurrents, Mac1.0 was eliminated from this and subsequent analyses.) As expected, the 3.0 pumps had much larger operational light sensitivity (that is, by absolute current magnitude) than the 1.0 counterparts, although trafficking-enhancement did not affect the population sensitivity (normalized current magnitudes or EPD50). eMac3.0 was the most sensitive (EPD50 =1.9±0.4 mW mm$^{-2}$ vs. 5.4±0.2 mW mm$^{-2}$ for eNpHR3.0; P<0.001). Off-kinetics and population light sensitivity were therefore inversely correlated for the hyperpolarizing tools, reminiscent of the pattern observed for depolarizing tools.

Given that many behavioral neuroscience experiments may require prolonged inhibition on the order of minutes, the stability of the hyperpolarizing photocurrents was investigated. While all pump photocurrents decayed across 60 s of continuous light, eNpHR3.0 currents were the most persistent and the large 3.0 proton pump currents (eArch3.0 and eArchT3.0) had the largest drop-off in vitro. All pumps recovered photocurrents with similar efficacy under these cultured-neuron conditions.

FIG. 1: Properties of hyperpolarizing tools. (a) NpHR is an inward chloride pump (halorhodopsin type; HR), while Arch, ArchT, and Mac are outward proton pumps (bacteriorhodopsin type; BR). 3.0 versions include a trafficking sequence (TS) between opsin and fluorophore and the 2.0-type endoplasmic reticulum export sequence (ER) after the fluorophore. (b) Confocal images of 1.0 and 3.0 versions (green) expressed in culture and immunolabeled with an ER marker (anti-KDEL (SEQ ID NO: 14); red). Horizontal scale bar represents 25 μm. (c) Representative traces and raw photocurrents in response to 1 s light for 1.0 (open bars) vs. 3.0 versions (closed bars) for Arch (n=15-19), ArchT (n=14-16), and Mac (n=8-12). Vertical and horizontal scale bars represent 500 pA and 500 ms, respectively. Photocurrents were normalized to eNpHR3.0 values from within the same experiment to enable direct comparisons across opsins (n=835). (d) Action spectra for 3.0 versions (n=7-20) alongside ChR2 (black). (e) $\tau_{on}$ and $\tau_{off}$ (n=7-35). Vertical and horizontal scale bars represent 200 pA and 5 ms, respectively. (f) EPD50 for all hyperpolarizing opsins (n=5-14). Raw photocurrent vs. light power density plotted alongside within-experiment eNpHR3.0 (n=5-14). All population data is plotted as mean±s.e.m. Stars indicate significance level: * P<0.05, ** P<0.01, * ** P<0.001. Unless otherwise indicated, eNpHR3.0 was activated with 590 nm light, while all other tools were activated with 560 nm light, both at ~5 mW mm$^{-2}$.

Hyperpolarizing Tools: Inhibiting Spikes in in Acute Slice

To further investigate the characteristics of prolonged photocurrents under conditions more relevant to in vivo experiments, and to test the functional ability of hyperpolarization to stably inhibit spiking, acute slice preparations were used. For this analysis, one of each broad class of hyperpolarizing tool (namely, the chloride pump eNpHR3.0 against one of the proton pumps) was compared. The enhanced counterpart of the best-established proton pump (Arch1.0) to date, namely eArch3.0 was used. To express eNpHR3.0 and eArch3.0 in vivo, an adeno-associated viral vector (AAV serotype 2/5), with the opsin-eYFP fusion gene under control of the CaMKIIα promoter, was stereotactically injected. Under matched conditions, eArch3.0 expressed much more strongly based on fluorescence, both at the injection site and in axons at downstream targets such as the basolateral amygdala (BLA; FIG. 2a). Compared with eYFP-transduced controls, cells expressing both opsins had similar baseline input resistances (FIG. 2b) and resting potentials, but slightly higher membrane capacitance, as has previously been observed for opsin-expressing HEK cells[42]. Also as expected from the in vitro work (FIG. 1), at matched light power densities (5 mW mm$^{-2}$) eArch3.0 had significantly larger photocurrents (P=0.01), averaging 1680±360 pA vs. 450±70 pA for eNpHR3.0 (FIG. 2c). Under current-clamp, eArch3.0-mediated hyperpolarization was also significantly larger (−94±12 mV vs. −41±4 mV, P=0.005; FIG. 2d); smaller differences in hyperpolarization compared with photocurrent could be due to voltage-dependent slowing of photocycle turnover in proton pumps.

Because photocurrent stability and cell responses to hyperpolarization may depend on photocurrent magnitudes, a set of experiments was carried using non-matched light power densities (5-10 mW mm$^{-2}$ for eNpHR3.0; 0.25-5 mW mm$^{-2}$ for eArch3.0) to obtain a similar range of photocurrents for the two tools. Cells were illuminated for 60 s under voltage clamp, and measured the start and end photocurrent for each cell. These data were well-fit by linear regression (eNpHR3.0 $R^2$=0.68, eArch3.0 $R^2$=0.88) with eArch3.0 having significantly higher slope ($F_{1,36}$=22.2, P<0.001), reflecting the fact that, for cells with similar onset photocurrents, eArch3.0-expressing cells had more photocurrent remaining at the end of the light pulse under these slice conditions, as seen in the illustrative traces and in contrast with the pattern of stability observed in vitro.

The ability of eArch3.0 and eNpHR3.0 to inhibit spiking in current clamp was assessed. Spiking was elicited with modestly suprathreshold current injections at 5 Hz, with 30 s baseline (pre-light), 60 s light, and 30 s post-light. Both pumps successfully blocked spikes throughout the duration of the prolonged light stimulation (FIG. 2e). We observed that from both groups some cells became unstable after prolonged hyperpolarization especially by >50 mV, failing to spike to current injections or rebounding to a more depolarized resting potential after light offset. These factors were quantified for each cell and plotted each against the degree of hyperpolarization (FIG. 2f). Under more moderate (>50 mV) hyperpolarizations, no consistent or lasting effects on excitability or membrane resistance were observed.

FIG. 2: Performance of hyperpolarizing tools. (a) Confocal images of eNpHR3.0 and eArch3.0 expression at the injection site in medial prefrontal cortex (mPFC) and the downstream basolateral amygdala (BLA). Scale bars represent 250 μm and 25 μm. DAPI staining (white) delineates cell bodies. (b) Mean input resistances for opsin-expressing cells and eYFP-controls (n=10-22). (c) Representative traces and mean onset photocurrents for eArch3.0 and eNpHR3.0 in response to 60 s 5 mW mm$^{-2}$ light pulses (n=8-10). Vertical and horizontal scale bars represent 400 pA and 10 s, respectively. (d) Mean peak hyperpolarization generated by eArch3.0 and eNpHR3.0 with 60 s 5 mW mm$^{-2}$ light pulses (n=6-10). (e) Suppression of current injection-evoked spiking in reliably-firing cells by 60 s of continuous light in cells expressing eNpHR3.0 or eArch3.0. Cells were illuminated with light power densities set to achieve approximately matched hyperpolarization. Vertical and horizontal scale bars represent 40 mV and 20 s, respectively. (f) Relationship between hyperpolarization magnitude and cell stability. Post-light recovery of evoked spiking (relative to pre-light performance) and change in resting potential plotted against light-evoked hyperpolarization. All population data is plotted as mean±s.e.m. Stars indicate significance level: * P<0.05,  P<0.01, * P<0.001. eNpHR3.0 was activated with 590 nm light, while eArch3.0 was activated with 560 nm light.

Example 2

Cloning and Characterization of *Dunaliella salina* Opsin

Typically found in hyper-saline environments such as evaporation salt fields, the unicellular (oval with two flagella) green alga *Dunaliella salina* is salt tolerant. Despite belonging to the same order as the green algae *Chlamydomonas reinhardtii* and *Volvox carteri*, *Dunaliella* can appear reddish due to the accumulation of high levels of carotenoid molecules (FIG. 3A). We hypothesized that a *Dunaliella* ChR might have unusual properties and engaged in efforts to clone ChRs from this flagellated algal species.

Despite high homology with other known ChRs, the DChR1 sequence contained several notable features (FIG. 3B). First, one of the residues that is thought to contribute to the complex counterion of the RSB, E123 in ChR2 as discussed above, is replaced by Ala in the DChR1 TM3 (FIG. 3B,C); from structural modeling (FIG. 3C), it was expected that the counterion function is assumed by E309 in DChR1, a position that plays only a minor role in BR (D212) or *Anabaena* sensory rhodopsin (ASR) (Vogeley et al., 2004). Even more remarkably, DChR1 photocurrents were exclusively carried by protons, unlike any other known ChR, and were completely unaffected by changes in the extracellular cation composition (FIG. 3D). Consequently, the photocurrent was highly sensitive to changes in the pH environment and completely vanished at high pH (FIG. 3E).

Full understanding of structure-function relationships will require high-resolution crystal structures in multiple photocycle states. However, directed mutagenesis studies here demonstrate that DChR1 has a different counterion arrangement and ion selectivity compared to other known ChRs. The strict H[30] selectivity of DChR1 was not mediated by the unusual protonated retinal Schiff base (RSBH) counter ion, as substitution of A178 with the more typical putative counterion Glu as found in ChR2 only red-shifted the activation spectrum (FIG. 3F, from 475 to 510 nm) with minimal effect on current amplitude or kinetics. Similarly, replacing E309 with Asp caused a slight spectral shift and a slight current increase, whereas replacing the charged E309 by Ala rendered the protein almost totally inactive (FIG. 3F).

Given typical electrochemical proton gradients, the DChR1 H$^+$ current direction is opposite in direction to the H$^+$ current generated by bacteriorhodopsin (BR) pump activity; therefore, DChR1 and BR could enable interventions such as bidirectional control of cellular pH, for example in manipulating the pH of intracellular compartments (mitochondria and synaptic vesicles). DChR1 therefore defines a novel class of microbial opsin—a light-activated proton channel—unlike any other microbial opsin including ChR1 and ChR2. These findings illustrate the diversity of function likely to be present within the vast array of microbial opsin genomes.

FIG. 3. Characterization of a channelrhodopsin from *Dunaliella salina*. A. The halophilic unicellular alga *Dunaliella salina*. B. Sequence homology between the algal channelrhodopsins and BR within the third transmembrane helix. The typically conserved E123 position has been replaced with an Ala in DChR1 (and is shown on a yellow background), conserved residues are shown on a blue background, and amino acids likely interacting with the chromophore are shown in red. C. Lack of a proton acceptor in DChR1, compared with BR and Chlamydomonas ChR2 (CChR2). ASR (*Anabaena* sensory rhodopsin) has been crystallized with a mixture of all-trans retinal seen as an overlay (Vogeley et al., 2004). D. DChR1 photocurrents are unaffected by changes in the extracellular cation composition (sole cation present in each condition shown on category X axis). Cation exchange was performed in 5 mM Mops-NMG, 0.1 mM $MgCl_2$ with 100 mM LiCl, KCl, NaCl, Guanidium chloride or NMG chloride (pH 7.5). We used a human-codon adapted DChR sequence (amino acid residues 1-339) as a template for capped RNA synthesis by T7 RNA polymerase (mMessage mMachine, Ambion). Oocyte preparation, injection of capped RNA were carried out as described previously (Berthold et al. 2008), and two-electrode voltage clamp was performed with a Turbo Tec-05 (NPI Electronic) or a GeneClamp 500 (Molecular Devices) amplifier on an oocyte after 3-7 days of the capped RNA injection. Continuous light was provided by a 75-W Xenon lamp (Jena Instruments) and delivered to the oocytes via a 3-mm light guide. The light passed through a 500 25-nm broadband filter (Balzers) with an intensity of 46 mW/cm². E. In contrast, DChR1 photocurrent is highly sensitive to changes in the pH environment. Solutions contained 100 mM NMG-chloride, 0.1 mM $MgCl_2$, 0.1 mM $CaCl_2$ with 5 mM glycine (pH 9.0), 5 mM Mops-NMG (pH 7.5), 5 mM citrate (pH 6, 5.5, 5.0, 4.6, 4.2). F. Introduction or alteration of a proton acceptor (A178E or E309D) into the DChR1 retinal-binding pocket causes a pronounced red-shift in the absorption spectrum. We applied 10-ns laser flashes as described previously (Berthold et al. 2008); solutions for action spectra recording contained 100 mM NaCl, 0.1 mM $MgCl_2$, 0.1 mM $CaCl_2$ and 5 mM citrate (pH 4.2).

A nucleotide sequence endoding *D. salina* DChR1 is presented in FIG. 4. The DChR1-encoding nucleotide sequence was codon-optimized for mammalian expression; the codon-optimized nucleotide sequence is depicted in FIG. 5. FIG. 6 provides an amino acid sequence of *D. salina* DChR1.

REFERENCES

1. Deisseroth, K. Optogenetics. *Nat Methods* 8, 26-29 (2011).
2. Deisseroth, K. Controlling the brain with light. *Sci Am* 303, 48-55 (2010).
3. Fenno, L., Yizhar, O. & Deisseroth, K. The development and application of optogenetics. *Annu Rev Neurosci* 34, 389-412 (2011).
4. Yizhar, O., Fenno, L. E., Davidson, T. J., Mogri, M. & Deisseroth, K. Optogenetics in neural systems. *Neuron* 71, 9-34 (2011).
5. Wang, C., Kane, M. A. & Napoli, J. L. Multiple retinol and retinal dehydrogenases catalyze all-trans-retinoic acid biosynthesis in astrocytes. *J Biol Chem* 286, 6542-6553 (2011).
6. Boyden, E. S., Zhang, F., Bamberg, E., Nagel, G. & Deisseroth, K. Millisecond-timescale, genetically targeted optical control of neural activity. *Nat Neurosci* 8, 1263-1268 (2005).
7. Li, X. et al. Fast noninvasive activation and inhibition of neural and network activity by vertebrate rhodopsin and green algae channelrhodopsin. *Proc Nati Acad Sci USA* 102, 17816-17821 (2005).
8. Bi, A. et al. Ectopic expression of a microbial-type rhodopsin restores visual responses in mice with photoreceptor degeneration. *Neuron* 50, 23-33 (2006).
9. Ishizuka, T., Kakuda, M., Araki, R. & Yawo, H. Kinetic evaluation of photosensitivity in genetically engineered neurons expressing green algae light-gated channels. *Neurosci Res* 54, 85-94 (2006).
10. Nagel, G. et al. Light activation of channelrhodopsin-2 in excitable cells of *Caenorhabditis elegans* triggers rapid behavioral responses. Curr Biol 15, 2279-2284 (2005).
11. Yizhar, O. et al. Neocortical excitation/inhibition balance in information processing and social dysfunction. Nature (2011).
12. Gradinaru, V. et al. Targeting and readout strategies for fast optical neural control in vitro and in vivo. *J Neurosci* 27, 14231-14238 (2007).
13. Gunaydin, L.A. et al. Ultrafast optogenetic control. *Nat Neurosci* 13, 387-392 (2010).
14. Berndt, A. et al. High-efficiency Channelrhodopsins for fast neuronal stimulation at low light levels. *Proc Natl Acad Sci USA* (2011).
15. Berndt, A., Yizhar, O., Gunaydin, L. A., Hegemann, P. & Deisseroth, K. Bi-stable neural state switches. *Nat Neurosci* 12, 229-234 (2009).
16. Kleinlogel, S. et al. Ultra light-sensitive and fast neuronal activation with the Ca(2+)-permeable channelrhodopsin CatCh. *Nat Neurosci* 14, 513-518 (2011).
17. Zhang, F. et al. Red-shifted optogenetic excitation: a tool for fast neural control derived from Volvox carteri. *Nat Neurosci* 11, 631-633 (2008).
18. Govorunova, E. G., Spudich, E. N., Lane, C. E., Sineshchekov, O. A. & Spudich, J. L. New channelrhodopsin with a red-shifted spectrum and rapid kinetics from Mesostigma viride. *MBio* 2, e00115-00111 (2011).
19. Lin, J. Y., Lin, M. Z., Steinbach, P. & Tsien, R.Y. Characterization of engineered channelrhodopsin variants with improved properties and kinetics. *Biophys J* 96, 1803-1814 (2009).
20. Wang, H. et al. Molecular determinants differentiating photocurrent properties of two channelrhodopsins from chlamydomonas. *J Biol Chem* 284, 5685-5696 (2009).
21. Wen, L. et al. Opto-current-clamp actuation of cortical neurons using a strategically designed channelrhodopsin. *PLoS One* 5, e12893 (2010).
22. Stehfest, K. & Hegemann, P. Evolution of the channelrhodopsin photocycle model. *Chemphyschem* 11, 1120-1126.
23. Bamann, C., Kirsch, T., Nagel, G. & Bamberg, E. Spectral characteristics of the photocycle of channelrhodopsin-2 and its implication for channel function. *J Mol Biol* 375, 686-694 (2008).
24. Sugiyama, Y. et al. Photocurrent attenuation by a single polar-to-nonpolar point mutation of channelrhodopsin-2. *Photochem Photobiol Sci* 8, 328-336 (2009).
25. Hedrick, T. & Waters, T. H. Spiking patterns of neocortical L5 pyramidal neurons in vitro change with temperature. *Front Cell Neurosci* 5, 1 (2011).
26. Lin, J. Y. A User's Guide to Channelrhodopsin Variants: Features, Limitations and Future Developments. *Exp Physiol* (2010).
27. Cardin, J. A. et al. Driving fast-spiking cells induces gamma rhythm and controls sensory responses. *Nature* 459, 663-667 (2009).

28. Sohal, V. S., Zhang, F., Yizhar, O. & Deisseroth, K. Parvalbumin neurons and gamma rhythms enhance cortical circuit performance. *Nature* 459, 698- 702 (2009).

29. Tsai, H. C. et al. Phasic firing in dopaminergic neurons is sufficient for behavioral conditioning. *Science* 324, 1080-1084 (2009).

30. Atasoy, D., Aponte, Y., Su, H. H. & Sternson, S. M. A FLEX switch targets Channelrhodopsin-2 to multiple cell types for imaging and long-range circuit mapping. *J Neurosci* 28, 7025-7030 (2008).

31. Chater, T. E., Henley, J. M., Brown, J. T. & Randall, A. D. Voltage- and temperature-dependent gating of heterologously expressed channelrhodopsin-2. *J Neurosci Methods* 193, 7-13 (2010).

32. Zhang, F. et al. Multimodal fast optical interrogation of neural circuitry. *Nature* 446, 633-639 (2007).

33. Gradinaru, V. et al. Molecular and cellular approaches for diversifying and extending optogenetics. *Cell* 141, 154-165 (2010).

34. Han, X. & Boyden, E. S. Multiple-color optical activation, silencing, and desynchronization of neural activity, with single-spike temporal resolution. *PLoS One* 2, e299 (2007).

35. Witten, I. B. et al. Cholinergic interneurons control local circuit activity and cocaine conditioning. *Science* 330, 1677-1681 (2010).

36. Stuber, G. D. et al. Excitatory transmission from the amygdala to nucleus accumbens facilitates reward seeking. *Nature* 475, 377-380 (2011).

37. Tye, K. M. et al. Amygdala circuitry mediating reversible and bidirectional control of anxiety. *Nature* 471, 358-362 (2011).

38. Goshen, I., Brodsky, M., Prakash, R. & Deisseroth, K. *Cell* (2011).

39. Gradinaru, V., Thompson, K. R. & Deisseroth, K. eNpHR: a *Natronomonas* halorhodopsin enhanced for optogenetic applications. *Brain Cell Biol* 36, 129-139 (2008).

40. Chow, B. Y. et al. High-performance genetically targetable optical neural silencing by light-driven proton pumps. *Nature* 463, 98-102 (2010).

41. Han, X. et al. A high-light sensitivity optical neural silencer: development and application to optogenetic control of non-human primate cortex. *Front. Syst. Neurosci.* 5 (2011).

42. Zimmermann, D. et al. Effects on capacitance by overexpression of membrane proteins. *Biochem Biophys Res Commun* 369, 1022-1026 (2008).

43. Zhao, Y. et al. An expanded palette of genetically encoded Ca(2) indicators. *Science* 333, 1888-1891 (2011).

44. Goto, Y. & O'Donnell, P. Network synchrony in the nucleus accumbens in vivo. *J Neurosci* 21, 4498-4504 (2001).

45. Sanchez-Vives, M. V. & McCormick, D. A. Cellular and network mechanisms of rhythmic recurrent activity in neocortex. *Nat Neurosci* 3, 1027-1034 (2000).

46. Nagel, G. et al Channelrhodopsin-2, a directly light-gated cation-selective membrane channel *Proc Natl Acad Sci USA* 100, 13940-13945 (2003).

47. Goold, C. P. & Nicoll, R. A. Single-cell optogenetic excitation drives homeostatic synaptic depression. *Neuron* 68, 512-528 (2010).

48. Lindsay, T. H., Thiele, T. R. & Lockery, S. R. Optogenetic analysis of synaptic transmission in the central nervous system of the nematode *Caenorhabditis elegans*. *Nat Commun* 2, 306 (2011).

49. Taylor, C. P. & Dudek, F. E. Synchronous neural afterdischarges in rat hippocampal slices without active chemical synapses. *Science* 218, 810-812 (1982).

50. Ren, J. et al. Habenula "cholinergic" neurons co-release glutamate and acetylcholine and activate postsynaptic neurons via distinct transmission modes. *Neuron* 69, 445-452 (2011).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated fusion polypeptide comprising, in order from N-terminus to C-terminus:
   a) an opsin polypeptide comprising an amino acid sequence having at least 90% amino acid sequence identity to the amino acid sequence set forth in SEQ ID NO:33;
   b) a membrane trafficking signal comprising the amino acid sequence KSRITSEGEYIPLDQIDINV (SEQ ID NO:10); and
   c) an ER export signal comprising the amino acid sequence FCYENEV (SEQ ID NO:5).

2. The fusion polypeptide of claim 1, wherein the opsin polypeptide comprises an amino acid sequence having at least 95% amino acid sequence identity to the amino acid sequence set forth in SEQ ID NO:33.

3. The fusion polypeptide of claim 1, wherein the opsin polypeptide comprises an amino acid sequence having at least 96% amino acid sequence identity to the amino acid sequence set forth in SEQ ID NO:33.

4. The fusion polypeptide of claim 1, wherein the opsin polypeptide comprises an amino acid sequence having at least 97% amino acid sequence identity to the amino acid sequence set forth in SEQ ID NO:33.

5. The fusion polypeptide of claim 1, wherein the opsin polypeptide comprises an amino acid sequence having at least 98% amino acid sequence identity to the amino acid sequence set forth in SEQ ID NO:33.

* * * * *